(12) United States Patent
Gong

(10) Patent No.: US 10,364,420 B2
(45) Date of Patent: Jul. 30, 2019

(54) DIMERIC REVERSE TRANSCRIPTASE

(71) Applicant: Bio-Rad Laboratories, Inc., Hercules, CA (US)

(72) Inventor: Xiao-Song Gong, Richmond, CA (US)

(73) Assignee: BIO-RAD LABORATORIES, INC, Hercules, CA (US)

( * ) Notice: Subject to any disclaimer, the term of this patent is extended or adjusted under 35 U.S.C. 154(b) by 0 days.

(21) Appl. No.: 15/370,646

(22) Filed: Dec. 6, 2016

(65) Prior Publication Data

US 2017/0159032 A1    Jun. 8, 2017

Related U.S. Application Data

(60) Provisional application No. 62/264,223, filed on Dec. 7, 2015.

(51) Int. Cl.
*C12N 9/12*        (2006.01)

(52) U.S. Cl.
CPC .... *C12N 9/1252* (2013.01); *C12Y 207/07007* (2013.01); *C07K 2319/00* (2013.01); *C12N 2740/13022* (2013.01)

(58) Field of Classification Search
None
See application file for complete search history.

(56) References Cited

U.S. PATENT DOCUMENTS

| | | | |
|---|---|---|---|
| 6,271,354 B1 | 8/2001 | Srinivisan et al. | |
| 6,436,648 B1 | 8/2002 | Srinivisan et al. | |
| 6,518,019 B2 | 2/2003 | Gerard et al. | |
| 6,835,561 B1 | 12/2004 | Gerard et al. | |
| 7,115,406 B2 | 10/2006 | Gerard et al. | |
| 2004/0058362 A1 | 3/2004 | Frey et al. | |
| 2004/0259115 A1 | 12/2004 | Schuster et al. | |
| 2007/0141591 A1 | 6/2007 | Borns | |
| 2012/0009630 A1 | 1/2012 | Lambowitz et al. | |
| 2014/0308730 A1 | 10/2014 | Nikiforov et al. | |
| 2014/0322789 A1 | 10/2014 | Lee | |

FOREIGN PATENT DOCUMENTS

| | | |
|---|---|---|
| EP | 1149170 A1 | 10/2001 |
| WO | 99/47649 A2 | 9/1999 |
| WO | 01/61015 A2 | 8/2001 |
| WO | 2004/087868 A2 | 10/2004 |

OTHER PUBLICATIONS

Wang, et al., "A novel strategy to engineer DNA polymerases for enhanced processivity and improved performance in vitro," Nucleic Acids Res, 2004, vol. 32(3), p. 1197-1207.
International Search Report and Written Opinion dated Feb. 17, 2017 in PCT/US16/65119, 12 pages.
Extended European Search Report in EP Application 16873667.6 dated Mar. 26, 2019; 8 pages.
Hizi, A. et al.; "Retroviral reverse transcriptases (other than those of HIV-1 and murine leukemia virus): A comparison of their molecular and biochemical propertyes"; *Virus Research*; Amsterdam, NL; vol. 134, No. 1-2; Jun. 1, 2008; pp. 203-220.
Perler, F.B. et al.; "Thermostable DNA Polymerases"; *Advances in Protein Chemistry*; Academic Press, New York, NY; vol. 48; Jan. 1, 1996; pp. 377-435.

*Primary Examiner* — Richard G Hutson
(74) *Attorney, Agent, or Firm* — Saliwanchik, Lloyd & Eisenschenk

(57) ABSTRACT

Covalently-linked DNA polymerases are provided.

19 Claims, No Drawings
Specification includes a Sequence Listing.

DIMERIC REVERSE TRANSCRIPTASE

-REFERENCE TO RELATED PATENT APPLICATIONS

The present patent application claims benefit of priority to U.S. Provisional Patent Application No. 62/264,223, filed on Dec. 7, 2015, which is incorporated by reference for all purposes.

REFERENCE TO A "SEQUENCE LISTING" SUBMITTED AS ASCII TEXT FILES VIA EFS-WEB

The Sequence Listing written in file 094260-110910US-1031619_SeqList.txt created on Nov. 28, 2016, 200,388 bytes, machine format IBM-PC, MS-Windows operating system, in accordance with 37 C.F.R. §§ 1.821- to 1.825, is hereby incorporated by reference in its entirety for all purposes:

BACKGROUND OF THE INVENTION

The detection, analysis, transcription, and amplification of nucleic acids are frequently-used procedures in modern molecular biology. DNA polymerases are useful for detection and amplification of DNA or RNA. The application of such procedures for RNA analysis can involve the investigation of gene expression, diagnosis of infectious agents or genetic diseases, and the generation of cDNA, to name but a few applications. The reverse transcription ("RT") of RNA thus has many uses. In some instances, the RT is followed by polymerase chain reaction amplification which can be used for rapid detection and quantification of RNA. This procedure is often referred to as "RT-PCR".

BRIEF SUMMARY OF THE INVENTION

Polypeptides comprising at least two DNA polymerases covalently linked together are provided. Such polypeptides have increased stability and can have reduced reaction times compared to monomer DNA polymerases. In some embodiments, a polypeptide comprising a first DNA polymerase and a second DNA polymerase covalently linked by a heterologous linker is provided. In some embodiments, the first DNA polymerase is a first reverse transcriptase and the second DNA polymerase is a second reverse transcriptase.

In some embodiments, the polypeptide is a fusion protein and the heterologous linker is an amino acid linker that links the carboxyl terminus of the first reverse transcriptase to the amino terminus of the second reverse transcriptase. In some embodiments, the polypeptide further comprises a third reverse transcriptase covalently linked by a second linker to the first or second reverse transcriptase.

In some embodiments, the polypeptide is no more than 1400, 1500, 1600, 1700, 1800, 1900 or 2000 amino acids in length.

In some embodiments, the first reverse transcriptase and the second reverse transcriptase are identical. In some embodiments, the first reverse transcriptase and the second reverse transcriptase are at least 80%, 85%, 90%, or 95% identical. In some embodiments, the first and second reverse transcriptases are a murine leukemia virus (MLV) reverse transcriptase. In some embodiments, the first and second reverse transcriptases are a Feline leukemia virus (FLV) reverse transcriptase.

In some embodiments, the first reverse transcriptase and the second reverse transcriptase are less than 70%, 75%, 80%, 95% or 90% identical.

In some embodiments, the amino acid linker is between 1-30 or 1-50 (e.g., 1-15, 3-25) amino acids long.

In some embodiments, the first or second reverse transcriptase is selected from the group consisting of murine leukemia virus (MLV) reverse transcriptase, Feline leukemia virus (FLV) reverse transcriptase, bovine leukemia virus (BLV), Avian Myeloblastosis Virus (AMV) reverse transcriptase, Respiratory Syncytial Virus (RSV) reverse transcriptase, Equine Infectious Anemia Virus (EIAV) reverse transcriptase, Rous-associated Virus-2 (RAV2) reverse transcriptase, SUPERSCRIPT II reverse transcriptase, SUPERSCRIPT I reverse transcriptase, THERMOSCRIPT reverse transcriptase and MMLV RNase H-reverse transcriptase.

In some embodiments, the first reverse transcriptase is a murine leukemia virus (MLV) reverse transcriptase and the second reverse transcriptase is a Feline leukemia virus (FLV) reverse transcriptase. In some embodiments, the first reverse transcriptase is a Feline leukemia virus (FLV) reverse transcriptase and the second reverse transcriptase is a murine leukemia virus (MLV) reverse transcriptase.

In some embodiments, at least the first or the second reverse transcriptase have at least one mutation compared to a naturally-occurring reverse transcriptase. In some embodiments, the first or the second reverse transcriptase is an RNase H-reverse transcriptase.

In some embodiments, the first DNA polymerase is a first DNA-dependent polymerase and/or the second DNA polymerase is a second DNA-dependent polymerase. In some embodiments, the first DNA polymerase is a DNA-dependent polymerase and the second DNA polymerase is a reverse transcriptase. In some embodiments, the first DNA polymerase is a reverse transcriptase and the second DNA polymerase is a DNA-dependent polymerase.

Also provided is nucleic acid (optionally isolated or purified) encoding a polypeptide as described above or elsewhere herein. Also provided is a polynucleotide vector comprising the nucleic acid as described herein. Also provided is a host cell (e.g., a prokaryotic, fungal, yeast, of eukaryotic cell) comprising the vector.

Also provided is a reaction mixture comprising: purified mRNA; and the polypeptide as described above or elsewhere herein. In some embodiments, the reaction mixture further comprises a buffer selected from the group consisting of Tris, HEPES, ACES, PIPES, MOPSO, BES, MOPS, TES, TAPSO, POPSO, BICINE, TAPS, and AMPSO. In some embodiments, the reaction mixture further comprises at least one oligonucleotide primer and/or deoxynucleotides.

Also provided is a kit comprising the polypeptide as described above or elsewhere herein. In some embodiments, the polypeptide comprises one or two reverse transcriptases and the kit further comprises a DNA-dependent DNA polymerase.

Also provided is a method of performing a polymerase reaction. In some embodiments, the method comprises, contacting a target nucleic acid to the polypeptide as described above of elsewhere herein with an oligonucleotide primer that hybridizes to the target nucleic acid under conditions to allow the polypeptide to extend the oligonucleotide primer in a template-dependent manner, thereby performing a polymerase reaction. In some embodiments, the target nucleic acid is a RNA and the polymerase comprises one (or two) reverse transcriptases. In some embodiments, the target nucleic acid is a DNA and the polymerase comprises one (or two) DNA-dependent DNA polymerases.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

"Heterologous", when used with reference to portions of a protein, indicates that the protein comprises two or more domains that are not found in the same relationship to each other in nature. Such a protein, e.g., a fusion protein, contains two or more sequences covalently linked via a peptide bond or peptide linker sequence arranged to make a new functional protein.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra.

"Polymerase" refers to an enzyme that performs template-directed synthesis of polynucleotides. The term encompasses both the full length polypeptide and a domain that has polymerase activity.

A "template" refers to a polynucleotide sequence that comprises the polynucleotide to be amplified, optionally flanked by one or two primer hybridization sites.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a fluorophore (e.g., quantum dot) or another moiety.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, i.e.,a carbon atom that is bound to a hydrogen atom, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "promoter" refers to regions or sequence located upstream and/or downstream from the start of transcription and which are involved in recognition and binding of RNA polymerase and other proteins to initiate transcription.

A "vector" refers to a polynucleotide, which when independent of the host chromosome, is capable replication in a host organism. Preferred vectors include plasmids and typically have an origin of replication. Vectors can comprise, e.g., transcription and translation terminators, transcription and translation initiation sequences, and promoters useful for regulation of the expression of the particular nucleic acid.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Accelrys), or by manual alignment and visual inspection.

Percent sequence identity and sequence similarity is determined using the BLAST algorithm, which is described in Altschul et al., J. Mol. Biol. 215:403-410 (1990). Software for performing BLAST analyses is publicly available through the National Center for Biotechnology Information (http://www.ncbi.nlm.nih.go-v/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

DETAILED DESCRIPTION OF THE INVENTION

I. Introduction

It has been surprisingly discovered that covalent linkage of two DNA polymerases results in a polypeptide that is more thermostable and in some cases has an improved (shorter) reaction time compared to monomer polymerases. For instance, as shown in the Examples, protein fusions of the same or different reverse transcriptases result in polypeptides with more heat stability and in some cases lower reaction times than a control monomeric reverse transcriptase.

II Dimeric Proteins

Dimeric (and trimeric) DNA polymerases are provided herein. Such polypeptide can be isolated or purified or can be in complex mixtures or, for example, in cells. The polypeptides as described herein can comprise, for example, at least two and in some embodiments, three different DNA polymerases. The different DNA polymerases can be identical or they can have different sequences.

For convenience, in a dimeric polypeptide, the DNA polymerase nearest at the amino terminus of the polypeptide is referred to as the "first" DNA polymerase and the DNA polymerase nearest the carboxyl terminus is referred to as the "second" DNA polymerase. In cases where the polypeptide is a trimer, the middle DNA polymerase is the "second" and the DNA polymerase nearest the carboxyl terminus of the polypeptide is the "third" DNA polymerase. "DNA polymerase" refers to any protein (full-length as occurs in nature or a fragment or variant thereof) having DNA polymerase activity. Similarly, a "reverse transcriptase" refers to any protein (full-length as occurs in nature or a fragment or variant thereof) having reverse transcriptase activity In some embodiments one or both of the DNA polymerases in the polypeptide (or in the case of trimers, one, both, or all three) can be reverse transcriptases, i.e., an RNA-dependent DNA polymerase. In some embodiments, the polypeptides described herein comprise two reverse transcriptases. In embodiments in which the polypeptide comprises two reverse transcriptases, the reverse transcriptases can be identical in sequence or the reverse transcriptases can have different sequences. In some embodiments, the two reverse transcriptases are at least 80%, 85%, 90%, 95%, or 99% identical to each other. In other embodiments, the two reverse transcriptases are less than 70%, 80%, or 90% (e.g., 40-70, 40-80, 40-90%) identical to each other. For example, two different reverse transcriptases (or one reverse transcriptase and one DNA-dependent DNA polymerase) can be selected with complementary but different activities such that the polypeptide comprising the two reverse transcriptases (or one RT and one DNA-dependent DNA polymerase) has superior activity compared to either of the individual monomeric enzymes.

Exemplary reverse transcriptases that can be the first or second (or third) reverse transcriptase include, but are not limited to, murine leukemia virus (MLV) reverse transcriptase (Gerard and Grandgenett, Journal of Virology 15:785-797, 1975; Verma, Journal of Virology 15:843-854, 1975) or SEQ ID NO:1, feline leukemia virus (FLV) reverse transcriptase (Rho and Gallo, Cancer Lett., 10:207-221, 1980 or SEQ ID NO:1, bovine leukemia virus (BLV) (Demirhan et al., Anticancer Res., 16:2501-5, 1996; Drescher et al., Arch Geschwulstforsch., 49:569-79, 1979), Avian Myeloblastosis Virus (AMV) reverse transcriptase, Respiratory Syncytial Virus (RSV) reverse transcriptase, Equine Infectious Anemia Virus (EIAV) reverse transcriptase, Rous-associated Virus-2 (RAV2) reverse transcriptase, SUPERSCRIPT II reverse transcriptase, SUPERSCRIPT III reverse transcriptase (U.S. Pat. Nos. 8,541,219, 7,056,716, 7,078,208), THERMOSCRIPT reverse transcriptase and MMLV RNase H-reverse transcriptase.

In some one or both of the DNA polymerases (for example the reverse transcriptases) is a native polymerase. In other embodiments, one or both of the DNA polymerases (for example the reverse transcriptases) comprise one or more (e.g., 1, 2, 3, 4, 5, 6, 7, 8, 9, 10, 1-20, 1-10, 1-5, 1-2) mutation compared to the native DNA polymerase (including but not limited to SEQ ID NO:1 or SEQ ID NO:2). Exemplary mutations include, but are not limited to, mutations that reduce (e.g., reduce by at least 50, 70, or 95%) or eliminate RNase H activity (referred to as "RNase H mutations). Mutations that increase thermostability in RT can also be introduced. Exemplary mutations of this type are described in, for example, Arezi et al., *Nucleic Acids Res.* 2009 February; 37(2): 473-481.

In some embodiments, the polymerase comprises at least two (e.g., 2 or 3) DNA-dependent DNA polymerases. Exemplary DNA-dependent DNA polymerase include, but are not limited to, any of the polymerases of the five families of DNA-dependent DNA polymerases, although most will fall into families A, B and C. There is little or no structural or sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multisubunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε are implicated in nuclear replication, and a family A polymerase, polymerase γ, is used for mitochondrial DNA replication. Exemplary DNA-dependent polymerases can include, but are not limited to, Taq polymerase or iProof DNA polymerases. See, e.g., U.S. Pat. No. 8,916,352.

Optionally, the DNA polymerase(s) can be linked to a non-specific DNA binding domain. Examples of such proteins include, but are not limited to, the Archaeal small basic DNA binding proteins Sso7d and Sso7d-like proteins (see, e.g., Choli et al., Biochimica et Biophysica Acta 950:193-203, 1988; Baumann et al., Structural Biol. 1:808-819, 1994; and Gao et al, Nature Struc. Biol. 5:782-786, 1998), Archaeal HMf-like proteins (see, e.g., Starich et al., J. Molec. Biol. 255:187-203, 1996; Sandman et al., Gene 150:207-208, 1994), and PCNA homologs (see, e.g., Cann et al., J. Bacteriology 181:6591-6599, 1999; Shamoo and Steitz, Cell:99, 155-166, 1999; De Felice et al., J. Molec. Biol. 291, 47-57, 1999; and Zhang et al., Biochemistry 34:10703-10712, 1995).

Sso7d and Sso7d-like proteins, Sac7d and Sac7d-like proteins, e.g., Sac7a, Sac7b, Sac7d, and Sac7e are small (about 7,000 kd MW), basic chromosomal proteins from the hyperthermophilic archaebacteria *Sulfolobus solfataricus* and *S. acidocaldarius*, respectively. These proteins are lysine-rich and have high thermal, acid and chemical stability. They bind DNA in a sequence-independent manner and when bound, increase the $T_m$ of DNA by up to 40° C. under some conditions (McAfee, Biochemistry 34:10063-10077, 1995; Gao et al., Nat. Struct. Biol. 5(9):782-786, 1998). These proteins and their homologs are typically believed to be involved in stabilizing genomic DNA at elevated temperatures. Suitable Sso7d-like DNA binding domains for use in the invention can be modified based on their sequence homology to Sso7d. Typically, DNA binding domains that are identical to or substantially identical to a known DNA binding protein over a comparison window of about 25 amino acids, optionally about 50-100 amino acids, or the length of the entire protein, can be used in the invention. The sequence can be compared and aligned for maximum correspondence over a comparison window, or designated region as measured using one of the described comparison algorithms or by manual alignment and visual inspection. A variety of mutations in the Sso7 binding domain have been described in, e.g., US Patent Application Nos. 2005/0048530 and 2007/0141591.

The polypeptides can include additional amino acid sequences besides that of the two (or three) DNA polymerases and the linker(s). For example, in some embodiments, the polypeptide comprises additional sequence at the amino or carboxyl terminus of the polypeptide. Examples of such sequences include, but are not limited to, sequences for affinity purification of the polypeptide, or fluorescent proteins. In addition, in some embodiments, the polypeptide can include one or more fluorescent label or a fluorescent label/quencher pair.

III. Linkers

Two DNA polymerases as described can be joined via a linker by methods well known to those of skill in the art. These methods can include either chemical and recombinant means.

Chemical linking can be performed, for example, as described in Bioconjugate Techniques, Hermanson, Ed., Academic Press (1996). Joining can include, for example, derivitization for the purpose of linking the two proteins to each other, either directly or through a linking compound, by methods that are well known in the art of protein chemistry. For example, in one chemical conjugation embodiment, the means of linking the catalytic domain and the nucleic acid binding domain comprises a heterobifunctional-coupling reagent which ultimately contributes to formation of an intermolecular disulfide bond between the two moieties. Other types of coupling reagents that are useful in this capacity for the present invention are described, for example, in U.S. Pat. No. 4,545,985. Alternatively, an intermolecular disulfide may conveniently be formed between cysteines in each moiety, which occur naturally or are inserted by genetic engineering. The means of linking moieties may also use thioether linkages between heterobifunctional crosslinking reagents or specific low pH cleavable crosslinkers or specific protease cleavable linkers or other cleavable or noncleavable chemical linkages. Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Alabama. These linkers optionally have amide linkages, sulfhydryl linkages, or heterobifunctional linkages.

Linking two DNA polymerases may also comprise a peptidyl bond formed between moieties that are separately synthesized by standard peptide synthesis chemistry or recombinant means. The conjugate protein itself can also be produced using chemical methods to synthesize an amino acid sequence in whole or in part. For example, peptides can be synthesized by solid phase techniques, such as, e.g., the Merrifield solid phase synthesis method, in which amino acids are sequentially added to a growing chain of amino acids (see, Merrifield (1963) J. Am. Chem. Soc., 85:2149-2146). Equipment for automated synthesis of polypeptides is commercially available from suppliers such as PE Corp. (Foster City, Calif.), and may generally be operated according to the manufacturer's instructions. The synthesized peptides can then be cleaved from the resin, and purified, e.g., by preparative high performance liquid chromatography (see Creighton, Proteins Structures and Molecular Principles, 50-60 (1983)). The composition of the synthetic polypeptides or of subfragments of the polypeptide, may be confirmed by amino acid analysis or sequencing (e.g., the Edman degradation procedure; see Creighton, Proteins, Structures and Molecular Principles, pp. 34-49 (1983)).

In addition, nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxy-proline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, N-methyl amino acids, and amino acid analogs in general. Furthermore, the amino acid can be D (dextrorotary) or L (levorotary).

In some embodiments, two DNA polymerase are joined via a linking group. The linking group can be a chemical crosslinking agent, including, for example, succinimidyl-(N-maleimidomethyl)-cyclohexane-1-carboxylate (SMCC). The linking group can also be an additional amino acid sequence(s), including, for example, a polyalanine, polyglycine or similarly, linking group.

Alternatively, in some embodiments, the coding sequences of each DNA polymerase in the polypeptide are directly joined and expressed as a fusion protein. Alternatively, an amino acid linker sequence may also be encoded in the polypeptide coding sequence and employed to separate the first and second polypeptide components by a distance sufficient to ensure that each polypeptide folds into its secondary and tertiary structures. Such an amino acid linker sequence is incorporated into the fusion protein using recombinant techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Typical peptide linker sequences contain Gly, Ser, Val and Thr residues. Other near neutral amino acids, such as Ala can also be used in the linker sequence. Amino acid sequences which may be usefully employed as linkers include those disclosed in Maratea et al. (1985) Gene 40:39-46; Murphy et al. (1986) Proc. Natl. Acad. Sci. USA 83:8258-8262; U.S. Pat. Nos. 4,935,233 and 4,751,180. The linker sequence may generally be from 1 to about 50 amino acids in length, e.g., 3, 4, 6, or 10 amino acids in length, but can be 100 or 200 amino acids in length. Linker sequences may not be required when the second polypeptides have non-essential N-terminal amino acid regions that can be used to separate the functional domains and prevent steric interference.

IV. Expression and Purification

Nucleic acids encoding the DNA polymerases can be obtained using routine techniques in the field of recombinant genetics. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999). Such nucleic acids may also be obtained through in vitro amplification methods such as those described herein and in Berger, Sambrook, and Ausubel, as well as Mullis et al., (1987) U.S. Pat. No. 4,683,202; PCR Protocols A Guide to Methods and Applications (Innis et al., eds) Academic Press Inc. San Diego, Calif. (1990) (Innis); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Natl. Acad. Sci. USA 87, 1874; Lomell et al. (1989) J. Clin. Chem., 35: 1826; Landegren et al., (1988) Science 241: 1077-1080; Van Brunt (1990) Biotechnology 8: 291-294; Wu and Wallace (1989) Gene 4: 560; and Barringer et al. (1990) Gene 89: 117, each of which is incorporated by reference in its entirety for all purposes and in particular for all teachings related to amplification methods.

One of skill will recognize that modifications can additionally be made to the DNA polymerases without diminishing their biological activity. Some modifications may be made to facilitate the cloning, expression, or incorporation of a domain into a fusion protein. Such modifications are well known to those of skill in the art and include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences.

The fusion polypeptides as described herein can be expressed in a variety of host cells, including E. coli, other bacterial hosts, yeasts, filamentous fungi, and various higher eukaryotic cells such as the COS, CHO and HeLa cells lines and myeloma cell lines. Techniques for gene expression in microorganisms are described in, for example, Smith, Gene Expression in Recombinant Microorganisms (Bioprocess Technology, Vol. 22), Marcel Dekker, 1994. Examples of bacteria that are useful for expression include, but are not limited to, *Escherichia, Enterobacter, Azotobacter, Erwinia, Bacillus, Pseudomonas, Klebsielia, Proteus, Salmonella, Serratia, Shigella, Rhizobia, Vitreoscilla*, and *Paracoccus*. Filamentous fungi that are useful as expression hosts include, for example, the following genera: *Aspergillus, Trichoderma, Neurospora, Penicillium, Cephalosporium, Achlya, Podospora, Mucor, Cochliobolus*, and *Pyricularia*. See, e.g., U.S. Pat. No. 5,679,543 and Stahl and Tudzynski, Eds., Molecular Biology in Filamentous Fungi, John Wiley & Sons, 1992. Synthesis of heterologous proteins in yeast is well known and described in the literature. Methods in Yeast Genetics, Sherman, F., et al., Cold Spring Harbor Laboratory, (1982) is a well-recognized work describing the various methods available to produce the enzymes in yeast.

There are many expression systems for producing the polypeptides that are well known to those of ordinary skill in the art. (See, e.g., Gene Expression Systems, Fernandex and Hoeffler, Eds. Academic Press, 1999; Sambrook and Russell, supra; and Ausubel et al, supra.) Typically, the polynucleotide that encodes the polypeptide is placed under the control of a promoter that is functional in the desired host cell. Many different promoters are available and known to one of skill in the art, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the nucleic acids that encode the joined polypeptides are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., Nature (1977) 198: 1056), the tryptophan (trp) promoter system (Goeddel et al., Nucleic Acids Res. (1980) 8: 4057), the tac promoter (DeBoer, et al., Proc. Natl. Acad. Sci. U.S.A. (1983) 80:21-25); and the lambda-derived PL promoter and N-gene ribosome binding site (Shimatake et al., Nature (1981) 292: 128). The particular promoter system is not critical; any available promoter that functions in prokaryotes and provides the desired level of activity can be used. Standard bacterial expression vectors include plasmids such as pBR322-based plasmids, e.g., pBLUE-SCRIPT™, pSKF, pET23D, lambda-phage derived vectors, and fusion expression systems such as GST and LacZ. Epitope tags can also be added to recombinant proteins to provide convenient methods of isolation, e.g., c-myc, HAtag, 6-His tag, maltose binding protein, VSV-G tag, anti-DYKDDDDK tag, or any such tag, a large number of which are well known to those of skill in the art.

For expression in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* sp. in addition to *E. coli*. These and other suitable bacterial promoters are well known in the art and are described, e.g., in Sambrook et al. and Ausubel et al. Bacterial expression systems for expressing the proteins of the invention are available in, e.g., *E. coli, Bacillus* sp., and *Salmonella* (Palva et al., Gene 22:229-235 (1983); Mosbach et al., Nature 302:543-545 (1983). Kits for such expression systems are commercially available.

Eukaryotic expression systems for mammalian cells, yeast, and insect cells are well known in the art and are also commercially available. In yeast, vectors include Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Either constitutive or regulated promoters can be used. Regulated promoters can be advantageous because the host cells can be grown to high densities before expression of the fusion polypeptides is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals.

For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) Gene 25: 167; de Boer et al. (1983) Proc. Nat'l. Acad. Sci. USA 80: 21), and the bacteriophage T7 promoter (Studier et al. (1986) J. Mol. Biol.; Tabor et al. (1985) Proc. Nat'l Acad. Sci. USA 82: 1074-8). These promoters and their use are also discussed in Sambrook et al., supra.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), J. Biol. Chem. 263: 16297-16302.

The construction of polynucleotide constructs generally requires the use of vectors able to replicate in bacteria. Such vectors are commonly used in the art. A plethora of kits are commercially available for the purification of plasmids from bacteria (for example, EasyPrep™, FlexiPrep™, from Pharmacia Biotech; StrataClean™, from Stratagene; and, QIAexpress® Expression System, Qiagen). The isolated and purified plasmids can then be further manipulated to produce other plasmids, and used to transform cells.

The polypeptides described herein can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al., Bio/Technology (1984) 2: 800; Schoner et al., Bio/Technology (1985) 3: 151). Polypeptides can be expressed in a variety of host cells, including *E. coli*, other bacterial hosts, yeast, and various higher eukaryotic cells such as the COS, CHO and HeLa cells lines and myeloma cell lines. The host cells can be mammalian cells, insect cells, or microorganisms, such as, for example, yeast cells, bacterial cells, or fungal cells.

Once expressed, the polypeptides can be purified according to standard procedures of the art, including ammonium sulfate precipitation, affinity columns, column chromatography, gel electrophoresis and the like (see, generally, R. Scopes, Protein Purification, Springer-Verlag, N.Y. (1982), Deutscher, Methods in Enzymology Vol. 182: Guide to Protein Purification., Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

To facilitate purification of the polypeptides, the nucleic acids that encode the polypeptides can also include a coding sequence for an epitope or "tag" for which an affinity binding reagent is available. Examples of suitable epitopes include the myc and V-5 reporter genes; expression vectors useful for recombinant production of fusion polypeptides having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the fusion proteins of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, N.Y.; commercially available from Qiagen (Santa Clarita, Calif.)).

One of skill in the art would recognize that after biological expression or purification, the polymerase peptide (s) may possess a conformation substantially different than the native conformations of the constituent polypeptides. In this case, it may be necessary or desirable to denature and reduce the polypeptide and then to cause the polypeptide to re-fold into the preferred conformation. Methods of reducing and denaturing proteins and inducing re-folding are well known to those of skill in the art (See, Debinski et al. (1993) J. Biol. Chem. 268: 14065-14070; Kreitman and Pastan (1993) Bioconjug. Chem. 4: 581-585; and Buchner et al. (1992) Anal. Biochem. 205: 263-270). Debinski et al., for example, describe the denaturation and reduction of inclusion body proteins in guanidine-DTE. The protein is then refolded in a redox buffer containing oxidized glutathione and L-arginine.

V. Methods of Use

Reverse transcription (RT) is an amplification method that copies RNA into DNA. RT reactions can be performed with reaction mixtures as described herein. For example, the invention provides for reverse transcribing one or more RNA (including for example, all RNA in a cell, e.g., to make a cDNA library) under conditions to allow for reverse transcription and generation of a first and optionally second strand cDNA. The RT reaction can be primed with a random primer, an oligo dT, or an RNA-specific primer. Components and conditions for RT reactions are generally known.

If desired, the reactions can further comprise RT-PCR. Standard techniques for performing PCR assays are known in the art (PCR Technology: Principles and Applications for DNA Amplification (Erlich, ed., 1989); PCR Protocols: A Guide to Methods and Applications (Innis, Gelfland, Sninsky, &, White, eds., 1990); Mattila et al., *Nucleic Acids Res.* 19: 4967 (1991); Eckert & Kunkel, PCR Methods and Applications 1: 17 (1991); Wallace et al., Ligase Chain Reaction, in Technologies for Detection of DNA Damage and Mutations, pp. 307-322 (Pfiefer, ed., 1996)). RT and PCR reactions are often used in the same assay and are referred to as RT-PCR. RT-PCR combines reverse transcription of RNA into DNA and subsequent DNA amplification reactions in a single reaction. Optimal reverse transcription, hybridization, and amplification conditions will vary depending upon the sequence composition and length(s) of the primers and target(s) employed, and the experimental method selected by the practitioner. Various guidelines may be used to select appropriate primer sequences and hybridization conditions (see, e.g., Sambrook et al., Molecular Cloning: A Laboratory Manual (2nd ed.) (1989); Ausubel, F. M. et al., eds. (1999) Short Protocols in Molecular Biology, 4th edition, John Wiley & Sons); Ausubel, F. M. et al., eds. (1999-2010) Current Protocols in Molecular Biology, John Wiley & Sons).

The practice of the present invention can employ conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999-2010) Current Protocols in Molecular Biology, John Wiley & Sons; Ream et al., eds. (1998) Molecular Biology Techniques: An Intensive Laboratory Course, Academic Press; Newton, C. R., and Graham, A., eds. (1997) PCR (Introduction to Biotechniques Series), 2nd ed., Springer Verlag; Sambrook et al., Molecular Cloning: A Laboratory Manual (2nd ed.) (1989).

An advantage of the reaction mixtures of the invention is that the reaction mixtures allow for use of a reverse transcriptase in an RT or DNA-dependent DNA polymerase reaction at a higher temperature than would otherwise be possible. Thus, in embodiments, the dimeric or trimeric enzymes described herein can be used at, 37° or 42° C., or a temperature greater than 42° C., for example, between 43°-55°, 45°-56°, 45°-65° C., etc. Higher temperature RT reactions are particularly helpful in situations where the template RNA forms secondary structure at normal RT temperatures (e.g., 37° or 42° C.) that partially or completely inhibit reverse transcription.

In cases in which the polypeptide as described herein comprises one or two DNA-dependent DNA polymerases, the polypeptide can be used in a primer extension reaction in a template-dependent manner. In some embodiments, the primer extension reaction is an amplification reaction. In some embodiments, the amplification reaction is monitored in real-time and optionally is used to quantify the initial amount of target nucleic acid.

Such amplification reactions include without limitation polymerase chain reaction (PCR), DNA ligase chain reaction (LCR), and RNA transcription-based (such as TAS and 3SR) amplification reactions as well as others known to those of skill in the art. Polymerase chain reactions that can be conducted using the compositions described herein include without limitation reverse-transcription PCR (rt-PCR) and quantitative PCR (qPCR).

In some embodiments, dye-based qPCR detection methods are used to monitor amplification reactions utilizing components of the invention. Such detection methods generally rely on monitoring the increase in fluorescence signal due to the binding of DNA-binding dye to the amplified DNA. For example, SYBR Green I, a commonly used fluorescent DNA binding dye, binds all double-stranded DNA and detection is monitored by measuring the increase in fluorescence throughout the cycle. SYBR Green I has an excitation and emission maxima of 494 nm and 521 nm, respectively.

In other embodiments, probe-based qPCR detection methods are used to monitor amplification reactions utilizing components of the invention. Such detection methods generally rely on the sequence-specific detection of a desired PCR product. Unlike dye-based qPCR methods that detect all double-stranded DNA, probe-based qPCR utilizes a fluorescent-labeled target-specific probe, which detects specific sequences in the amplified DNA.

VI. Reaction Mixtures

Reaction mixtures comprising the polypeptides described herein are provided. The reaction mixtures can comprise, for example, a target nucleic acid, e.g., an RNA target where reverse transcription is to take place, or DNA where a DNA-dependent polymerase reaction is to take place. The reaction mixtures can comprise appropriate nucleotides (e.g., deoxynucleotides (dNTPs) or dideoxynucleotides) and in some embodiments, at least one buffer. Exemplary buffers can include, for example and without limitation, Tris, HEPES, ACES, PIPES, MOPSO, BES, MOPS, TES, TAPSO, POPSO, BICINE, TAPS, or AMPSO. The reaction mixtures can optionally comprise one or more oligonucleotides that function as a primer for template-dependent nucleic acid extension, one or more oligonucleotides that function as a probe (e.g., linked to a label such as a quencher, fluorescent dye, etc.), and/or a double stranded DNA binding dye (e.g., SYBRGREEN). In some embodiments, the reaction mixture will further comprises a separate DNA-dependent DNA polymerase. In some embodiments, the reaction mixture will further comprises magnesium (Mg++).

VII. Kits

In one aspect, kits for conducting nucleic acid extension (and optionally cyclic amplification, e.g., such as PCR) reactions are provided. In some embodiments, such kits include polymerases, and optionally dNTPs, and at least one buffer. Such kits may also include stabilizers and other additives (e.g., heparin and/or sarcosine) to increase the efficiency of the amplification reactions. Such kits may also include one or more primers as well as instructions for conducting nucleic acid amplification reactions using the components of the kits. In some embodiments, the kits will further comprises a separate DNA-dependent DNA polymerase.

EXAMPLES

Methods and Materials
Cloning and Expression:
  MLV reverse transcriptase gene was cloned into the pET28 vector by PCR to amplify the gene and followed by restriction enzyme digestion and ligation. The expression construct contained a gene encoding a histidine tag that was fused to the N-terminus of the reverse transcriptase. Two MLV genes were linked together through a linker sequence that contains restriction sites HindIII, NheI, and SacI.

The expression plasmid was transformed into *E. coli* BL21/DE3 cells. The cells containing the expression plasmid were inoculated for overnight culturing in LB medium, 1/100 of the culture was used to seed a fresh LB medium the following morning. Cells were grown at 16 C. After cell density reached OD600=0.6 to 0.8, IPTG was added to 0.1mM to induce the protein expression. Cells were collected 15 hrs after induction.

```
MLV RT aa sequence
                                                       SEQ ID NO:1:
TLNIEDEHRLHETSKEPDVSLGSTWLSDFPQAWAETGGMGLAVRQAPLIEPLKATSTPVSI

KQYPMSQEARLGIKPHIQRLLDQGILVPCQSPWNTPLLPVKKPGTNDYRPVQDLREVNK

RVEDIHPTVPNPYNLLSGLPPSHQWYTVLDLKDAFFCLRLHPTSQPLFAFEWRDPEMGIS

GQLTWTRLPQGFKNSPTLFDEALBRDLADFRIQHPDLELLQYVDDLLLAATSELDCQQG

TRALLQTLGNLGYRASAKKAQICQKQVKYLGYLLKEGQRWLTEARKETVMGQPTPKT

PRQLREFLGTAGFCRLWIPGFAEMAAPLYPLTKTGTLFNWGPDQQKAYQEIKQALLTAP

ALGLPDLTKPFELFVDEKQGYAKGVLTQKLGPWRRPVAYLSKKLDPVAAGWPPCLRM

VAAIAVLTKDAGKLTMGQPLVILAPHAVEALVKQPPDRWLSNARMTHYQALLLDTDR

VQFGPVVALNPATLLPLPEEGLQHNCLDILAEAHGTRPDLTDQPLPDADHTWYTDGSSL

LQEGQRKAGAAVTTETEVIWAKALPAGTSAQRAELIALTQALKMAEGKKLNVYTDSRY

AFATAHIHGEIYRRRGLLTSEGKEIKNKDEILALLKALFLPKRLSIIHCPGHQKGHSAEAR

GNRMADQAARKAAITETPDTSTLL

FLV RT aa sequence
                                                       SEQ ID NO:2:
TLQLEEEYRLFEPESTQKQEMDIWLKNFPQAWAETGGMGMAHCQAPVLIQLKATATPIS

IRQYPMPHEAYQGIKPHIRRMLDQGILKPCQSPWNTPLLPVKKPGTKDYRPVQDLREVN

KRVEDIHPTVPNPYNLLSTLPPSHPWYTVLDLKDAFFCLRLHSESQLLFAFEWRDPEIGLS

GQLTWTRLPQGFKNSPTLFDEALHSDLADFRVRYPALVLLQYVDDLLLAAATRTECLEG

TKALLETLGNKGYRASAKKAQICLQEVTYLGYSLKDGQRWLTKARKEAILSIPVPKNPR

QVREFLGTAGYCRLWIPGFAELAAPLYPLTRPGTLFQWGTEQQLAFENIRKALLSSPALG

LPDITKPFELFIDENSGFAKGVLVQKLGPWKRPVAYLSKKLDTVASGWPPCLRMVAAIA

ILVKDAGKLTLGQPLTILTSHPVEALVRQPPNKWLSNARMTHYQAMLLDAERVHFGPT

VSLNPATLLPLPSGKPPRLSPDLAETMAQTDLTDQPLPDADLTWYTDGSSFIRNGERKAG

AAVTTESEVIWAASLPPGTSAQRAELIALTQALKMAKGKKLTVYTDSRYAFATAHVHG

EIYRRRGLLTSEGKEIKNKNEILALLEALFLPKRLSIIHCPGHQKGDSPQAKGNRLADDTA

KKAATETQSSLTIL

MM Dimeric RT sequence(linker underlined)
                                                       SEQ ID NO:3:
EFTLNIEDEHRLITETSKEPDVSLGSTWLSDFPQAWAETGGMGLAVRQAPLIIPLKATSTP

VSIKQYPMSQEARLGIKPHIQRLLDQGILVPCQSPWNTPLLPVKKPGTNDYRPVQDLREV

NKRVEDIFIPTVPNPYNLLSGLPPSHQWYTVLDLKDAFFCLRLHPTSQPLFAFEWRDPEM
```

GISGQLTWTRLPQGFKNSPTLFDEALIIRDLADFRIQHPDLILLQYVDDLLLAATSELDCQ

QGTRALLQTLGNLGYRASAKKAQICQKQVKYLGYLLKEGQRWLTEARKETVMGQPTP

KTPRQLREFLGTAGFCRLWIPGFAEMAAPLYPLTKTGTLFNVVGPDQQKAYQEIKQALLT

APALGLPDLTKPFELFVDEKQGYAKGVLTQKLGPWRRPVAYLSKKLDPVAAGWPPCLR

MVAAIAVLTKDAGKLTMGQPLVILAPHAVEALVKQPPDRWLSNARMTHYQALLLDTD

RVQFGPVVALNPATLLPLPEEGLQHNCLDILAEAHGTRPDLTDQPLPDADHTWYTDGSS

LLQEGQRKAGAAVTTETEVIWAKALPAGTSAQRAELIALTQALKMAEGKKLNVYTDSR

YAFATAHIHGEIYRRGLLTSEGKEIKNKDEILALLKALFLPKRLSIEFICPGHQKGHSAEA

RGNRMADQAARKAAITETPDTSTLL<u>SSSASKL</u>EFTLNIEDEHRLHETSKEPDVSLGSTWL

SDFPQAWAETGGMGLAVRQAPLLIPLKATSTPVSIKQYPMSQEARLGIKPHIQRLLDQGIL

VPCQSPWNTPLLPVKKPGTNDYRPVQDLREVNKRVEDIHPTVPNPYNLLSGLPPSHQWY

TVLDLKDAFFCLRLHPTSQPLFAFEWRDPEMGISGQLTWTRLPQGFKNSPTLFDEALHR

DLADFRIQHPDLILLQYVDDLLLAATSELDCQQGTRALLQTLGNLGYRASAKKAQICQK

QVKYLGYLLKEGQRWLTEARKETVMGQPTPKTPRQLREFLGTAGFCRLWIPGFAEMAA

PLYPLTKTGTLFNWGPDQQKAYQEIKQALLTAPALGLPDLTKPFELFVDEKQGYAKGVL

TQKLGPWRRPVAYLSKKLDPVAAGWPPCLRMVAAIAVLTKDAGKLTMGQPLVILAPH

AVEALVKQPPDRWLSNARMTHYQALLLDTDRVQFGPVVALNPATLLPLPEEGLQHNCL

DILAEAHGTRPDLTDQPLPDADHTWYTDGSSLLQEGQRKAGAAVTTETEVIWAKALPA

GTSAQRAELIALTQALKMAEGKKLNVYTDSRYAFATAHIHGEIYRRGLLTSEGKEIKN

KDEILALLKALFLPICRLSIIHCPGHQKGHSAEARGNRMADQAARKAAITETPDTSTLLSS

SAS

MNM Dimeric RT sequence (linker underlined)

SEQ ID NO:4:
EFTLNIEDEHRLHETSKEPDVSLGSTWLSDFPQAWAETGGMGLAVRQAPLIIPLKATSTP

VSIKQYPMSQEARLGIKPHIQRLLDQGILVPCQSPWNTPLLP'VKKPGTNDYRPVQDLREV

NKRVEDIHPTVPNPYNLLSGLPPSHQWYTVLDLKDAFFCLRLHPTSQPLFAFEWRDPEM

GISGQLTWTRLPQGFKNSPTLFDEALHRDLADFRIQHPDLILLQYVDDLLLAATSELDCQ

QGTRALLQTLGNLGYRASAKKAQICQKQVKYLGYLLKEGQRWLTEARKETVMGQPTP

KTPRQLREFLGTAGFCRLWIPGFAEMAAPLYPLTKTGTLFNWGPDQQKAYQEIKQALLT

APALGLPDLTKPFELFVDEKQGYAKGVLTQKLGPWRRPVAYLSKKLDPVAAGWPPCLR

MVAAIAVLTKDAGKLTMGQPLVILAPHAVEALVKQPPDRWLSNARMTHYQALLLDTD

RVQFGPVVALNPATLLPLPEEGLQHNCLDILAEAHGTRPDLTDQPLPDADHTWYTNGSS

LLQEGQRKAGAAVTTETEVIWAKALPAGTSAQRAELIALTQALKMAEGKKLNVYTDSR

YAFATAHIHGEIYRRGLLTSEGKEIKNKDEILALLKALFLPKRLSIMCPGHQKGHSAEA

RGNRMADQAARKAAITETPDTSTLL<u>SSSASKL</u>EFTLNIEDEHRLHETSKEPDVSLGSTWL

SDFPQAWAETGGMGLAVRQAPLIIPLKATSTPVSIKQYPMSQEARLGIKPHIQRLLDQGIL

VPCQSPWNTPLLPVKKPGTNDYRPVQDLREVNKRVEDIHPTVPNPYNLLSGLPPSHQWY

TVLDLKDAFFCLRLHPTSQPLFAFEWRDPEMGISGQLTWTRLPQGFKNSPTLFDEALHR

DLADFRIQHPDLILLQYVDDLLLAATSELDCQQGTRALLQTLGNLGYRASAKKAQICQK

QVKYLGYLLKEGQRWLTEARKETVMGQPTPKTPRQLREFLGTAGFCRLWIPGFAEMAA

-continued

PLYPLTKTGTLFNWGPDQQKAYQEIKQALLTAPALGLPDLTKPFELFVDEKQGYAKGVL

TQKLGPWRRPVAYLSKKLDPVAAGWPPCLRMVAAIAVLTKDAGKLTMGQPLVILAPH

AVEALVKQPPDRWLSNARMTHYQALLLDTDRVQFGPVVALNPATLLPLPEEGLQHNCL

DILAEAHGTRFIDLTDQPLPDADHTWYTDGSSLLQEGQRKAGAAVTTETEVIWAKALPA

GTSAQRAELIALTQALKMAEGKKLNVYTDSRYAFATABIFIGEIYRRRGLLTSEGKEIKN

KDEILALLKALFLPKRLSMCPGHQKGHSAEARGNRMADQAARKAAITETPDTSTLLSS

SAS

MNMN Dimeric RT sequence(linker underlined)

SEQ ID NO:5:
EFTLNIEDEHRLHETSKEPDVSLGSTWLSDFPQAWAETGGMGLAVRQAPLIIPLKATSTP

VSIKQYPMSQEARLGIKPREQRLLDQGILVPCQSPWNTPLLPVKKPGTNDYRPVQDLREV

NKRVEDEHPTVPNPYNLLSGLPPSHQWYTVLDLKDAFFCLRLHPTSQPLFAFEWRDPEM

GISGQLTWTRLPQGFKNSPTLFDEALHRDLADFRIQHPDLILLQYVDDLLLAATSELDCQ

QGTRALLQTLGNLGYRASAKKAQICQKQVKYLGYLLKEGQRWLTEARKETVMGQPTP

KTPRQLREFLGTAGFCRLWIPGFAEMAAPLYPLTKTGTLFNWGPDQQKAYQEIKQALLT

APALGLPDLTKPFELFVDEKQGYAKGVLTQKLGPWRRPVAYLSKKLDPVAAGWPPCLR

MVAAIAVLTKDAGKLTMGQPLVILAPHAVEALVKQPPDRWLSNARMTHYQALLLDTD

RVQFGPVVALNPATLLPLPEEGLQHNCLDILAEAHGTRPDLTDQPLPDADHTWYTNGSS

LLQEGQRKAGAAVTTETEVIWAKALPAGTSAQRAELIALTQALKMAEGKKLNVYTDSR

YAFATAHIHGEIYRRRGLLTSEGKEIKNKDEILALLKALFLPKRLSIIHCPGHQKGHSAEA

RGNRMADQAARKAAITETPDTSTLLSSSASKLEFTLNIEDEHRLHETSKEPDVSLGSTWL

SDFPQAWAETGGMGLAVRQAPLIIPLKATSTPVSIKQYPMSQEARLGIKPHIQRLLDQGIL

VPCQSPWNTPLLPVKKPGTNDYRPVQDLREVNKRVEDIHPTVPNPYNLLSGLPPSHQWY

TVLDLKDAFFCLRLHPTSQPLFAFEWRDPEMGISGQLTWTRLPQGFKNSPTLFDEALHR

DLADFRIQHPDIALLQYVDDLLLAATSELDCQQGTRALLQTLGNLGYRASAKKAQICQK

QVKYLGYLLKEGQRWLTEARKETVMGQPTPKTPRQLREFLGTAGFCRLWIPGFAEMAA

PLYPLTKTGTLFNWGPDQQKAYQEIKQALLTAPALGLPDLTKPFELFVDEKQGYAKGVL

TQKLGPWRRPVAYLSKKLDPVAAGWPPCLRMVAAIAVLTKDAGKLTMGQPLVILAPH

AVEALVKQPPDRWLSNARMTHYQALLLDTDRVQFGPVVALNPATLLPLPEEGLQHNCL

DILAEAHGTRPDLTDQPLPDADHTWYTNGSSLLQEGQRKAGAAVTTETEVIWAKALPA

GTSAQRAELIALTQALKMAEGKKLNVYTDSRYAFATAHIHGEIYRRRGLLTSEGKEIKN

KDEILALLKALFLPKRLSEIBCPGHQKGHSAEARGNRMADQAARKAAITETPDTSTLLSS

SAS

FF Dimeric RT sequence(linker underlined)

SEQ ID NO:6:
EFTLQLEEEYRLFEPESTQKQEMDIWLKNFPQAWAETGGMGMAHCQAPVLIQLKATAT

PISIRQYPMPHEAYQGIKPHIRRMLDQGILKPCQSPWNTPLLPVKKPGTKDYRPVQDLRE

VNKRVEDEHPTVPNPYNLLSTLPPSHPWYTVLDLKDAFFCLRLHSESQLLFAFEWRDPEI

GLSGQLTWTRLPQGFKNSPTLFDEALHSDLADFRVRYPALVLLQYVDDLLLAAATRTEC

LEGTKALLETLGNKGYRASAKKAQICLQEVTYLGYSLKDGQRWLTKARKEAILSEPVPK

NPRQVREFLGTAGYCRLWIPGFAELAAPLYPLTRPGTLFQWGTEQQLAFENIRKALLSSP
ALGLPDITKPFELFIDENSGFAKGVLVQKLGPWKRPVAYLSKKLDTVASGWPPCLRMVA
AIAILVKDAGKLTLGQPLTILTSHPVEALVRQPPNKWLSNARMTHYQAMLLDAERVHFG
PTVSLNPATLLPLPSGKPPRLSPDLAETMAQTDLTDQPLPDADLTWYTDGSSFIRNGERK
AGAAVTTESEVIWAASLPPGTSAQRAELIALTQALKMAKGKKLTVYTDSRYAFATAHV
HGEIYRRGLLTSEGKEEKNKNEILALLEALFLPKRLSIIHCPGHQKGDSPQAKGNRLADD
TAKKAATETQSSLTILSSSASKLEFTLQLEEEYRLFEPESTQKQEMDIWLKNFPQAWAET

GGMGMAHCQAPVLIQLKATATPISIRQYPMPHEAYQGIKPHERRMLDQGILKPCQSPWN
TPLLPVKKPGTKDYRPVQDLREVNKRVEDIHPTVPNPYNLLSTLPPSHPWYTVLDLKDA
FFCLRLHSESQLLFAFEWRDPEIGLSGQLTWTRLPQGFKNSPTLFDEALHSDLADFRVRY
PALVLLQYVDDLLLAAATRTECLEGTKALLETLGNKGYRASAKKAQICLQEVTYLGYS
LKDGQRWLTKARKEAILSIPVPKNPRQVREFLGTAGYCRLWIPGFAELAAPLYPLTRPGT
LFQWGTEQQLAFENIRKALLSSPALGLPDITKPFELFIDENSGFAKGVLVQKLGPWKRPV
AYLSKKLDTVASGWPPCLRMVAAIAILVKDAGKLTLGQPLTILTSHPVEALVRQPPNKW
LSNARMTHYQAMLLDAERVHFGPTVSLNPATLLPLPSGKPPRLSPDLAETMAQTDLTDQ
PLPDADLTWYTDGSSFIRNGERKAGAAVTTESEVIWAASLPPGTSAQRAELIALTQALK
MAKGKKLTVYTDSRYAFATAHVHGEIYRRGLLTSEGKEIKNKNEILALLEALFLPKRL
SIEFICPGHQKGDSPQAKGNRLADDTAKKAATETQSSLTILSSSAS

FNF Dimeric RT sequence(linker underlined)

SEQ ID NO:7:
EFTLQLEEEYRLFEPESTQKQEMDIWLKNFPQAWAETGGMGMAHCQAPVLIQLKATAT
PISIRQYPMPHEAYQGIKPHIRRMLDQGILKPCQSPWNTPLLPVKKPGTKDYRPVQDLRE
VNKRVEDIEPTVPNPYNLLSTLPPSHPWYTVLDLKDAFFCLRLHSESQLLFAFEWRDPEI
GLSGQLTWTRLPQGFKNSPTLFDEALHSDLADFRVRYPALVLLQYVDDLLLAAATRTEC
LEGTKALLETLGNKGYRASAKKAQICLQEVTYLGYSLKDGQRWLTKARKEAILSIPVPK
NPRQVREFLGTAGYCRLWIPGFAELAAPLYPLTRPGTLFQWGTEQQLAFENIRKALLSSP
ALGLPDITKPFELF+DENSGFAKGVLVQKLGPWKRPVAYLSKKLDTVASGWPPCLRMVA
AIAILVKDAGKLTLGQPLTILTSHPVEALVRQPPNKWLSNARMTHYQAMLLDAERVHFG
PTVSLNPATLLPLPSGKPPRLSPDLAETMAQTDLTDQPLPDADLTWYTNGSSFIRNGERK
AGAAVTTESEVIWAASLPPGTSAQRAELIALTQALKMAKGKKLTVYTDSRYAFATAHV
HGEIYRRGLLTSEGKEIKNKNEILALLEALFLPKRLSIIHCPGHQKGDSPQAKGNRLADD
TAKKAATETQSSLTILSSSASKLEFTLQLEEEYRLFEPESTQKQEMDIWLKNFPQAWAET

GGMGMAHCQAPVLIQLKATATPISIRQYPMPHEAYQGIKPHIRRMLDQGILKPCQSPWN
TPLLPVKKPGTKDYRPVQDLREVNKRVEDIHPTVPNPYNLLSTLPPSHPWYTVLDLKDA
FFCLRLHSESQLLFAFEWRDPEIGLSGQLTWTRLPQGFKNSPTLFDEALHSDLADFRVRY
PALVLLQY'VDDLLLAAATRTECLEGTKALLETLGNKGYRASAKKAQICLQEVTYLGYS
LKDGQRWLTKARKEAILSIPVPKNPRQVREFLGTAGYCRLWIPGFAELAAPLYPLTRPGT
LFQWGTEQQLAFENIRKALLSSPALGLPDITKPFELFIDENSGFAKGVLVQKLGPWKRPV
AYLSKKLDTVASGWPPCLRMVAAIAILVKDAGKLTLGQPLTILTSHPVEALVRQPPNKW
LSNARMTHYQAMLLDAERVHFGPTVSLNPATLLPLPSGKPPRLSPDLAETMAQTDLTDQ

PLPDADLTWYTDGSSFIRNGERKAGAAVTTESEVIWAASLPPGTSAQRAELIALTQALK

MAKGKKLTVYTDSRYAFATAHVHGEIYRRRGLLTSEGKEIKNKNEILALLEALFLPICRL

SHHCPGHQKGDSPQAKGNRLADDTAKKAATETQSSLTILSSSAS

FNFN Dimeric RT sequence(linker underlined)

SEQ ID NO:8:
EFTLQLEEEYRLFEPESTQKQEMDIWLKNFPQAWAETGGMGMAHCQAPVLIQLKATAT

PISIRQYPMPHEAYQGIKPHIRRMLDQGILKPCQSPWNTPLLPVKKPGTKDYRPVQDLRE

VNKRVEDIFIF'TVPNPYNLLSTLPPSHPWYTVLDLKDAFFCLRLHSESQLLFAFEWRDPEI

GLSGQLTWTRLPQGFKNSPTLFDEALHSDLADFRVRYPALVLLQYVDDLLLAAATRTEC

LEGTKALLETLGNKGYRASAKKAQICLQEVTYLGYSLKDGQRWLTKARKEAILSIPVPK

NPRQVREFLGTAGYCRLWIPGFAELAAPLYPLTRPGTLFQWGTEQQLAFENIRKALLSSP

ALGLPDITKPFELFIDENSGFAKGVLVQKLGPWKRPVAYLSKKLDTVASGWPPCLRMVA

AIAILVKDAGKLTLGQPLTILTSHPVEALVRQPPNKWLSNARMTHYQAMLLDAERVHFG

PTVSLNPATLLPLPSGKPPRLSPDLAETMAQTDLTDQPLPDADLTWYTNGSSFIRNGERK

AGAAVTTESEVIWAASLPPGTSAQRAELIALTQALKMAKGKKLTVYTDSRYAFATAHV

HGEIYRRRGLLTSEGKEIKNKNEILALLEALFLPKRLSIIHCPGHQKGDSPQAKGNRLADD

TAKKAATETQSSLTIL<u>SSSASKL</u>EFTLQLEEEYRLFEPESTQKQEMDIWLKNFPQAWAET

GGMGMAHCQAPVLIQLKATATPISIRQYPMPHEAYQGIKPHIRRMLDQGILKPCQSPWN

TPLLPVKKPGTKDYRPVQDLREVNKRVEDIHPTVPNPYNLLSTLPPSHPWYT'VLDLKDA

FFCLRLHSESQLLFAFEWRDPEIGLSGQLTWTRLPQGFKNSPTLFDEALHSDLADFRVRY

PALVLLQYVDDLLLAAATRTECLEGTKALLETLGNKGYRASAKKAQICLQEVTYLGYS

LKDGQRWLTKARKEAILSIPVPKNPRQVREFLGTAGYCRLWIPGFAELAAPLYPLTRPGT

LFQWGTEQQLAFENIRKALLSSPALGLPDITKPFELFIDENSGFAKGVLVQKLGPWKRPV

AYLSKKLDTVASGWPPCLRMVAAIAILVKDAGKLTLGQPLTILTSHPVEALVRQPPNKW

LSNARMTHYQAMLLDAERVHFGPTVSLNPATLLPLPSGKPPRLSPDLAETMAQTDLTDQ

PLPDADLTWYTNGSSFIRNGERKAGAAVTTESEVIWAASLPPGTSAQRAELIALTQALK

MAKGKKLTVYTDSRYAFATAHVHGEIYRRRGLLTSEGKEIKNKNEILALLEALFLPKRL

SIIHCPGHQKGDSPQAKGNRLADDTAKKAATETQSSLTILSSSAS

FM Dimeric RT sequence(linker underlined)

SEQ ID NO:9:
EFTLQLEEEYRLFEPESTQKQEMDIWLKNFPQAWAETGGMGMAHCQAPVLIQLKATAT

PISIRQYPMPHEAYQGIKPHIRRMLDQGILKPCQSPWNTPLLPVKKPGTKDYRPVQDLRE

VNICRVEDIHPTVPNPYNLLSTLPPSHPWYTVLDLKDAFFCLRLHSESQLLFAFEWRDPEI

GLSGQLTWTRLPQGFKNSPTLFDEALHSDLADFRVRYPALVLLQYVDDLLLAAATRTEC

LEGTKALLETLGNKGYRASAKKAQICLQEVTYLGYSLKDGQRWLTKARKEAELSEPVPK

NPRQVREFLGTAGYCRLWIPGFAELAAPLYPLTRPGTLFQWGTEQQLAFENIRKALLSSP

ALGLPDITKPFELFIDENSGFAKGVLVQKLGPWKRPVAYLSKKLDTVASGWPPCLRMVA

AIAILVKDAGKLTLGQPLTILTSHPVEALVRQPPNKWLSNARMTHYQAMLLDAERVHFG

PTVSLNPATLLPLPSGKPPRLSPDLAETMAQTDLTDQPLPDADLTWYTDGSSFIRNGERK

AGAAVTTESEVIWAASLPPGTSAQRAELIALTQALKMAKGKKLTVYTDSRYAFATAHV

HGEIYRRRGLLTSEGKEIKNKNEILALLEALFLPKRLSIIHCPGHQKGDSPQAKGNRLADD
TAKKAATETQSSLTILSSSASKLEFTLNIEDEHRLHETSKEPDVSLGSTWLSDFPQAWAET
GGMGLAVRQAPLIIPLKATSTPVSIKQYPMSQEARLGIKPHIQRLLDQGILVPCQSPWNTP
LLPVKKPGTNDYRPVQDLREVNKRVEDIHPTVPNPYNLLSGLPPSHQWYTVLDLKDAFF
CLRLHPTSQPLFAFEWRDPEMGISGQLTWTRLPQGFKNSPTLFDEALHRDLADFRIQHPD
LILLQYVDDLLLAATSELDCQQGTRALLQTLGNLGYRASAKKAQICQKQVKYLGYLLK
EGQRWLTEARKETVMGQPTPKTPRQLREFLGTAGFCRLWLPGFAEMAAPLYPLTKTGTL
FNWGPDQQKAYQEIKQALLTAPALGLPDLTKPFELFVDEKQGYAKGVLTQKLGPWRRP
VAYLSKKLDPVAAGWPPCLRMVAAIAVLTKDAGKLTMGQPLVILAPHAVEALVKQPPD
RWLSNARMTHYQALLLDTDRVQFGPVVALNPATLLPLPEEGLQHNCLDILAEAHGTRP
DLTDQPLPDADHTWYTDGSSLLQEGQRKAGAAVTTETEVIWAKALPAGTSAQRAELIA
LTQALKMAEGKKLNVYTDSRYAFATAHIHGEIYRRRGLLTSEGKEIKNKDEILALLKAL
FLPKRLSILFICPGHQKGHSAEARGNRMADQAARKAAITETPDTSTLLSSSAS

FNM Dimeric RT sequence(linker underlined)

SEQ ID NO:10:
EFTLQLEEEYRLFEPESTQKQEMDIWLKNFPQAWAETGGMGMAHCQAPVLIQLKATAT
PISIRQYPMPHEAYQGIKPHIRRMLDQGILKPCQSPWNTPLLPVKKPGTKDYRPVQDLRE
VNKRVEDIHPTVPNPYNLLSTLPPSHPWYTVLDLKDAFFCLRLHSESQLLFAFEWRDPEI
GLSGQLTWTRLPQGFKNSPTLFDEALHSDLADFRVRYPALVLLQYVDDLLLAAATRTEC
LEGTKALLETLGNKGYRASAKKAQICLQEVTYLGYSLKDGQRWLTKARKEAILSIPVPK
NPRQVREFLGTAGYCRLWIPGFAELAAPLYPLTRPGTLFQWGTEQQLAFENIRKALLSSP
ALGLPDITKPFELFIDENSGFAKGVLVQKLGPWKRPVAYLSKKLDTVASGWPPCLRMVA
AIAILVKDAGKLTLGQPLTELTSHPVEALVRQPPNKWLSNARMTHYQAMLLDAERVHFG
PTVSLNPATLLPLPSGKPPRLSPDLAETMAQTDLTDQPLPDADLTWYTNGSSFERNGERK
AGAAVTTESEVIWAASLPPGTSAQRAELIALTQALKMAKGKKLTVYTDSRYAFATAHV
HGEIYRRRGLLTSEGKEIKNKNEILALLEALFLPKRLSIIHCPGHQKGDSPQAKGNRLADD
TAKKAATETQSSLTILSSSASKLEFTLNIEDEHRLHETSKEPDVSLGSTWLSDFPQAWAET
GGMGLAVRQAPLIIPLKATSTPVSIKQYPMSQEARLGIKPHIQRLLDQGILVPCQSPWNTP
LLPVKKPGTNDYRPVQDLREVNKRVEDIFIPTVPNPYNLLSGLPPSHQWYTVLDLKDAFF
CLRLHPTSQPLFAFEWRDPEMGISGQLTWTRLPQGFKNSPTLFDEALHRDLADFRIQHPD
LILLQYVDDLLLAATSELDCQQGTRALLQTLGNLGYRASAKKAQICQKQVKYLGYLLK
EGQRWLTEARKETVMGQPTPKTPRQLREFLGTAGFCRLWIPGFAEMAAPLYPLTKTGTL
FNWGPDQQKAYQEIKQALLTAPALGLPDLTKPFELFVDEKQGYAKGVLTQKLGPWRRP
VAYLSKKLDPVAAGWPPCLRMVAAIAVLTKDAGKLTMGQPLVILAPHAVEALVKQPPD
RWLSNARMTHYQALLLDTDRVQFGPVVALNPATLLPLPEEGLQHNCLDILAEAHGTRP
DLTDQPLPDADHTWYTDGSSLLQEGQRKAGAAVTTETEVIWAKALPAGTSAQRAELIA
LTQALKMAEGKKLNVYTDSRYAFATAHIFIGELYRRRGLLTSEGKEIKNKDEILALLKAL
FLPKRLSIIHCPGHQKGHSAEARGNRMADQAARKAAITETPDTSTLLSSSAS

FNMN Dimeric RT sequence(linker underlined)

SEQ ID NO:11:
EFTLQLEEEYRLFEPESTQKQEMDIWLKNFPQAWAETGGMGMAHCQAPVLIQLKATAT

PISIRQYPMPHEAYQGIKPHIRRIVILDQGILKPCQSPWNTPLLPVKKPGTKDYRPVQDLRE

VNKRVEDIHPTVPNPYNLLSTLPPSHPWYTVLDLKDAFFCLRLHSESQLLFAFEWRDPEI

GLSGQLTWTRLPQGFKNSPTLFDEALHSDLADFRVRYPALVLLQYVDDLLLAAATRTEC

LEGTKALLETLGNKGYRASAKKAQICLQEVTYLGYSLKDGQRWLTKARKEAILSWVPK

NPRQVREFLGTAGYCRLWIPGFAELAAPLYPLTRPGTLFQWGTEQQLAFENIRKALLSSP

ALGLPDITKPFELFIDENSGFAKGVLVQKLGPWKRPVAYLSKKLDTVASGWPPCLRMVA

AIAILVKDAGKLTLGQPLTILTSHPVEALVRQPPNKWLSNARMTHYQAMLLDAERVHFG

PTVSLNPATLLPLPSGKPPRLSPDLAETMAQTDLTDQPLPDADLTWYTNGSSFIRNGERK

AGAAVTTESEVIWAASLPPGTSAQRAELIALTQALKMAKGICKLTVYTDSRYAFATAHV

HGEIYRRRGLLTSEGKEIKNKNEILALLEALFLPKRLSIIHCPGHQKGDSPQAKGNRLADD

TAKKAATETQSSLTIL<u>SSSASK</u>LEFTLNIEDEHRLHETSKEPDVSLGSTWLSDFPQAWAET

GGMGLAVRQAPLIIPLKATSTPVSIKQYPMSQEARLGIKPHIQRLLDQGILVPCQSPWNTP

LLPVKKPGTNDYRPVQDLREVNKRVEDIHPTVPNPYNLLSGLPPSHQWYTVLDLKDAFF

CLRLHPTSQPLFAFEWRDPEMGISGQLTWTRLPQGFKNSPTLFDEALHRDLADFRIQHPD

LILLQYVDDLLLAATSELDCQQGTRALLQTLGNLGYRASAKKAQICQKQVKYLGYLLK

EGQRWLTEARKETVMGQPTPKTPRQLREFLGTAGFCRLWIPGFAEMAAPLYPLTKTGTL

FNWGPDQQKAYQEEKQALLTAPALGLPDLTKPFELFVDEKQGYAKGVLTQKLGPWRRP

VAYLSKKLDPVAAGWPPCLRMVAAIAVLTKDAGKLTMGQPLVILAPHAVEALVKQPPD

RWLSNARMTHYQALLLDTDRVQFGPVVALNPATLLPLPEEGLQHNCLDILAEAHGTRP

DLTDQPLPDADHTWYTNGSSLLQEGQRKAGAAVTTETEVIWAKALPAGTSAQRAELIA

LTQALKMAEGKKLNVYTDSRYAFATAHIRGEIYRRRGLLTSEGKEIKNKDEILALLKAL

FLPKRLSIEFICPGHQKGHSAEARGNRMADQAARKAAITETPDTSTLLSSSAS

MF Dimeric RT sequence(linker underlined)

SEQ ID NO:12:
EFTLNIEDEHRLHETSKEPDVSLGSTWLSDFPQAWAETGGMGLAVRQAPLIIPLKATSTP

VSIKQYPMSQEARLGIKPHIQRLLDQGLLVPCQSPWNTPLLPVICKPGTNDYRPVQDLREV

NKRVEDIHPTVPNPYNLLSGLPPSHQWYTVLDLKDAFFCLRLHPTSQPLFAFEWRDPEM

GISGQLTWTRLPQGFKNSPTLFDEALIARDLADFRIQHPDLILLQYVDDLLLAATSELDCQ

QGTRALLQTLGNLGYRASAKKAQICQKQVKYLGYLLKEGQRWLTEARKETVMGQPTP

KTPRQLREFLGTAGFCRLWIPGFAEMAAPLYPLTKTGTLFNVVGPDQQKAYQEIKQALLT

APALGLPDLTKPFELFVDEKQGYAKGVLTQKLGPWRRPVAYLSKKLDPVAAGWPPCLR

MVAAIAVLTKDAGKLTMGQPLVILAPHAVEALVKQPPDRWLSNARMTHYQALLLDTD

RVQFGPVVALNPATLLPLPEEGLQHNCLDILAEAHGTRPDLTDQPLPDADHTWYTDGSS

LLQEGQRKAGAAVTTETEVIWAKALPAGTSAQRAELIALTQALKMAEGKKLNVYTDSR

YAFATAHIHGEIYRRRGLLTSEGKEIKNKDEILALLKALFLPKRLSICHCPGHQKGHSAEA

RGNRMADQAARKAAITETPDTSTLL<u>SSSASK</u>LEFTLQLEEEYRLFEPESTQKQEMDIWLK

NFPQAWAETGGMGMAHCQAPVLIQLKATATPISIRQYPMPHEAYQGIKPHIRRMLDQGI

```
LKPCQSPWNTPLLPVKKPGTKDYRPVQDLREVNKRVEDIHPTVPNPYNLLSTLPPSHPW

YTVLDLKDAFFCLRLHSESQLLFAFEWRDPEIGLSGQLTWTRLPQGFKNSPTLFDEALHS

DLADFRVRYPALVLLQYVDDLLLAAATRTECLEGTKALLETLGNKGYRASAKKAQICL

QEVTYLGYSLKDGQRWLTKARKEAILSIPVPKNPRQVREFLGTAGYCRLWIPGFAELAA

PLYPLTRPGTLFQWGTEQQLAFENIRKALLSSPALGLPDITKPFELF+DENSGFAKGVLVQ

KLGPWKRPVAYLSKKLDTVASGWPPCLRMVAAIAILVKDAGKLTLGQPLTILTSHPVEA

LVRQPPNKWLSNARMTHYQAMLLDAERVHFGPTVSLNPATLLPLPSGKPPRLSPDLAET

MAQTDLTDQPLPDADLTWYTDGSSFIRNGERKAGAAVTTESEVIWAASLPPGTSAQRAE

LIALTQALKMAKGKKLTVYTDSRYAFATAHVHGEIYRRRGLLTSEGKEIKNKNEILALL

EALFLPKRLSIIHCPGHQKGDSPQAKGNRLADDTAKKAATETQSSLTILSSSAS
```

MNF Dimeric RT sequence(linker underlined)

SEQ ID NO:13:
```
EFTLNIEDEHRLHETSKEPDVSLGSTWLSDFPQAWAETGGMGLAVRQAPLIIPLKATSTP

VSIKQYPMSQEARLGIKPHIQRLLDQGILVPCQSPWNTPLLPVKKPGTNDYRPVQDLREV

NKRVEDIEPTVPNPYNLLSGLPPSHQWYTVLDLKDAFFCLRLHPTSQPLFAFEWRDPEM

GISGQLTWTRLPQGFKNSPTLFDEALHRDLADFRIQHPDLILLQYVDDLLLAATSELDCQ

QGTRALLQTLGNLGYRASAKKAQICQKQVKYLGYLLKEGQRWLTEARKETVMGQPTP

KTPRQLREFLGTAGFCRLWIPGFAEMAAPLYPLTKTGTLFNWGPDQQKAYQEIKQALLT

APALGLPDLTKPFELFVDEKQGYAKGVLTQKLGPWRRPVAYLSKKLDPVAAGWPPCLR

MVAAIAVLTKDAGKLTMGQPLVILAPHAVEALVKQPPDRWLSNARMTHYQAULDTD

RVQFGPVVALNPATLLPLPEEGLQHNCLDILAEAHGTRPDLTDQPLPDADHTWYTNGSS

LLQEGQRKAGAAVTTETEVIWAKALPAGTSAQRAELIALTQALKMAEGKKLNVYTDSR

YAFATAHIHGEIYRRRGLLTSEGKEIKNKDEILALLKALFLPKRLSIIHCPGHQKGHSAEA

RGNRMADQAARKAAITETPDTSTLLSSSASKLEFTLQLEEEYRLFEPESTQKQEMDIWLK

NFPQAWAETGGMGMAHCQAPVLIQLKATATPISIRQYPMPHEAYQGIKPHIRRMLDQGI

LKPCQSPWNTPLLPVKKPGTKDYRPVQDLREVNKRVED+HPTVPNPYNLLSTLPPSHPW

YTVLDLKDAFFCLRLHSESQLLFAFEWRDPEIGLSGQLTWTRLPQGFKNSPTLFDEALHS

DLADFRVRYPALVLLQYVDDLLLAAATRTECLEGTKALLETLGNKGYRASAKKAQICL

QEVTYLGYSLKDGQRWLTKARKEAILSIPVPKNPRQVREFLGTAGYCRLWIPGFAELAA

PLYPLTRPGTLFQWGTEQQLAFENIRKALLSSPALGLPDITKPFELFIDENSGFAKGVLVQ

KLGPWKRPVAYLSKKLDTVASGWPPCLRMVAAIAILVKDAGKLTLGQPLTILTSHPVEA

LVRQPPNKWLSNARMTHYQAMLLDAERVHFGPTVSLNPATLLPLPSGKPPRLSPDLAET

MAQTDLTDQPLPDADLTWYTDGSSFIRNGERKAGAAVTTESEVIWAASLPPGTSAQRAE

LIALTQALKMAKGKKLTVYTDSRYAFATAHVHGEIYRRRGLLTSEGKEIKNKNEILALL

EALFLPKRLSIIHCPGHQKGDSPQAKGNRLADDTAKKAATETQSSLTILSSSAS
```

MNFN Dimeric RT sequence(linker underlined)

SEQ ID NO:14:
```
EFTLNIEDEHRLHETSKEPDVSLGSTWLSDFPQAWAETGGMGLAVRQAPLULKATSTP

VSIKQYPMSQEARLGIKPHIQRLLDQGILVPCQSPWNTPLLPVKKPGTNDYRPVQDLREV

NKRVEDEFIPTVPNPYNLLSGLPPSHQWYTVLDLKDAFFCLRLHPTSQPLFAFEWRDPEM
```

```
GISGQLTWTRLPQGFKNSPTLFDEALHRDLADFRIQHPDLILLQYVDDLLLAATSELDCQ

QGTRALLQTLGNLGYRASAKKAQICQKQVKYLGYLLKEGQRWLTEARKETVMGQPTP

KTPRQLREFLGTAGFCRLWIPGFAEMAAPLYPLTKTGTLFNWGPDQQKAYQEIKQALLT

APALGLPDLTKPFELFVDEKQGYAKGVLTQKLGPWRRPVAYLSKKLDPVAAGWPPCLR

MVAAIAVLTKDAGKLTMGQPLVILAPHAVEALVKQPPDRWLSNARMTHYQALLLDTD

RVQFGPVVALNPATLLPLPEEGLQHNCLDILAEAHGTRPDLTDQPLPDADHTWYTNGSS

LLQEGQRKAGAAVTTETEVIWAKALPAGTSAQRAELIALTQALKMAEGKKLNVYTDSR

YAFATAHLHGEIYRRRGLLTSEGKEIKNKDEILALLKALFLPKRLSIIHCPGHQKGHSAEA

RGNRMADQAARKAAITETPDTSTLLSSSASKLEFTLQLEEEYRLFEPESTQKQEMDIWLK

NFPQAWAETGGMGMAHCQAPVLIQLKATATPISIRQYPNEPHEAYQGIKPHIRRMLDQGI

LKPCQSPWNTPLLPVICKPGTKDYRPVQDLREVNKRVEDIHPTVPNPYNLLSTLPPSHPW

YTVLDLKDAFFCLRLHSESQLLFAFEWRDPEIGLSGQLTWTRLPQGFKNSPTLFDEALHS

DLADFRVRYPALVLLQYVDDLLLAAATRTECLEGTKALLETLGNKGYRASAKKAQICL

QEVTYLGYSLKDGQRWLTKARKEAILSIPVPKNPRQVREFLGTAGYCRLWIPGFAELAA

PLYPLTRPGTLFQWGTEQQLAFENLRKALLSSPALGLPDITKPFELFEDENSGFAKGVLVQ

KLGPWKRPVAYLSKKLDTVASGWPPCLRMVAAIAILVKDAGKLTLGQPLTILTSHPVEA

LVRQPPNKWLSNARMTHYQAMLLDAERVHFGPTVSLNPATLLPLPSGKPPRLSPDLAET

MAQTDLTDQPLPDADLTWYTNGSSFTRNGERKAGAAVTTESEVIWAASLPPGTSAQRAE

LIALTQALKMAKGKKLTVYTDSRYAFATAHVHGEIYRRRGLLTSEGKEIKNKNEILALL

EALFLPKRLSIIHCPGHQKGDSPQAKGNRLADDTAKKAATETQSSLTILSSSAS
```

FFN Dimeric RT sequence(linker underlined)

```
                                                            SEQ ID NO:15:
EFTLQLEEEYRLFEPESTQKQEMDIWLKNFPQAWAETGGMGMAHCQAPVLIQLKATAT

PISIRQYPMPHEAYQGIKPHIRRMLDQGELKPCQSPWNTPLLPVKKPGTKDYRPVQDLRE

VNKRVEDIHPTVPNPYNLLSTLPPSHPWYTVLDLKDAFFCLRLHSESQLLFAFEWRDPEI

GLSGQLTWTRLPQGFKNSPTLFDEALHSDLADFRVRYPALVLLQYVDDLLLAAATRTEC

LEGTKALLETLGNKGYRASAKKAQICLQEVTYLGYSLKDGQRWLTKARKEAILSIPVPK

NPRQVREFLGTAGYCRLWIPGFAELAAPLYPLTRPGTLFQWGTEQQLAFENIRKALLSSP

ALGLPDITKPFELFIDENSGFAKGVLVQKLGPWKRPVAYLSKKLDTVASGWPPCLRMVA

AIAILVKDAGKLTLGQPLTILTSHPVEALVRQPPNKWLSNARMTHYQAMLLDAERVHFG

PTVSLNPATLLPLPSGKPPRLSPDLAETMAQTDLTDQPLPDADLTWYTDGSSFIRNGERK

AGAAVTTESEVIWAASLPPGTSAQRAELIALTQALKMAKGKKLTVYTDSRYAFATAHV

HGEIYRRRGLLTSEGKEIKNKNEELALLEALFLPKRLSIIHCPGHQKGDSPQAKGNRLADD

TAKKAATETQSSLTILSSSASKLEFTLQLEEEYRLFEPESTQKQEMDIWLKNFPQAWAET

GGMGMAHCQAPVLIQLKATATPISIRQYPMPHEAYQGIKPHIRRMLDQGILKPCQSPWN

TPLLPVKKPGTKDYRPVQDLREVNKRVEDIHPTVPNPYNLLSTLPPSHPWYTVLDLKDA

FFCLRLHSESQLLFAFEWRDPEIGLSGQLTWTRLPQGFKNSPTLFDEALHSDLADFRVRY

PALVLLQYVDDLLLAAATRTECLEGTKALLETLGNKGYRASAKKAQICLQEVTYLGYS

LKDGQRWLTKARKEAILSIPVPKNPRQVREFLGTAGYCRLWIPGFAELAAPLYPLTRPGT

LFQWGTEQQLAFENIRKALLSSPALGLPDITKPFELFIDENSGFAKGVLVQKLGPWICRPV
```

AYLSKKLDTVASGWPPCLRMVAAIAILVKDAGKLTLGQPLTILTSHPVEALVRQPPNKW

LSNARMTHYQAMLLDAERVHFGPTVSLNPATLLPLPSGKPPRLSPDLAETMAQTDLTDQ

PLPDADLTWYTNGSSFIRNGERKAGAAVTTESEVIWAASLPPGTSAQRAELIALTQALK

MAKGKKLTVYTDSRYAFATAHVHGEIYRRRGLLTSEGKEIKNKNEILALLEALFLPKRL

SILHCPGHQKGDSPQAKGNRLADDTAKKAATETQSSLIMSSSAS

FMN Dimeric RT sequence (linker underlined)

SEQ ID NO:16:
EFTLQLEEEYRLFEPESTQKQEMDIWLKNFPQAWAETGGMGMAHCQAPVLIQLKATAT

PISIRQYPMPHEAYQGIKPHIRRMLDQGILKPCQSPWNTPLLPVKKPGTKDYRPVQDLRE

VNKRVEDIHPTVPNPYNLLSTLPPSHPWYTVLDLKDAFFCLRLHSESQLLFAFEWRDPEI

GLSGQLTWTRLPQGFKNSPTLFDEALHSDLADFRVRYPALVLLQYVDDLLLAAATRTEC

LEGTKALLETLGNKGYRASAKKAQICLQEVTYLGYSLKDGQRWLTKARKEALLSIPVPK

NPRQVREFLGTAGYCRLWIPGFAELAAPLYPLTRPGTLFQWGTEQQLAFENIRKALLSSP

ALGLPDITKPFELFIDENSGFAKGVLVQKLGPWKRPVAYLSKKLDTVASGWPPCLRMVA

AIAILVKDAGKLTLGQPLTLLTSHPVEALVRQPPNKWLSNARMTHYQAMLLDAERVHFG

PTVSLNPATLLPLPSGKPPRLSPDLAETMAQTDLTDQPLPDADLTWYTDGSSFIRNGERK

AGAAVTTESEVIWAASLPPGTSAQRAELIALTQALKMAKGKKLTVYTDSRYAFATAHV

HGEIYRRRGLLTSEGKEIKNKNEILALLEALFLPKRLSILEICPGHQKGDSPQAKGNRLADD

TAKKAATETQSSLTILSSSASKLEFTLNIEDEHRLHETSKEPDVSLGSTWLSDFPQAWAET

GGMGLAVRQAPLIIPLKATSTPVSIKQYPMSQEARLGIKPHIQRLLDQGILVPCQSPWNTP

LLPVICKPGTNDYRPVQDLREVNKRVEDIHPTVPNPYNLLSGLPPSHQWYTVLDLKDAFF

CLRLHPTSQPLFAFEWRDPEMGISGQLTWTRLPQGFKNSPTLFDEALHRDLADFRIQHPD

LILLQYVDDLLLAATSELDCQQGTRALLQTLGNLGYRASAKKAQICQKQVKYLGYLLK

EGQRWLTEARKETVMGQPTPKTPRQLREFLGTAGFCRLWIPGFAEMAAPLYPLTKTGTL

FNWGPDQQKAYQEIKQALLTAPALGLPDLTKPFELFVDEKQGYAKGVLTQKLGPWRRP

VAYLSKKLDPVAAGWPPCLRMVAAIAVLTKDAGICLTMGQPLVILAPHAVEALVKQPPD

RWLSNARMTHYQALLLDTDRVQFGPVVALNPATLLPLPEEGLQHNCLDILAEAHGTRP

DLTDQPLPDADHTWYTNGSSLLQEGQRKAGAAVTTETEVIWAKALPAGTSAQRAELIA

LTQALKMAEGKKLNVYTDSRYAFATAHIHGEIYRRRGLLTSEGKEIKNKDEILALLKAL

FLPKRLSIIHCPGHQKGHSAEARGNRMADQAARKAAITETPDTSTLLSSSAS

MEN Dimeric RT sequence (linker underlined)

SEQ ID NO:17:
EFTLNIEDEHRLHETSKEPDVSLGSTWLSDFPQAWAETGGMGLAVRQAPLIIPLKATSTP

VSIKQYPMSQEARLGIKPHIQRLLDQGILVPCQSPWNTPLLPVKKPGTNDYRPVQDLREV

NKRVEDIHPTVPNPYNLLSGLPPSHQWYTVLDLKDAFFCLRLHPTSQPLFAFEWRDPEM

GISGQLTWTRLPQGFKNSPTLFDEALHRDLADFRIQHPDLILLQYVDDLLLAATSELDCQ

QGTRALLQTLGNLGYRASAKKAQICQKQVKYLGYLLKEGQRWLTEARKETVMGQPTP

KTPRQLREFLGTAGFCRLWIPGFAEMAAPLYPLTKTGTLFNWGPDQQKAYQEIKQALLT

APALGLPDLTKPFELFVDEKQGYAKGVLTQKLGPWRRPVAYLSKKLDPVAAGWPPCLR

MVAAIAVLTKDAGKLTMGQPLVILAPHAVEALVKQPPDRWLSNARMTHYQALLLDTD

RVQFGPVVALNPATLLPLPEEGLQHNCLDILAEAHGTRPDLTDQPLPDADHTWYTDGSS

LLQEGQRKAGAAVTTETEVIWAKALPAGTSAQRAELIALTQALKMAEGKKLNVYTDSR

YAFATAHIFIGEIYRRRGLLTSEGKEEKNKDEILALLKALFLPKRLSIIHCPGHQKGHSAEA

RGNRMADQAARKAAITETPDTSTLL<u>SSSASKL</u>EFTLQLEEEYRLFEPESTQKQEMDIWLK

NFPQAWAETGGMGMAHCQAPVLIQLKATATPISIRQYPMPHEAYQGIKPHIRRMLDQGI

LKPCQSPWNTPLLPVKKPGTKDYRPVQDLREVNKRVEDIHPTVPNPYNLLSTLPPSHPW

YTVLDLKDAFFCLRLHSESQLLFAFEWRDPEIGLSGQLTWTRLPQGFKNSPTLFDEALHS

DLADFRVRYPALVLLQYVDDLLLAAATRTECLEGTKALLETLGNKGYRASAKKAQICL

QEVTYLGYSLKDGQRWLTKARKEAILSIPVPKNPRQVREFLGTAGYCRLWIPGFAELAA

PLYPLTRPGTLFQWGTEQQLAFENIRKALLSSPALGLPDITKPFELFIDENSGFAKGVLVQ

KLGPWKRPVAYLSKKLDTVASGWPPCLRMVAAIAILVKDAGKLTLGQPLTILTSHPVEA

LVRQPPNKWLSNARMTHYQAMLLDAERVHFGPTVSLNPATLLPLPSGKPPRLSPDLAET

MAQTDLTDQPLPDADLTWYTNGSSFIRNGERKAGAAVTTESEVIWAASLPPGTSAQRAE

LIALTQALKMAKGKKLTVYTDSRYAFATAHVHGEIYRRRGLLTSEGKEIKNKNEILALL

EALFLPKRLSIIHCPGHQKGDSPQAKGNRLADDTAKKAATETQSSLTILSSSAS

MMN Dimeric RT sequence (linker underlined)

SEQ ID NO:18:
EFTLNEEDEHRLHETSKEPDVSLGSTWLSDFPQAWAETGGMGLAVRQAPLIIPLKATSTP

VSIKQYPMSQEARLGIKPHIQRLLDQGILVPCQSPWNTPLLPVKKPGTNDYRPVQDLREV

NKRVEDIHPTVPNPYNLLSGLPPSHQWYTVLDLKDAFFCLRLHPTSQPLFAFEWRDPEM

GISGQLTWTRLPQGFKNSPTLFDEALFIRDLADFRIQHPDLILLQYVDDLLLAATSELDCQ

QGTRALLQTLGNLGYRASAKKAQICQKQVKYLGYLLKEGQRWLTEARKETVMGQPTP

KTPRQLREFLGTAGFCRLWIPGFAEMAAPLYPLTKTGTLFNWGPDQQKAYQEIKQALLT

APALGLPDLTKPFELFVDEKQGYAKGVLTQKLGPWRRPVAYLSKKLDPVAAGWPPCLR

MVAAIAVLTKDAGKLTMGQPLVILAPHAVEALVKQPPDRWLSNARMTHYQALLLDTD

RVQFGPVVALNPATLLPLPEEGLQIINCLDILAEAHGTRPDLTDQPLPDADHTWYTDGSS

LLQEGQRKAGAAVTTETEVIWAKALPAGTSAQRAELIALTQALICMAEGKICLNVYTDSR

YAFATAHIEIGEIYRRRGLLTSEGKEIKNKDEILALLKALFLPKRLSIIHCPGHQKGHSAEA

RGNRMADQAARKAAITETPDTSTLL<u>SSSASKL</u>EFTLNIEDEHRLHETSKEPDVSLGSTWL

SDFPQAWAETGGMGLAVRQAPLIIPLKATSTPVSIKQYPMSQEARLGIKPHIQRLLDQGIL

VPCQSPWNTPLLPVKKPGTNDYRPVQDLREVNKRVEDIHPTVPNPYNLLSGLPPSHQWY

TVLDLKDAFFCLRLHPTSQPLFAFEWRDPEMGISGQLTWTRLPQGFKNSPTLFDEALHR

DLADFRIQHPDLILLQYVDDLLLAATSELDCQQGTRALLQTLGNLGYRASAKKAQICQK

QVKYLGYLLKEGQRWLTEARKETVMGQPTPKTPRQLREFLGTAGFCRLWIPGFAEMAA

PLYPLTKTGTLFNWGPDQQKAYQEIKQALLTAPALGLPDLTKPFELFVDEKQGYAKGVL

TQKLGPWRRPVAYLSICKLDPVAAGWPPCLRMVAAIAVLTKDAGKLTMGQPLVILAPH

AVEALVKQPPDRWLSNARMTHYQALLLDTDRVQFGPVVALNPATLLPLPEEGLQHNCL

DILAEAHGTRPDLTDQPLPDADHTWYTNGSSLLQEGQRKAGAAVTTETEVIWAKALPA

GTSAQRAELIALTQALKMAEGKKLNVYTDSRYAFATAHIHGEIYRRRGLLTSEGICEIKN

-continued

KDEILALLKALFLPKRLSIIHCPGHQKGHSAEARGNRMADQAARKAAITETPDTSTLLSS
SAS

Enzyme purification:

E.coli cells expressed the enzyme were re-suspended in a lysis buffer. Cells were disrupted on ice with pulses of sonication (2×30 sec, duty cycle 80%, output 10), and centrifuged at 19,000 rpm for 10 min. The supernatant was filtered through a 0.22 um filtration unit, diluted with 10× buffer A for iMAC chromatography (50 mM KPO4, pH6.5, 300 mM KCl, 0.1% Tween 20), and loaded onto a Nuvia iMAC column. The enzyme was eluted with a linear gradient to buffer B (buffer A plus 500 mM imidazole). The fraction containing the enzyme was pooled and concentrated with an Amicon Ultra-15 centrifugal filter unit. The sample was applied to a size exclusion column (SEC650), the fractions containing the purified enzyme was collected.

RT-qPCR Assay:

iScript Advanced reverse transcription mix was used for the reverse transcription of cDNA. The purified enzyme was added into the reaction. iScript advanced reverse transcriptase was used as a control. In order to study the effect of temperature on cDNA synthesis the reverse transcription reaction was carried out at 42, 55, and 60C for 30 min respectively. The cDNA synthesis speed by the purified enzymes was also compared to the iScript Advanced reverse transcriptase, in which the reverse transcription was carried out in iScript Advanced reaction mix for 30, 2, 1 min respectively. After the cDNA synthesis, qPCR was performed on different targets. To assess the performance of the cDNA synthesis, delta quantification cycle (dCq) was calculated using a cDNA reaction at 42C for 30 min as a control.

TABLE 1

Dimeric MLV RTs (MNM and MM) displayed better thermostability than the wild type control. Two-step RT-qPCR was performed on 6 different targets.

| | MNM | MM | Control | MNM | MM | Control | MNM | MM | Control |
|---|---|---|---|---|---|---|---|---|---|
| | APC | | | CBP | | | beta Actin | | |
| | Cq | | | | | | | | |
| 42 C. | 25.19 | 26.99 | 25.17 | 26.65 | 27.20 | 26.78 | 16.20 | 16.89 | 16.46 |
| 55 C. | 26.26 | 26.75 | 26.30 | 27.74 | 28.27 | 29.21 | 17.32 | 17.71 | 19.23 |
| 60 C. | 26.21 | 27.21 | 26.73 | 27.65 | 28.38 | 29.52 | 17.26 | 17.56 | 19.38 |
| | dCq | | | | | | | | |
| 55 C.-42 C. | 1.07 | −0.24 | 1.13 | 1.10 | 1.07 | 2.43 | 1.12 | 0.82 | 2.77 |
| 60 C.-42 C. | 1.01 | 0.22 | 1.56 | 1.00 | 1.19 | 2.74 | 1.06 | 0.67 | 2.92 |
| | GAPDH | | | 18s | | | Tub | | |
| | Cq | | | | | | | | |
| 42 C. | 16.59 | 17.45 | 16.16 | 4.58 | 5.15 | 4.88 | 18.61 | 19.23 | 18.49 |
| 55 C. | 17.13 | 18.48 | 18.62 | 10.54 | 10.89 | 14.08 | 19.37 | 20.09 | 21.14 |
| 60 C. | 17.15 | 18.68 | 19.24 | 10.96 | 11.45 | 14.68 | 19.24 | 19.92 | 21.53 |
| | dCq | | | | | | | | |
| 55 C.-42 C. | 0.54 | 1.02 | 2.46 | 5.96 | 5.74 | 9.20 | 0.76 | 0.86 | 2.64 |
| 60 C.-42 C. | 0.56 | 1.22 | 3.08 | 6.38 | 6.30 | 9.80 | 0.63 | 0.69 | 3.03 |

TABLE 2

Additional dimeric RTs displayed better thermostability than the wild type control. The template target was human GAPDH.

| | MF | MNF | MM | MNM | FNM | RT control |
|---|---|---|---|---|---|---|
| Cq (55 C.) | 20.64 | 20.88 | 16.91 | 16.64 | 21.63 | 17.16 |
| Cq (42 C.) | 19.60 | 19.70 | 15.99 | 15.86 | 20.75 | 13.28 |
| dCq | 1.04 | 1.18 | 0.92 | 0.78 | 0.88 | 3.88 |
| Cq (60 C.) | 21.32 | 20.79 | 17.58 | 17.35 | 21.54 | 19.40 |
| Cq (42 C.) | 18.41 | 18.39 | 14.67 | 14.65 | 19.66 | 13.30 |
| dCq | 2.91 | 2.39 | 2.91 | 2.69 | 1.88 | 6.10 |
| Cq (42 C. 5 min) | 18.63 | 18.62 | 14.63 | 14.55 | 19.53 | 16.06 |
| Cq (42 C. 30 min) | 18.41 | 18.39 | 14.67 | 14.65 | 19.66 | 13.30 |
| dCq | 0.22 | 0.23 | −0.04 | −0.11 | −0.13 | 2.76 |
| Cq (42 C. 2.5 min) | 19.54 | 19.60 | 15.35 | 15.19 | 20.41 | 17.00 |
| Cq (42 C. 30 min) | 18.41 | 18.39 | 14.67 | 14.65 | 19.66 | 13.30 |
| dCq | 1.13 | 1.21 | 0.68 | 0.53 | 0.75 | 3.70 |

MF: MLVRT-FLVRT dimer;
MNF: MLVRT RNaseH(−)-FLVRT dimer;
MM: MLVRT-MLVRT dimer;
MNM: MLVRT RNaseH(−)-MLVRT dimer;
FNM: FLVRT RNaseH(−)-MLVRT dimer;
RT control: Purified monomeric RT.

All five dimeric RT's exhibited better stability than the monomeric RT control at the two temps, as shown for example by the lower dCq values. All five dimeric RTs also exhibited reduced reaction time vs the RT control.

The examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A polypeptide comprising a first reverse transcriptase and a second reverse transcriptase covalently linked by a heterologous linker, wherein the first reverse transcriptase and the second reverse transcriptase are identical.

2. The polypeptide of claim 1, wherein the amino acid linker is between 1-30 amino acids long.

3. The polypeptide of claim 1, wherein the first or second reverse transcriptase is selected from the group consisting of murine leukemia virus (MLV) reverse transcriptase, Feline leukemia virus (FLV) reverse transcriptase, bovine leukemia virus (BLV) reverse transcriptase, Avian Myeloblastosis Virus (AMV) reverse transcriptase, Respiratory Syncytial Virus (RSV) reverse transcriptase, Equine Infectious Anemia Virus (EIAV) reverse transcriptase, Rous-associated Virus-2 (RAV2) reverse transcriptase, SUPERSCRIPT II reverse transcriptase, SUPERSCRIPT I reverse transcriptase, THERMOSCRIPT reverse transcriptase and MMLV RNase H-reverse transcriptase.

4. The polypeptide of claim 1, wherein the polypeptide is no more than 2000 amino acids in length.

5. The polypeptide of claim 1, wherein at least the first and the second reverse transcriptase have at least one mutation compared to a naturally-occurring reverse transcriptase.

6. The polypeptide of claim 5, wherein the first and the second reverse transcriptase is an RNase H-reverse transcriptase.

7. A polypeptide comprising a first reverse transcriptase and a second reverse transcriptase covalently linked by a heterologous linker, wherein the first reverse transcriptase and the second reverse transcriptase are at least 90% identical.

8. The polypeptide of claim 7, wherein the first and second reverse transcriptases are a murine leukemia virus (MLV) reverse transcriptase.

9. The polypeptide of claim 7, wherein the first and second reverse transcriptases are a Feline leukemia virus (FLV) reverse transcriptase.

10. The polypeptide of claim 7, wherein the amino acid linker is between 1-30 amino acids long.

11. The polypeptide of claim 7, wherein the first or second reverse transcriptase is selected from the group consisting of murine leukemia virus (MLV) reverse transcriptase, Feline leukemia virus (FLV) reverse transcriptase, bovine leukemia virus (BLV) reverse transcriptase, Avian Myeloblastosis Virus (AMV) reverse transcriptase, Respiratory Syncytial Virus (RSV) reverse transcriptase, Equine Infectious Anemia Virus (EIAV) reverse transcriptase, Rous-associated Virus-2 (RAV2) reverse transcriptase, SUPERSCRIPT II reverse transcriptase, SUPERSCRIPT I reverse transcriptase, THERMOSCRIPT reverse transcriptase and MMLV RNase H-reverse transcriptase.

12. The polypeptide of claim 7, wherein the polypeptide is no more than 2000 amino acids in length.

13. The polypeptide of claim 7 wherein at least the first or the second reverse transcriptase have at least one mutation compared to a naturally-occurring reverse transcriptase.

14. The polypeptide of claim 13, wherein the first or the second reverse transcriptase is an RNase H-reverse transcriptase.

15. The polypeptide of claim 7, wherein the polypeptide comprises SEQ ID NO:3, SEQ ID NO:4, SEQ ID NO:5, or SEQ ID NO:18.

16. The polypeptide of claim 7, wherein the first reverse transcriptase, the second reverse transcriptase or both comprise SEQ ID NO:1.

17. A reaction mixture comprising:
RNA or DNA template; and
the polypeptide of claim 7.

18. The reaction mixture of claim 17, further comprising a buffer selected from the group consisting of Tris, HEPES, ACES, PIPES, MOPSO, BES, MOPS, TES, TAPSO, POPSO, BICINE, TAPS, and AMPSO.

19. The reaction mixture of claim 17, further comprising at least one oligonucleotide primer and/or deoxynucleotides.

* * * * *

```
                        SEQUENCE LISTING

<160> NUMBER OF SEQ ID NOS: 18

<210> SEQ ID NO 1
<211> LENGTH: 671
<212> TYPE: PRT
<213> ORGANISM: Artificial Sequence
<220> FEATURE:
<223> OTHER INFORMATION: Synthetic construct

<400> SEQUENCE: 1

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
```

```
                340                 345                 350
Thr Ala Pro Ala Leu Gly Leu Pro Asp Leu Thr Lys Pro Phe Glu Leu
            355                 360                 365

Phe Val Asp Glu Lys Gln Gly Tyr Ala Lys Gly Val Leu Thr Gln Lys
        370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu
            660                 665                 670

<210> SEQ ID NO 2
<211> LENGTH: 667
<212> TYPE: PRT
<213> ORGANISM: Artificial Sequence
<220> FEATURE:
<223> OTHER INFORMATION: Synthetic construct

<400> SEQUENCE: 2

Thr Leu Gln Leu Glu Glu Glu Tyr Arg Leu Phe Glu Pro Glu Ser Thr
1               5                   10                  15

Gln Lys Gln Glu Met Asp Ile Trp Leu Lys Asn Phe Pro Gln Ala Trp
            20                  25                  30

Ala Glu Thr Gly Gly Met Gly Met Ala His Cys Gln Ala Pro Val Leu
```

-continued

```
                35                  40                  45
Ile Gln Leu Lys Ala Thr Ala Thr Pro Ile Ser Ile Arg Gln Tyr Pro
 50                  55                  60
Met Pro His Glu Ala Tyr Gln Gly Ile Lys Pro His Ile Arg Arg Met
 65                  70                  75                  80
Leu Asp Gln Gly Ile Leu Lys Pro Cys Gln Ser Pro Trp Asn Thr Pro
                 85                  90                  95
Leu Leu Pro Val Lys Lys Pro Gly Thr Lys Asp Tyr Arg Pro Val Gln
                100                 105                 110
Asp Leu Arg Glu Val Asn Lys Arg Val Glu Asp Ile His Pro Thr Val
                115                 120                 125
Pro Asn Pro Tyr Asn Leu Leu Ser Thr Leu Pro Pro Ser His Pro Trp
                130                 135                 140
Tyr Thr Val Leu Asp Leu Lys Asp Ala Phe Phe Cys Leu Arg Leu His
145                 150                 155                 160
Ser Glu Ser Gln Leu Leu Phe Ala Phe Glu Trp Arg Asp Pro Glu Ile
                165                 170                 175
Gly Leu Ser Gly Gln Leu Thr Trp Thr Arg Leu Pro Gln Gly Phe Lys
                180                 185                 190
Asn Ser Pro Thr Leu Phe Asp Glu Ala Leu His Ser Asp Leu Ala Asp
                195                 200                 205
Phe Arg Val Arg Tyr Pro Ala Leu Val Leu Leu Gln Tyr Val Asp Asp
210                 215                 220
Leu Leu Leu Ala Ala Ala Thr Arg Thr Glu Cys Leu Glu Gly Thr Lys
225                 230                 235                 240
Ala Leu Leu Glu Thr Leu Gly Asn Lys Gly Tyr Arg Ala Ser Ala Lys
                245                 250                 255
Lys Ala Gln Ile Cys Leu Gln Glu Val Thr Tyr Leu Gly Tyr Ser Leu
                260                 265                 270
Lys Asp Gly Gln Arg Trp Leu Thr Lys Ala Arg Lys Glu Ala Ile Leu
                275                 280                 285
Ser Ile Pro Val Pro Lys Asn Pro Arg Gln Val Arg Glu Phe Leu Gly
290                 295                 300
Thr Ala Gly Tyr Cys Arg Leu Trp Ile Pro Gly Phe Ala Glu Leu Ala
305                 310                 315                 320
Ala Pro Leu Tyr Pro Leu Thr Arg Pro Gly Thr Leu Phe Gln Trp Gly
                325                 330                 335
Thr Glu Gln Gln Leu Ala Phe Glu Asn Ile Arg Lys Ala Leu Leu Ser
                340                 345                 350
Ser Pro Ala Leu Gly Leu Pro Asp Ile Thr Lys Pro Phe Glu Leu Phe
                355                 360                 365
Ile Asp Glu Asn Ser Gly Phe Ala Lys Gly Val Leu Val Gln Lys Leu
                370                 375                 380
Gly Pro Trp Lys Arg Pro Val Ala Tyr Leu Ser Lys Lys Leu Asp Thr
385                 390                 395                 400
Val Ala Ser Gly Trp Pro Pro Cys Leu Arg Met Val Ala Ala Ile Ala
                405                 410                 415
Ile Leu Val Lys Asp Ala Gly Lys Leu Thr Leu Gly Gln Pro Leu Thr
                420                 425                 430
Ile Leu Thr Ser His Pro Val Glu Ala Leu Val Arg Gln Pro Pro Asn
                435                 440                 445
Lys Trp Leu Ser Asn Ala Arg Met Thr His Tyr Gln Ala Met Leu Leu
                450                 455                 460
```

Asp Ala Glu Arg Val His Phe Gly Pro Thr Val Ser Leu Asn Pro Ala
465                 470                 475                 480

Thr Leu Leu Pro Leu Pro Ser Gly Lys Pro Pro Arg Leu Ser Pro Asp
                485                 490                 495

Leu Ala Glu Thr Met Ala Gln Thr Asp Leu Thr Asp Gln Pro Leu Pro
            500                 505                 510

Asp Ala Asp Leu Thr Trp Tyr Thr Asp Gly Ser Ser Phe Ile Arg Asn
        515                 520                 525

Gly Glu Arg Lys Ala Gly Ala Ala Val Thr Thr Glu Ser Glu Val Ile
    530                 535                 540

Trp Ala Ala Ser Leu Pro Pro Gly Thr Ser Ala Gln Arg Ala Glu Leu
545                 550                 555                 560

Ile Ala Leu Thr Gln Ala Leu Lys Met Ala Lys Gly Lys Lys Leu Thr
                565                 570                 575

Val Tyr Thr Asp Ser Arg Tyr Ala Phe Ala Thr Ala His Val His Gly
            580                 585                 590

Glu Ile Tyr Arg Arg Arg Gly Leu Leu Thr Ser Glu Gly Lys Glu Ile
        595                 600                 605

Lys Asn Lys Asn Glu Ile Leu Ala Leu Leu Glu Ala Leu Phe Leu Pro
    610                 615                 620

Lys Arg Leu Ser Ile Ile His Cys Pro Gly His Gln Lys Gly Asp Ser
625                 630                 635                 640

Pro Gln Ala Lys Gly Asn Arg Leu Ala Asp Asp Thr Ala Lys Lys Ala
                645                 650                 655

Ala Thr Glu Thr Gln Ser Ser Leu Thr Ile Leu
            660                 665

<210> SEQ ID NO 3
<211> LENGTH: 1358
<212> TYPE: PRT
<213> ORGANISM: Artificial Sequence
<220> FEATURE:
<223> OTHER INFORMATION: Synthetic construct

<400> SEQUENCE: 3

Glu Phe Thr Leu Asn Ile Glu Asp Glu His Arg Leu His Glu Thr Ser
1               5                   10                  15

Lys Glu Pro Asp Val Ser Leu Gly Ser Thr Trp Leu Ser Asp Phe Pro
                20                  25                  30

Gln Ala Trp Ala Glu Thr Gly Gly Met Gly Leu Ala Val Arg Gln Ala
            35                  40                  45

Pro Leu Ile Ile Pro Leu Lys Ala Thr Ser Thr Pro Val Ser Ile Lys
        50                  55                  60

Gln Tyr Pro Met Ser Gln Glu Ala Arg Leu Gly Ile Lys Pro His Ile
65                  70                  75                  80

Gln Arg Leu Leu Asp Gln Gly Ile Leu Val Pro Cys Gln Ser Pro Trp
                85                  90                  95

Asn Thr Pro Leu Leu Pro Val Lys Lys Pro Gly Thr Asn Asp Tyr Arg
            100                 105                 110

Pro Val Gln Asp Leu Arg Glu Val Asn Lys Arg Val Glu Asp Ile His
        115                 120                 125

Pro Thr Val Pro Asn Pro Tyr Asn Leu Leu Ser Gly Leu Pro Pro Ser
    130                 135                 140

His Gln Trp Tyr Thr Val Leu Asp Leu Lys Asp Ala Phe Phe Cys Leu
145                 150                 155                 160

```
Arg Leu His Pro Thr Ser Gln Pro Leu Phe Ala Phe Glu Trp Arg Asp
                165                 170                 175

Pro Glu Met Gly Ile Ser Gly Gln Leu Thr Trp Thr Arg Leu Pro Gln
            180                 185                 190

Gly Phe Lys Asn Ser Pro Thr Leu Phe Asp Glu Ala Leu His Arg Asp
        195                 200                 205

Leu Ala Asp Phe Arg Ile Gln His Pro Asp Leu Ile Leu Leu Gln Tyr
    210                 215                 220

Val Asp Asp Leu Leu Leu Ala Thr Ser Glu Leu Asp Cys Gln Gln
225                 230                 235                 240

Gly Thr Arg Ala Leu Leu Gln Thr Leu Gly Asn Leu Gly Tyr Arg Ala
                245                 250                 255

Ser Ala Lys Lys Ala Gln Ile Cys Gln Lys Gln Val Lys Tyr Leu Gly
            260                 265                 270

Tyr Leu Leu Lys Glu Gly Gln Arg Trp Leu Thr Glu Ala Arg Lys Glu
        275                 280                 285

Thr Val Met Gly Gln Pro Thr Pro Lys Thr Pro Arg Gln Leu Arg Glu
    290                 295                 300

Phe Leu Gly Thr Ala Gly Phe Cys Arg Leu Trp Ile Pro Gly Phe Ala
305                 310                 315                 320

Glu Met Ala Ala Pro Leu Tyr Pro Leu Thr Lys Thr Gly Thr Leu Phe
                325                 330                 335

Asn Trp Gly Pro Asp Gln Gln Lys Ala Tyr Gln Glu Ile Lys Gln Ala
            340                 345                 350

Leu Leu Thr Ala Pro Ala Leu Gly Leu Pro Asp Leu Thr Lys Pro Phe
        355                 360                 365

Glu Leu Phe Val Asp Glu Lys Gln Gly Tyr Ala Lys Gly Val Leu Thr
    370                 375                 380

Gln Lys Leu Gly Pro Trp Arg Arg Pro Val Ala Tyr Leu Ser Lys Lys
385                 390                 395                 400

Leu Asp Pro Val Ala Ala Gly Trp Pro Pro Cys Leu Arg Met Val Ala
                405                 410                 415

Ala Ile Ala Val Leu Thr Lys Asp Ala Gly Lys Leu Thr Met Gly Gln
            420                 425                 430

Pro Leu Val Ile Leu Ala Pro His Ala Val Glu Ala Leu Val Lys Gln
        435                 440                 445

Pro Pro Asp Arg Trp Leu Ser Asn Ala Arg Met Thr His Tyr Gln Ala
    450                 455                 460

Leu Leu Leu Asp Thr Asp Arg Val Gln Phe Gly Pro Val Val Ala Leu
465                 470                 475                 480

Asn Pro Ala Thr Leu Leu Pro Leu Pro Glu Glu Gly Leu Gln His Asn
                485                 490                 495

Cys Leu Asp Ile Leu Ala Glu Ala His Gly Thr Arg Pro Asp Leu Thr
            500                 505                 510

Asp Gln Pro Leu Pro Asp Ala Asp His Thr Trp Tyr Thr Asp Gly Ser
        515                 520                 525

Ser Leu Leu Gln Glu Gly Gln Arg Lys Ala Gly Ala Ala Val Thr Thr
    530                 535                 540

Glu Thr Glu Val Ile Trp Ala Lys Ala Leu Pro Ala Gly Thr Ser Ala
545                 550                 555                 560

Gln Arg Ala Glu Leu Ile Ala Leu Thr Gln Ala Leu Lys Met Ala Glu
                565                 570                 575
```

```
Gly Lys Lys Leu Asn Val Tyr Thr Asp Ser Arg Tyr Ala Phe Ala Thr
            580                 585                 590
Ala His Ile His Gly Glu Ile Tyr Arg Arg Gly Leu Leu Thr Ser
        595                 600                 605
Glu Gly Lys Glu Ile Lys Asn Lys Asp Glu Ile Leu Ala Leu Leu Lys
    610                 615                 620
Ala Leu Phe Leu Pro Lys Arg Leu Ser Ile Ile His Cys Pro Gly His
625                 630                 635                 640
Gln Lys Gly His Ser Ala Glu Ala Arg Gly Asn Arg Met Ala Asp Gln
                645                 650                 655
Ala Ala Arg Lys Ala Ala Ile Thr Glu Thr Pro Asp Thr Ser Thr Leu
            660                 665                 670
Leu Ser Ser Ser Ala Ser Lys Leu Glu Phe Thr Leu Asn Ile Glu Asp
        675                 680                 685
Glu His Arg Leu His Glu Thr Ser Lys Glu Pro Asp Val Ser Leu Gly
    690                 695                 700
Ser Thr Trp Leu Ser Asp Phe Pro Gln Ala Trp Ala Glu Thr Gly Gly
705                 710                 715                 720
Met Gly Leu Ala Val Arg Gln Ala Pro Leu Ile Ile Pro Leu Lys Ala
                725                 730                 735
Thr Ser Thr Pro Val Ser Ile Lys Gln Tyr Pro Met Ser Gln Glu Ala
            740                 745                 750
Arg Leu Gly Ile Lys Pro His Ile Gln Arg Leu Leu Asp Gln Gly Ile
        755                 760                 765
Leu Val Pro Cys Gln Ser Pro Trp Asn Thr Pro Leu Leu Pro Val Lys
    770                 775                 780
Lys Pro Gly Thr Asn Asp Tyr Arg Pro Val Gln Asp Leu Arg Glu Val
785                 790                 795                 800
Asn Lys Arg Val Glu Asp Ile His Pro Thr Val Pro Asn Pro Tyr Asn
                805                 810                 815
Leu Leu Ser Gly Leu Pro Pro Ser His Gln Trp Tyr Thr Val Leu Asp
            820                 825                 830
Leu Lys Asp Ala Phe Phe Cys Leu Arg Leu His Pro Thr Ser Gln Pro
        835                 840                 845
Leu Phe Ala Phe Glu Trp Arg Asp Pro Glu Met Gly Ile Ser Gly Gln
    850                 855                 860
Leu Thr Trp Thr Arg Leu Pro Gln Gly Phe Lys Asn Ser Pro Thr Leu
865                 870                 875                 880
Phe Asp Glu Ala Leu His Arg Asp Leu Ala Asp Phe Arg Ile Gln His
                885                 890                 895
Pro Asp Leu Ile Leu Leu Gln Tyr Val Asp Asp Leu Leu Leu Ala Ala
            900                 905                 910
Thr Ser Glu Leu Asp Cys Gln Gln Gly Thr Arg Ala Leu Leu Gln Thr
        915                 920                 925
Leu Gly Asn Leu Gly Tyr Arg Ala Ser Ala Lys Lys Ala Gln Ile Cys
    930                 935                 940
Gln Lys Gln Val Lys Tyr Leu Gly Tyr Leu Leu Lys Glu Gly Gln Arg
945                 950                 955                 960
Trp Leu Thr Glu Ala Arg Lys Glu Thr Val Met Gly Gln Pro Thr Pro
                965                 970                 975
Lys Thr Pro Arg Gln Leu Arg Glu Phe Leu Gly Thr Ala Gly Phe Cys
            980                 985                 990
Arg Leu Trp Ile Pro Gly Phe Ala  Glu Met Ala Ala Pro Leu Tyr Pro
```

```
            995                 1000                1005
Leu Thr Lys Thr Gly Thr Leu Phe Asn Trp Gly Pro Asp Gln Gln
        1010                1015                1020

Lys Ala Tyr Gln Glu Ile Lys Gln Ala Leu Leu Thr Ala Pro Ala
        1025                1030                1035

Leu Gly Leu Pro Asp Leu Thr Lys Pro Phe Glu Leu Phe Val Asp
        1040                1045                1050

Glu Lys Gln Gly Tyr Ala Lys Gly Val Leu Thr Gln Lys Leu Gly
        1055                1060                1065

Pro Trp Arg Arg Pro Val Ala Tyr Leu Ser Lys Lys Leu Asp Pro
        1070                1075                1080

Val Ala Ala Gly Trp Pro Pro Cys Leu Arg Met Val Ala Ala Ile
        1085                1090                1095

Ala Val Leu Thr Lys Asp Ala Gly Lys Leu Thr Met Gly Gln Pro
        1100                1105                1110

Leu Val Ile Leu Ala Pro His Ala Val Glu Ala Leu Val Lys Gln
        1115                1120                1125

Pro Pro Asp Arg Trp Leu Ser Asn Ala Arg Met Thr His Tyr Gln
        1130                1135                1140

Ala Leu Leu Leu Asp Thr Asp Arg Val Gln Phe Gly Pro Val Val
        1145                1150                1155

Ala Leu Asn Pro Ala Thr Leu Leu Pro Leu Pro Glu Glu Gly Leu
        1160                1165                1170

Gln His Asn Cys Leu Asp Ile Leu Ala Glu Ala His Gly Thr Arg
        1175                1180                1185

Pro Asp Leu Thr Asp Gln Pro Leu Pro Asp Ala Asp His Thr Trp
        1190                1195                1200

Tyr Thr Asp Gly Ser Ser Leu Leu Gln Glu Gly Gln Arg Lys Ala
        1205                1210                1215

Gly Ala Ala Val Thr Thr Glu Thr Glu Val Ile Trp Ala Lys Ala
        1220                1225                1230

Leu Pro Ala Gly Thr Ser Ala Gln Arg Ala Glu Leu Ile Ala Leu
        1235                1240                1245

Thr Gln Ala Leu Lys Met Ala Glu Gly Lys Lys Leu Asn Val Tyr
        1250                1255                1260

Thr Asp Ser Arg Tyr Ala Phe Ala Thr Ala His Ile His Gly Glu
        1265                1270                1275

Ile Tyr Arg Arg Arg Gly Leu Leu Thr Ser Glu Gly Lys Glu Ile
        1280                1285                1290

Lys Asn Lys Asp Glu Ile Leu Ala Leu Leu Lys Ala Leu Phe Leu
        1295                1300                1305

Pro Lys Arg Leu Ser Ile Ile His Cys Pro Gly His Gln Lys Gly
        1310                1315                1320

His Ser Ala Glu Ala Arg Gly Asn Arg Met Ala Asp Gln Ala Ala
        1325                1330                1335

Arg Lys Ala Ala Ile Thr Glu Thr Pro Asp Thr Ser Thr Leu Leu
        1340                1345                1350

Ser Ser Ser Ala Ser
        1355

<210> SEQ ID NO 4
<211> LENGTH: 1358
<212> TYPE: PRT
<213> ORGANISM: Artificial Sequence
```

<220> FEATURE:
<223> OTHER INFORMATION: Synthetic construct

<400> SEQUENCE: 4

```
Glu Phe Thr Leu Asn Ile Glu Asp Glu His Arg Leu His Glu Thr Ser
1               5                   10                  15

Lys Glu Pro Asp Val Ser Leu Gly Ser Thr Trp Leu Ser Asp Phe Pro
            20                  25                  30

Gln Ala Trp Ala Glu Thr Gly Gly Met Gly Leu Ala Val Arg Gln Ala
        35                  40                  45

Pro Leu Ile Ile Pro Leu Lys Ala Thr Ser Thr Pro Val Ser Ile Lys
    50                  55                  60

Gln Tyr Pro Met Ser Gln Glu Ala Arg Leu Gly Ile Lys Pro His Ile
65                  70                  75                  80

Gln Arg Leu Leu Asp Gln Gly Ile Leu Val Pro Cys Gln Ser Pro Trp
                85                  90                  95

Asn Thr Pro Leu Leu Pro Val Lys Lys Pro Gly Thr Asn Asp Tyr Arg
            100                 105                 110

Pro Val Gln Asp Leu Arg Glu Val Asn Lys Arg Val Glu Asp Ile His
        115                 120                 125

Pro Thr Val Pro Asn Pro Tyr Asn Leu Leu Ser Gly Leu Pro Pro Ser
    130                 135                 140

His Gln Trp Tyr Thr Val Leu Asp Leu Lys Asp Ala Phe Phe Cys Leu
145                 150                 155                 160

Arg Leu His Pro Thr Ser Gln Pro Leu Phe Ala Phe Glu Trp Arg Asp
                165                 170                 175

Pro Glu Met Gly Ile Ser Gly Gln Leu Thr Trp Thr Arg Leu Pro Gln
            180                 185                 190

Gly Phe Lys Asn Ser Pro Thr Leu Phe Asp Glu Ala Leu His Arg Asp
        195                 200                 205

Leu Ala Asp Phe Arg Ile Gln His Pro Asp Leu Ile Leu Leu Gln Tyr
    210                 215                 220

Val Asp Asp Leu Leu Leu Ala Ala Thr Ser Glu Leu Asp Cys Gln Gln
225                 230                 235                 240

Gly Thr Arg Ala Leu Leu Gln Thr Leu Gly Asn Leu Gly Tyr Arg Ala
                245                 250                 255

Ser Ala Lys Lys Ala Gln Ile Cys Gln Lys Gln Val Lys Tyr Leu Gly
            260                 265                 270

Tyr Leu Leu Lys Glu Gly Gln Arg Trp Leu Thr Glu Ala Arg Lys Glu
        275                 280                 285

Thr Val Met Gly Gln Pro Thr Pro Lys Thr Pro Arg Gln Leu Arg Glu
    290                 295                 300

Phe Leu Gly Thr Ala Gly Phe Cys Arg Leu Trp Ile Pro Gly Phe Ala
305                 310                 315                 320

Glu Met Ala Ala Pro Leu Tyr Pro Leu Thr Lys Thr Gly Thr Leu Phe
                325                 330                 335

Asn Trp Gly Pro Asp Gln Gln Lys Ala Tyr Gln Glu Ile Lys Gln Ala
            340                 345                 350

Leu Leu Thr Ala Pro Ala Leu Gly Leu Pro Asp Leu Thr Lys Pro Phe
        355                 360                 365

Glu Leu Phe Val Asp Glu Lys Gln Gly Tyr Ala Lys Gly Val Leu Thr
    370                 375                 380

Gln Lys Leu Gly Pro Trp Arg Arg Pro Val Ala Tyr Leu Ser Lys Lys
385                 390                 395                 400
```

```
Leu Asp Pro Val Ala Ala Gly Trp Pro Pro Cys Leu Arg Met Val Ala
                405                 410                 415

Ala Ile Ala Val Leu Thr Lys Asp Ala Gly Lys Leu Thr Met Gly Gln
            420                 425                 430

Pro Leu Val Ile Leu Ala Pro His Ala Val Glu Ala Leu Val Lys Gln
                435                 440                 445

Pro Pro Asp Arg Trp Leu Ser Asn Ala Arg Met Thr His Tyr Gln Ala
450                 455                 460

Leu Leu Leu Asp Thr Asp Arg Val Gln Phe Gly Pro Val Val Ala Leu
465                 470                 475                 480

Asn Pro Ala Thr Leu Leu Pro Leu Pro Glu Glu Gly Leu Gln His Asn
                485                 490                 495

Cys Leu Asp Ile Leu Ala Glu Ala His Gly Thr Arg Pro Asp Leu Thr
                500                 505                 510

Asp Gln Pro Leu Pro Asp Ala Asp His Thr Trp Tyr Thr Asn Gly Ser
            515                 520                 525

Ser Leu Leu Gln Glu Gly Gln Arg Lys Ala Gly Ala Ala Val Thr Thr
            530                 535                 540

Glu Thr Glu Val Ile Trp Ala Lys Ala Leu Pro Ala Gly Thr Ser Ala
545                 550                 555                 560

Gln Arg Ala Glu Leu Ile Ala Leu Thr Gln Ala Leu Lys Met Ala Glu
                565                 570                 575

Gly Lys Lys Leu Asn Val Tyr Thr Asp Ser Arg Tyr Ala Phe Ala Thr
                580                 585                 590

Ala His Ile His Gly Glu Ile Tyr Arg Arg Arg Gly Leu Leu Thr Ser
            595                 600                 605

Glu Gly Lys Glu Ile Lys Asn Lys Asp Glu Ile Leu Ala Leu Leu Lys
610                 615                 620

Ala Leu Phe Leu Pro Lys Arg Leu Ser Ile Ile His Cys Pro Gly His
625                 630                 635                 640

Gln Lys Gly His Ser Ala Glu Ala Arg Gly Asn Arg Met Ala Asp Gln
                645                 650                 655

Ala Ala Arg Lys Ala Ala Ile Thr Glu Thr Pro Asp Thr Ser Thr Leu
                660                 665                 670

Leu Ser Ser Ser Ala Ser Lys Leu Glu Phe Thr Leu Asn Ile Glu Asp
            675                 680                 685

Glu His Arg Leu His Glu Thr Ser Lys Glu Pro Asp Val Ser Leu Gly
            690                 695                 700

Ser Thr Trp Leu Ser Asp Phe Pro Gln Ala Trp Ala Glu Thr Gly Gly
705                 710                 715                 720

Met Gly Leu Ala Val Arg Gln Ala Pro Leu Ile Ile Pro Leu Lys Ala
                725                 730                 735

Thr Ser Thr Pro Val Ser Ile Lys Gln Tyr Pro Met Ser Gln Glu Ala
                740                 745                 750

Arg Leu Gly Ile Lys Pro His Ile Gln Arg Leu Leu Asp Gln Gly Ile
            755                 760                 765

Leu Val Pro Cys Gln Ser Pro Trp Asn Thr Pro Leu Leu Pro Val Lys
770                 775                 780

Lys Pro Gly Thr Asn Asp Tyr Arg Pro Val Gln Asp Leu Arg Glu Val
785                 790                 795                 800

Asn Lys Arg Val Glu Asp Ile His Pro Thr Val Pro Asn Pro Tyr Asn
                805                 810                 815
```

-continued

Leu Leu Ser Gly Leu Pro Pro Ser His Gln Trp Tyr Thr Val Leu Asp
            820                 825                 830

Leu Lys Asp Ala Phe Phe Cys Leu Arg Leu His Pro Thr Ser Gln Pro
            835                 840                 845

Leu Phe Ala Phe Glu Trp Arg Asp Pro Glu Met Gly Ile Ser Gly Gln
            850                 855                 860

Leu Thr Trp Thr Arg Leu Pro Gln Gly Phe Lys Asn Ser Pro Thr Leu
865                 870                 875                 880

Phe Asp Glu Ala Leu His Arg Asp Leu Ala Asp Phe Arg Ile Gln His
                    885                 890                 895

Pro Asp Leu Ile Leu Leu Gln Tyr Val Asp Asp Leu Leu Leu Ala Ala
            900                 905                 910

Thr Ser Glu Leu Asp Cys Gln Gln Gly Thr Arg Ala Leu Leu Gln Thr
            915                 920                 925

Leu Gly Asn Leu Gly Tyr Arg Ala Ser Ala Lys Lys Ala Gln Ile Cys
            930                 935                 940

Gln Lys Gln Val Lys Tyr Leu Gly Tyr Leu Leu Lys Glu Gly Gln Arg
945                 950                 955                 960

Trp Leu Thr Glu Ala Arg Lys Glu Thr Val Met Gly Gln Pro Thr Pro
            965                 970                 975

Lys Thr Pro Arg Gln Leu Arg Glu Phe Leu Gly Thr Ala Gly Phe Cys
            980                 985                 990

Arg Leu Trp Ile Pro Gly Phe Ala Glu Met Ala Ala Pro Leu Tyr Pro
            995                 1000                1005

Leu Thr Lys Thr Gly Thr Leu Phe Asn Trp Gly Pro Asp Gln Gln
    1010                1015                1020

Lys Ala Tyr Gln Glu Ile Lys Gln Ala Leu Leu Thr Ala Pro Ala
    1025                1030                1035

Leu Gly Leu Pro Asp Leu Thr Lys Pro Phe Glu Leu Phe Val Asp
    1040                1045                1050

Glu Lys Gln Gly Tyr Ala Lys Gly Val Leu Thr Gln Lys Leu Gly
    1055                1060                1065

Pro Trp Arg Arg Pro Val Ala Tyr Leu Ser Lys Lys Leu Asp Pro
    1070                1075                1080

Val Ala Ala Gly Trp Pro Pro Cys Leu Arg Met Val Ala Ala Ile
    1085                1090                1095

Ala Val Leu Thr Lys Asp Ala Gly Lys Leu Thr Met Gly Gln Pro
    1100                1105                1110

Leu Val Ile Leu Ala Pro His Ala Val Glu Ala Leu Val Lys Gln
    1115                1120                1125

Pro Pro Asp Arg Trp Leu Ser Asn Ala Arg Met Thr His Tyr Gln
    1130                1135                1140

Ala Leu Leu Leu Asp Thr Asp Arg Val Gln Phe Gly Pro Val Val
    1145                1150                1155

Ala Leu Asn Pro Ala Thr Leu Leu Pro Leu Pro Glu Glu Gly Leu
    1160                1165                1170

Gln His Asn Cys Leu Asp Ile Leu Ala Glu Ala His Gly Thr Arg
    1175                1180                1185

Pro Asp Leu Thr Asp Gln Pro Leu Pro Asp Ala Asp His Thr Trp
    1190                1195                1200

Tyr Thr Asp Gly Ser Ser Leu Leu Gln Glu Gly Gln Arg Lys Ala
    1205                1210                1215

Gly Ala Ala Val Thr Thr Glu Thr Glu Val Ile Trp Ala Lys Ala

```
                1220                1225                1230

Leu Pro Ala Gly Thr Ser Ala   Gln Arg Ala Glu Leu   Ile Ala Leu
        1235                1240                1245

Thr Gln Ala Leu Lys Met Ala   Glu Gly Lys Lys Leu   Asn Val Tyr
        1250                1255                1260

Thr Asp Ser Arg Tyr Ala Phe   Ala Thr Ala His Ile   His Gly Glu
        1265                1270                1275

Ile Tyr Arg Arg Arg Gly Leu   Leu Thr Ser Glu Gly   Lys Glu Ile
        1280                1285                1290

Lys Asn Lys Asp Glu Ile Leu   Ala Leu Leu Lys Ala   Leu Phe Leu
        1295                1300                1305

Pro Lys Arg Leu Ser Ile Ile   His Cys Pro Gly His   Gln Lys Gly
        1310                1315                1320

His Ser Ala Glu Ala Arg Gly   Asn Arg Met Ala Asp   Gln Ala Ala
        1325                1330                1335

Arg Lys Ala Ala Ile Thr Glu   Thr Pro Asp Thr Ser   Thr Leu Leu
        1340                1345                1350

Ser Ser  Ser Ala Ser
        1355

<210> SEQ ID NO 5
<211> LENGTH: 1358
<212> TYPE: PRT
<213> ORGANISM: Artificial Sequence
<220> FEATURE:
<223> OTHER INFORMATION: Synthetic construct

<400> SEQUENCE: 5

Glu Phe Thr Leu Asn Ile Glu Asp Glu His Arg Leu His Glu Thr Ser
1               5                   10                  15

Lys Glu Pro Asp Val Ser Leu Gly Ser Thr Trp Leu Ser Asp Phe Pro
            20                  25                  30

Gln Ala Trp Ala Glu Thr Gly Gly Met Gly Leu Ala Val Arg Gln Ala
        35                  40                  45

Pro Leu Ile Ile Pro Leu Lys Ala Thr Ser Thr Pro Val Ser Ile Lys
    50                  55                  60

Gln Tyr Pro Met Ser Gln Glu Ala Arg Leu Gly Ile Lys Pro His Ile
65                  70                  75                  80

Gln Arg Leu Leu Asp Gln Gly Ile Leu Val Pro Cys Gln Ser Pro Trp
                85                  90                  95

Asn Thr Pro Leu Leu Pro Val Lys Lys Pro Gly Thr Asn Asp Tyr Arg
            100                 105                 110

Pro Val Gln Asp Leu Arg Glu Val Asn Lys Arg Val Glu Asp Ile His
        115                 120                 125

Pro Thr Val Pro Asn Pro Tyr Asn Leu Leu Ser Gly Leu Pro Pro Ser
    130                 135                 140

His Gln Trp Tyr Thr Val Leu Asp Leu Lys Asp Ala Phe Phe Cys Leu
145                 150                 155                 160

Arg Leu His Pro Thr Ser Gln Pro Leu Phe Ala Phe Glu Trp Arg Asp
                165                 170                 175

Pro Glu Met Gly Ile Ser Gly Gln Leu Thr Trp Thr Arg Leu Pro Gln
            180                 185                 190

Gly Phe Lys Asn Ser Pro Thr Leu Phe Asp Glu Ala Leu His Arg Asp
        195                 200                 205

Leu Ala Asp Phe Arg Ile Gln His Pro Asp Leu Ile Leu Leu Gln Tyr
```

-continued

```
                210                 215                 220
Val Asp Asp Leu Leu Leu Ala Ala Thr Ser Glu Leu Asp Cys Gln Gln
225                 230                 235                 240

Gly Thr Arg Ala Leu Leu Gln Thr Leu Gly Asn Leu Gly Tyr Arg Ala
                245                 250                 255

Ser Ala Lys Lys Ala Gln Ile Cys Gln Lys Gln Val Lys Tyr Leu Gly
                260                 265                 270

Tyr Leu Leu Lys Glu Gly Gln Arg Trp Leu Thr Glu Ala Arg Lys Glu
                275                 280                 285

Thr Val Met Gly Gln Pro Thr Pro Lys Thr Pro Arg Gln Leu Arg Glu
290                 295                 300

Phe Leu Gly Thr Ala Gly Phe Cys Arg Leu Trp Ile Pro Gly Phe Ala
305                 310                 315                 320

Glu Met Ala Ala Pro Leu Tyr Pro Leu Thr Lys Thr Gly Thr Leu Phe
                325                 330                 335

Asn Trp Gly Pro Asp Gln Gln Lys Ala Tyr Gln Glu Ile Lys Gln Ala
                340                 345                 350

Leu Leu Thr Ala Pro Ala Leu Gly Leu Pro Asp Leu Thr Lys Pro Phe
                355                 360                 365

Glu Leu Phe Val Asp Glu Lys Gln Gly Tyr Ala Lys Gly Val Leu Thr
                370                 375                 380

Gln Lys Leu Gly Pro Trp Arg Arg Pro Val Ala Tyr Leu Ser Lys Lys
385                 390                 395                 400

Leu Asp Pro Val Ala Ala Gly Trp Pro Pro Cys Leu Arg Met Val Ala
                405                 410                 415

Ala Ile Ala Val Leu Thr Lys Asp Ala Gly Lys Leu Thr Met Gly Gln
                420                 425                 430

Pro Leu Val Ile Leu Ala Pro His Ala Val Glu Ala Leu Val Lys Gln
                435                 440                 445

Pro Pro Asp Arg Trp Leu Ser Asn Ala Arg Met Thr His Tyr Gln Ala
                450                 455                 460

Leu Leu Leu Asp Thr Asp Arg Val Gln Phe Gly Pro Val Val Ala Leu
465                 470                 475                 480

Asn Pro Ala Thr Leu Leu Pro Leu Pro Glu Glu Gly Leu Gln His Asn
                485                 490                 495

Cys Leu Asp Ile Leu Ala Glu Ala His Gly Thr Arg Pro Asp Leu Thr
                500                 505                 510

Asp Gln Pro Leu Pro Asp Ala Asp His Thr Trp Tyr Thr Asn Gly Ser
                515                 520                 525

Ser Leu Leu Gln Glu Gly Gln Arg Lys Ala Gly Ala Ala Val Thr Thr
                530                 535                 540

Glu Thr Glu Val Ile Trp Ala Lys Ala Leu Pro Ala Gly Thr Ser Ala
545                 550                 555                 560

Gln Arg Ala Glu Leu Ile Ala Leu Thr Gln Ala Leu Lys Met Ala Glu
                565                 570                 575

Gly Lys Lys Leu Asn Val Tyr Thr Asp Ser Arg Tyr Ala Phe Ala Thr
                580                 585                 590

Ala His Ile His Gly Glu Ile Tyr Arg Arg Gly Leu Leu Thr Ser
                595                 600                 605

Glu Gly Lys Glu Ile Lys Asn Lys Asp Glu Ile Leu Ala Leu Leu Lys
                610                 615                 620

Ala Leu Phe Leu Pro Lys Arg Leu Ser Ile Ile His Cys Pro Gly His
625                 630                 635                 640
```

```
Gln Lys Gly His Ser Ala Glu Ala Arg Gly Asn Arg Met Ala Asp Gln
                645                 650                 655

Ala Ala Arg Lys Ala Ala Ile Thr Glu Thr Pro Asp Thr Ser Thr Leu
            660                 665                 670

Leu Ser Ser Ser Ala Ser Lys Leu Glu Phe Thr Leu Asn Ile Glu Asp
        675                 680                 685

Glu His Arg Leu His Glu Thr Ser Lys Glu Pro Asp Val Ser Leu Gly
    690                 695                 700

Ser Thr Trp Leu Ser Asp Phe Pro Gln Ala Trp Ala Glu Thr Gly Gly
705                 710                 715                 720

Met Gly Leu Ala Val Arg Gln Ala Pro Leu Ile Pro Leu Lys Ala
                725                 730                 735

Thr Ser Thr Pro Val Ser Ile Lys Gln Tyr Pro Met Ser Gln Glu Ala
            740                 745                 750

Arg Leu Gly Ile Lys Pro His Ile Gln Arg Leu Leu Asp Gln Gly Ile
        755                 760                 765

Leu Val Pro Cys Gln Ser Pro Trp Asn Thr Pro Leu Leu Pro Val Lys
    770                 775                 780

Lys Pro Gly Thr Asn Asp Tyr Arg Pro Val Gln Asp Leu Arg Glu Val
785                 790                 795                 800

Asn Lys Arg Val Glu Asp Ile His Pro Thr Val Pro Asn Pro Tyr Asn
                805                 810                 815

Leu Leu Ser Gly Leu Pro Pro Ser His Gln Trp Tyr Thr Val Leu Asp
            820                 825                 830

Leu Lys Asp Ala Phe Phe Cys Leu Arg Leu His Pro Thr Ser Gln Pro
        835                 840                 845

Leu Phe Ala Phe Glu Trp Arg Asp Pro Glu Met Gly Ile Ser Gly Gln
    850                 855                 860

Leu Thr Trp Thr Arg Leu Pro Gln Gly Phe Lys Asn Ser Pro Thr Leu
865                 870                 875                 880

Phe Asp Glu Ala Leu His Arg Asp Leu Ala Asp Phe Arg Ile Gln His
                885                 890                 895

Pro Asp Leu Ile Leu Leu Gln Tyr Val Asp Asp Leu Leu Leu Ala Ala
            900                 905                 910

Thr Ser Glu Leu Asp Cys Gln Gln Gly Thr Arg Ala Leu Leu Gln Thr
        915                 920                 925

Leu Gly Asn Leu Gly Tyr Arg Ala Ser Ala Lys Lys Ala Gln Ile Cys
    930                 935                 940

Gln Lys Gln Val Lys Tyr Leu Gly Tyr Leu Leu Lys Glu Gly Gln Arg
945                 950                 955                 960

Trp Leu Thr Glu Ala Arg Lys Glu Thr Val Met Gly Gln Pro Thr Pro
                965                 970                 975

Lys Thr Pro Arg Gln Leu Arg Glu Phe Leu Gly Thr Ala Gly Phe Cys
            980                 985                 990

Arg Leu Trp Ile Pro Gly Phe Ala  Glu Met Ala Ala Pro  Leu Tyr Pro
        995                 1000                1005

Leu Thr Lys Thr Gly Thr Leu  Phe Asn Trp Gly Pro  Asp Gln Gln
    1010                1015                1020

Lys Ala  Tyr Gln Glu Ile Lys  Gln Ala Leu Leu Thr  Ala Pro Ala
    1025                1030                1035

Leu Gly  Leu Pro Asp Leu Thr  Lys Pro Phe Glu Leu  Phe Val Asp
    1040                1045                1050
```

```
Glu Lys Gln Gly Tyr Ala Lys Gly Val Leu Thr Gln Lys Leu Gly
    1055                1060                1065

Pro Trp Arg Arg Pro Val Ala Tyr Leu Ser Lys Lys Leu Asp Pro
    1070                1075                1080

Val Ala Ala Gly Trp Pro Pro Cys Leu Arg Met Val Ala Ala Ile
    1085                1090                1095

Ala Val Leu Thr Lys Asp Ala Gly Lys Leu Thr Met Gly Gln Pro
    1100                1105                1110

Leu Val Ile Leu Ala Pro His Ala Val Glu Ala Leu Val Lys Gln
    1115                1120                1125

Pro Pro Asp Arg Trp Leu Ser Asn Ala Arg Met Thr His Tyr Gln
    1130                1135                1140

Ala Leu Leu Leu Asp Thr Asp Arg Val Gln Phe Gly Pro Val Val
    1145                1150                1155

Ala Leu Asn Pro Ala Thr Leu Leu Pro Leu Pro Glu Glu Gly Leu
    1160                1165                1170

Gln His Asn Cys Leu Asp Ile Leu Ala Glu Ala His Gly Thr Arg
    1175                1180                1185

Pro Asp Leu Thr Asp Gln Pro Leu Pro Asp Ala Asp His Thr Trp
    1190                1195                1200

Tyr Thr Asn Gly Ser Ser Leu Leu Gln Glu Gly Gln Arg Lys Ala
    1205                1210                1215

Gly Ala Ala Val Thr Thr Glu Thr Glu Val Ile Trp Ala Lys Ala
    1220                1225                1230

Leu Pro Ala Gly Thr Ser Ala Gln Arg Ala Glu Leu Ile Ala Leu
    1235                1240                1245

Thr Gln Ala Leu Lys Met Ala Glu Gly Lys Lys Leu Asn Val Tyr
    1250                1255                1260

Thr Asp Ser Arg Tyr Ala Phe Ala Thr Ala His Ile His Gly Glu
    1265                1270                1275

Ile Tyr Arg Arg Arg Gly Leu Leu Thr Ser Glu Gly Lys Glu Ile
    1280                1285                1290

Lys Asn Lys Asp Glu Ile Leu Ala Leu Leu Lys Ala Leu Phe Leu
    1295                1300                1305

Pro Lys Arg Leu Ser Ile Ile His Cys Pro Gly His Gln Lys Gly
    1310                1315                1320

His Ser Ala Glu Ala Arg Gly Asn Arg Met Ala Asp Gln Ala Ala
    1325                1330                1335

Arg Lys Ala Ala Ile Thr Glu Thr Pro Asp Thr Ser Thr Leu Leu
    1340                1345                1350

Ser Ser Ser Ala Ser
    1355

<210> SEQ ID NO 6
<211> LENGTH: 1350
<212> TYPE: PRT
<213> ORGANISM: Artificial Sequence
<220> FEATURE:
<223> OTHER INFORMATION: Synthetic construct

<400> SEQUENCE: 6

Glu Phe Thr Leu Gln Leu Glu Glu Glu Tyr Arg Leu Phe Glu Pro Glu
1               5                   10                  15

Ser Thr Gln Lys Gln Glu Met Asp Ile Trp Leu Lys Asn Phe Pro Gln
            20                  25                  30
```

-continued

Ala Trp Ala Glu Thr Gly Gly Met Gly Met Ala His Cys Gln Ala Pro
             35                  40                  45

Val Leu Ile Gln Leu Lys Ala Thr Ala Thr Pro Ile Ser Ile Arg Gln
 50                  55                  60

Tyr Pro Met Pro His Glu Ala Tyr Gln Gly Ile Lys Pro His Ile Arg
 65                  70                  75                  80

Arg Met Leu Asp Gln Gly Ile Leu Lys Pro Cys Gln Ser Pro Trp Asn
                 85                  90                  95

Thr Pro Leu Leu Pro Val Lys Lys Pro Gly Thr Lys Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Thr Leu Pro Pro Ser His
130                 135                 140

Pro Trp Tyr Thr Val Leu Asp Leu Lys Asp Ala Phe Phe Cys Leu Arg
145                 150                 155                 160

Leu His Ser Glu Ser Gln Leu Leu Phe Ala Phe Glu Trp Arg Asp Pro
                165                 170                 175

Glu Ile Gly Leu Ser Gly Gln Leu Thr Trp Thr Arg Leu Pro Gln Gly
                180                 185                 190

Phe Lys Asn Ser Pro Thr Leu Phe Asp Glu Ala Leu His Ser Asp Leu
            195                 200                 205

Ala Asp Phe Arg Val Arg Tyr Pro Ala Leu Val Leu Leu Gln Tyr Val
        210                 215                 220

Asp Asp Leu Leu Leu Ala Ala Thr Arg Thr Glu Cys Leu Glu Gly
225                 230                 235                 240

Thr Lys Ala Leu Leu Glu Thr Leu Gly Asn Lys Gly Tyr Arg Ala Ser
                245                 250                 255

Ala Lys Lys Ala Gln Ile Cys Leu Gln Glu Val Thr Tyr Leu Gly Tyr
            260                 265                 270

Ser Leu Lys Asp Gly Gln Arg Trp Leu Thr Lys Ala Arg Lys Glu Ala
        275                 280                 285

Ile Leu Ser Ile Pro Val Pro Lys Asn Pro Arg Gln Val Arg Glu Phe
    290                 295                 300

Leu Gly Thr Ala Gly Tyr Cys Arg Leu Trp Ile Pro Gly Phe Ala Glu
305                 310                 315                 320

Leu Ala Ala Pro Leu Tyr Pro Leu Thr Arg Pro Gly Thr Leu Phe Gln
                325                 330                 335

Trp Gly Thr Glu Gln Gln Leu Ala Phe Glu Asn Ile Arg Lys Ala Leu
            340                 345                 350

Leu Ser Ser Pro Ala Leu Gly Leu Pro Asp Ile Thr Lys Pro Phe Glu
        355                 360                 365

Leu Phe Ile Asp Glu Asn Ser Gly Phe Ala Lys Gly Val Leu Val Gln
    370                 375                 380

Lys Leu Gly Pro Trp Lys Arg Pro Val Ala Tyr Leu Ser Lys Lys Leu
385                 390                 395                 400

Asp Thr Val Ala Ser Gly Trp Pro Pro Cys Leu Arg Met Val Ala Ala
                405                 410                 415

Ile Ala Ile Leu Val Lys Asp Ala Gly Lys Leu Thr Leu Gly Gln Pro
            420                 425                 430

Leu Thr Ile Leu Thr Ser His Pro Val Glu Ala Leu Val Arg Gln Pro
        435                 440                 445

Pro Asn Lys Trp Leu Ser Asn Ala Arg Met Thr His Tyr Gln Ala Met

```
                450                 455                 460
Leu Leu Asp Ala Glu Arg Val His Phe Gly Pro Thr Val Ser Leu Asn
465                 470                 475                 480

Pro Ala Thr Leu Leu Pro Leu Pro Ser Gly Lys Pro Pro Arg Leu Ser
                485                 490                 495

Pro Asp Leu Ala Glu Thr Met Ala Gln Thr Asp Leu Thr Asp Gln Pro
                500                 505                 510

Leu Pro Asp Ala Asp Leu Thr Trp Tyr Thr Asp Gly Ser Ser Phe Ile
                515                 520                 525

Arg Asn Gly Glu Arg Lys Ala Gly Ala Ala Val Thr Thr Glu Ser Glu
                530                 535                 540

Val Ile Trp Ala Ala Ser Leu Pro Pro Gly Thr Ser Ala Gln Arg Ala
545                 550                 555                 560

Glu Leu Ile Ala Leu Thr Gln Ala Leu Lys Met Ala Lys Gly Lys Lys
                565                 570                 575

Leu Thr Val Tyr Thr Asp Ser Arg Tyr Ala Phe Ala Thr Ala His Val
                580                 585                 590

His Gly Glu Ile Tyr Arg Arg Arg Gly Leu Leu Thr Ser Glu Gly Lys
                595                 600                 605

Glu Ile Lys Asn Lys Asn Glu Ile Leu Ala Leu Leu Glu Ala Leu Phe
                610                 615                 620

Leu Pro Lys Arg Leu Ser Ile Ile His Cys Pro Gly His Gln Lys Gly
625                 630                 635                 640

Asp Ser Pro Gln Ala Lys Gly Asn Arg Leu Ala Asp Asp Thr Ala Lys
                645                 650                 655

Lys Ala Ala Thr Glu Thr Gln Ser Ser Leu Thr Ile Leu Ser Ser Ser
                660                 665                 670

Ala Ser Lys Leu Glu Phe Thr Leu Gln Leu Glu Glu Tyr Arg Leu
                675                 680                 685

Phe Glu Pro Glu Ser Thr Gln Lys Gln Glu Met Asp Ile Trp Leu Lys
                690                 695                 700

Asn Phe Pro Gln Ala Trp Ala Glu Thr Gly Gly Met Gly Met Ala His
705                 710                 715                 720

Cys Gln Ala Pro Val Leu Ile Gln Leu Lys Ala Thr Ala Thr Pro Ile
                725                 730                 735

Ser Ile Arg Gln Tyr Pro Met Pro His Glu Ala Tyr Gln Gly Ile Lys
                740                 745                 750

Pro His Ile Arg Arg Met Leu Asp Gln Gly Ile Leu Lys Pro Cys Gln
                755                 760                 765

Ser Pro Trp Asn Thr Pro Leu Leu Pro Val Lys Lys Pro Gly Thr Lys
                770                 775                 780

Asp Tyr Arg Pro Val Gln Asp Leu Arg Glu Val Asn Lys Arg Val Glu
785                 790                 795                 800

Asp Ile His Pro Thr Val Pro Asn Pro Tyr Asn Leu Leu Ser Thr Leu
                805                 810                 815

Pro Pro Ser His Pro Trp Tyr Thr Val Leu Asp Leu Lys Asp Ala Phe
                820                 825                 830

Phe Cys Leu Arg Leu His Ser Glu Ser Gln Leu Leu Phe Ala Phe Glu
                835                 840                 845

Trp Arg Asp Pro Glu Ile Gly Leu Ser Gly Gln Leu Thr Trp Thr Arg
                850                 855                 860

Leu Pro Gln Gly Phe Lys Asn Ser Pro Thr Leu Phe Asp Glu Ala Leu
865                 870                 875                 880
```

```
His Ser Asp Leu Ala Asp Phe Arg Val Arg Tyr Pro Ala Leu Val Leu
                885                 890                 895

Leu Gln Tyr Val Asp Asp Leu Leu Ala Ala Ala Thr Arg Thr Glu
            900                 905                 910

Cys Leu Glu Gly Thr Lys Ala Leu Leu Glu Thr Leu Gly Asn Lys Gly
            915                 920                 925

Tyr Arg Ala Ser Ala Lys Lys Ala Gln Ile Cys Leu Gln Glu Val Thr
            930                 935                 940

Tyr Leu Gly Tyr Ser Leu Lys Asp Gly Gln Arg Trp Leu Thr Lys Ala
945                 950                 955                 960

Arg Lys Glu Ala Ile Leu Ser Ile Pro Val Pro Lys Asn Pro Arg Gln
                965                 970                 975

Val Arg Glu Phe Leu Gly Thr Ala Gly Tyr Cys Arg Leu Trp Ile Pro
            980                 985                 990

Gly Phe Ala Glu Leu Ala Ala Pro Leu Tyr Pro Leu Thr Arg Pro Gly
            995                 1000                1005

Thr Leu Phe Gln Trp Gly Thr Glu Gln Gln Leu Ala Phe Glu Asn
        1010                1015                1020

Ile Arg Lys Ala Leu Leu Ser Ser Pro Ala Leu Gly Leu Pro Asp
        1025                1030                1035

Ile Thr Lys Pro Phe Glu Leu Phe Ile Asp Glu Asn Ser Gly Phe
        1040                1045                1050

Ala Lys Gly Val Leu Val Gln Lys Leu Gly Pro Trp Lys Arg Pro
        1055                1060                1065

Val Ala Tyr Leu Ser Lys Lys Leu Asp Thr Val Ala Ser Gly Trp
        1070                1075                1080

Pro Pro Cys Leu Arg Met Val Ala Ala Ile Ala Ile Leu Val Lys
        1085                1090                1095

Asp Ala Gly Lys Leu Thr Leu Gly Gln Pro Leu Thr Ile Leu Thr
        1100                1105                1110

Ser His Pro Val Glu Ala Leu Val Arg Gln Pro Pro Asn Lys Trp
        1115                1120                1125

Leu Ser Asn Ala Arg Met Thr His Tyr Gln Ala Met Leu Leu Asp
        1130                1135                1140

Ala Glu Arg Val His Phe Gly Pro Thr Val Ser Leu Asn Pro Ala
        1145                1150                1155

Thr Leu Leu Pro Leu Pro Ser Gly Lys Pro Pro Arg Leu Ser Pro
        1160                1165                1170

Asp Leu Ala Glu Thr Met Ala Gln Thr Asp Leu Thr Asp Gln Pro
        1175                1180                1185

Leu Pro Asp Ala Asp Leu Thr Trp Tyr Thr Asp Gly Ser Ser Phe
        1190                1195                1200

Ile Arg Asn Gly Glu Arg Lys Ala Gly Ala Ala Val Thr Thr Glu
        1205                1210                1215

Ser Glu Val Ile Trp Ala Ala Ser Leu Pro Pro Gly Thr Ser Ala
        1220                1225                1230

Gln Arg Ala Glu Leu Ile Ala Leu Thr Gln Ala Leu Lys Met Ala
        1235                1240                1245

Lys Gly Lys Lys Leu Thr Val Tyr Thr Asp Ser Arg Tyr Ala Phe
        1250                1255                1260

Ala Thr Ala His Val His Gly Glu Ile Tyr Arg Arg Arg Gly Leu
        1265                1270                1275
```

-continued

Leu Thr Ser Glu Gly Lys Glu Ile Lys Asn Lys Asn Glu Ile Leu
    1280            1285                1290

Ala Leu Leu Glu Ala Leu Phe Leu Pro Lys Arg Leu Ser Ile Ile
    1295            1300                1305

His Cys Pro Gly His Gln Lys Gly Asp Ser Pro Gln Ala Lys Gly
    1310            1315                1320

Asn Arg Leu Ala Asp Asp Thr Ala Lys Lys Ala Ala Thr Glu Thr
    1325            1330                1335

Gln Ser Ser Leu Thr Ile Leu Ser Ser Ser Ala Ser
    1340            1345                1350

<210> SEQ ID NO 7
<211> LENGTH: 1350
<212> TYPE: PRT
<213> ORGANISM: Artificial Sequence
<220> FEATURE:
<223> OTHER INFORMATION: Synthetic construct

<400> SEQUENCE: 7

Glu Phe Thr Leu Gln Leu Glu Glu Glu Tyr Arg Leu Phe Glu Pro Glu
1               5                   10                  15

Ser Thr Gln Lys Gln Glu Met Asp Ile Trp Leu Lys Asn Phe Pro Gln
            20                  25                  30

Ala Trp Ala Glu Thr Gly Gly Met Gly Met Ala His Cys Gln Ala Pro
        35                  40                  45

Val Leu Ile Gln Leu Lys Ala Thr Ala Thr Pro Ile Ser Ile Arg Gln
    50                  55                  60

Tyr Pro Met Pro His Glu Ala Tyr Gln Gly Ile Lys Pro His Ile Arg
65                  70                  75                  80

Arg Met Leu Asp Gln Gly Ile Leu Lys Pro Cys Gln Ser Pro Trp Asn
                85                  90                  95

Thr Pro Leu Leu Pro Val Lys Lys Pro Gly Thr Lys Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Thr Leu Pro Pro Ser His
    130                 135                 140

Pro Trp Tyr Thr Val Leu Asp Leu Lys Asp Ala Phe Phe Cys Leu Arg
145                 150                 155                 160

Leu His Ser Glu Ser Gln Leu Leu Phe Ala Phe Glu Trp Arg Asp Pro
                165                 170                 175

Glu Ile Gly Leu Ser Gly Gln Leu Thr Trp Thr Arg Leu Pro Gln Gly
            180                 185                 190

Phe Lys Asn Ser Pro Thr Leu Phe Asp Glu Ala Leu His Ser Asp Leu
        195                 200                 205

Ala Asp Phe Arg Val Arg Tyr Pro Ala Leu Val Leu Leu Gln Tyr Val
    210                 215                 220

Asp Asp Leu Leu Leu Ala Ala Thr Arg Thr Glu Cys Leu Glu Gly
225                 230                 235                 240

Thr Lys Ala Leu Leu Glu Thr Leu Gly Asn Lys Gly Tyr Arg Ala Ser
                245                 250                 255

Ala Lys Lys Ala Gln Ile Cys Leu Gln Glu Val Thr Tyr Leu Gly Tyr
            260                 265                 270

Ser Leu Lys Asp Gly Gln Arg Trp Leu Thr Lys Ala Arg Lys Glu Ala
        275                 280                 285

```
Ile Leu Ser Ile Pro Val Pro Lys Asn Pro Arg Gln Val Arg Glu Phe
290                 295                 300

Leu Gly Thr Ala Gly Tyr Cys Arg Leu Trp Ile Pro Gly Phe Ala Glu
305                 310                 315                 320

Leu Ala Ala Pro Leu Tyr Pro Leu Thr Arg Pro Gly Thr Leu Phe Gln
            325                 330                 335

Trp Gly Thr Glu Gln Gln Leu Ala Phe Glu Asn Ile Arg Lys Ala Leu
        340                 345                 350

Leu Ser Ser Pro Ala Leu Gly Leu Pro Asp Ile Thr Lys Pro Phe Glu
    355                 360                 365

Leu Phe Ile Asp Glu Asn Ser Gly Phe Ala Lys Gly Val Leu Gln
370                 375                 380

Lys Leu Gly Pro Trp Lys Arg Pro Val Ala Tyr Leu Ser Lys Lys Leu
385                 390                 395                 400

Asp Thr Val Ala Ser Gly Trp Pro Pro Cys Leu Arg Met Val Ala Ala
            405                 410                 415

Ile Ala Ile Leu Val Lys Asp Ala Gly Lys Leu Thr Leu Gly Gln Pro
            420                 425                 430

Leu Thr Ile Leu Thr Ser His Pro Val Glu Ala Leu Val Arg Gln Pro
            435                 440                 445

Pro Asn Lys Trp Leu Ser Asn Ala Arg Met Thr His Tyr Gln Ala Met
450                 455                 460

Leu Leu Asp Ala Glu Arg Val His Phe Gly Pro Thr Val Ser Leu Asn
465                 470                 475                 480

Pro Ala Thr Leu Leu Pro Leu Pro Ser Gly Lys Pro Pro Arg Leu Ser
            485                 490                 495

Pro Asp Leu Ala Glu Thr Met Ala Gln Thr Asp Leu Thr Asp Gln Pro
            500                 505                 510

Leu Pro Asp Ala Asp Leu Thr Trp Tyr Thr Asn Gly Ser Ser Phe Ile
    515                 520                 525

Arg Asn Gly Glu Arg Lys Ala Gly Ala Ala Val Thr Thr Glu Ser Glu
530                 535                 540

Val Ile Trp Ala Ala Ser Leu Pro Pro Gly Thr Ser Ala Gln Arg Ala
545                 550                 555                 560

Glu Leu Ile Ala Leu Thr Gln Ala Leu Lys Met Ala Lys Gly Lys Lys
            565                 570                 575

Leu Thr Val Tyr Thr Asp Ser Arg Tyr Ala Phe Ala Thr Ala His Val
            580                 585                 590

His Gly Glu Ile Tyr Arg Arg Arg Gly Leu Leu Thr Ser Glu Gly Lys
    595                 600                 605

Glu Ile Lys Asn Lys Asn Glu Ile Leu Ala Leu Leu Glu Ala Leu Phe
610                 615                 620

Leu Pro Lys Arg Leu Ser Ile Ile His Cys Pro Gly His Gln Lys Gly
625                 630                 635                 640

Asp Ser Pro Gln Ala Lys Gly Asn Arg Leu Ala Asp Asp Thr Ala Lys
            645                 650                 655

Lys Ala Ala Thr Glu Thr Gln Ser Ser Leu Thr Ile Leu Ser Ser Ser
            660                 665                 670

Ala Ser Lys Leu Glu Phe Thr Leu Gln Leu Glu Glu Tyr Arg Leu
    675                 680                 685

Phe Glu Pro Glu Ser Thr Gln Lys Gln Glu Met Asp Ile Trp Leu Lys
690                 695                 700

Asn Phe Pro Gln Ala Trp Ala Glu Thr Gly Gly Met Gly Met Ala His
```

-continued

```
                705                 710                 715                 720
Cys Gln Ala Pro Val Leu Ile Gln Leu Lys Ala Thr Ala Thr Pro Ile
                    725                 730                 735
Ser Ile Arg Gln Tyr Pro Met Pro His Glu Ala Tyr Gln Gly Ile Lys
                    740                 745                 750
Pro His Ile Arg Arg Met Leu Asp Gln Gly Ile Leu Lys Pro Cys Gln
                    755                 760                 765
Ser Pro Trp Asn Thr Pro Leu Leu Pro Val Lys Pro Gly Thr Lys
    770                 775                 780
Asp Tyr Arg Pro Val Gln Asp Leu Arg Glu Val Asn Lys Arg Val Glu
785                 790                 795                 800
Asp Ile His Pro Thr Val Pro Asn Pro Tyr Asn Leu Leu Ser Thr Leu
                    805                 810                 815
Pro Pro Ser His Pro Trp Tyr Thr Val Leu Asp Leu Lys Asp Ala Phe
                    820                 825                 830
Phe Cys Leu Arg Leu His Ser Glu Ser Gln Leu Leu Phe Ala Phe Glu
                    835                 840                 845
Trp Arg Asp Pro Glu Ile Gly Leu Ser Gly Gln Leu Thr Trp Thr Arg
850                 855                 860
Leu Pro Gln Gly Phe Lys Asn Ser Pro Thr Leu Phe Asp Glu Ala Leu
865                 870                 875                 880
His Ser Asp Leu Ala Asp Phe Arg Val Arg Tyr Pro Ala Leu Val Leu
                    885                 890                 895
Leu Gln Tyr Val Asp Asp Leu Leu Leu Ala Ala Ala Thr Arg Thr Glu
                    900                 905                 910
Cys Leu Glu Gly Thr Lys Ala Leu Leu Glu Thr Leu Gly Asn Lys Gly
                    915                 920                 925
Tyr Arg Ala Ser Ala Lys Lys Ala Gln Ile Cys Leu Gln Glu Val Thr
                    930                 935                 940
Tyr Leu Gly Tyr Ser Leu Lys Asp Gly Gln Arg Trp Leu Thr Lys Ala
945                 950                 955                 960
Arg Lys Glu Ala Ile Leu Ser Ile Pro Val Pro Lys Asn Pro Arg Gln
                    965                 970                 975
Val Arg Glu Phe Leu Gly Thr Ala Gly Tyr Cys Arg Leu Trp Ile Pro
                    980                 985                 990
Gly Phe Ala Glu Leu Ala Ala Pro Leu Tyr Pro Leu Thr Arg Pro Gly
                    995                 1000                1005
Thr Leu Phe Gln Trp Gly Glu Gln Gln Leu Ala Phe Glu Asn
                    1010                1015                1020
Ile Arg Lys Ala Leu Leu Ser Ser Pro Ala Leu Gly Leu Pro Asp
                    1025                1030                1035
Ile Thr Lys Pro Phe Glu Leu Phe Ile Asp Glu Asn Ser Gly Phe
                    1040                1045                1050
Ala Lys Gly Val Leu Val Gln Lys Leu Gly Pro Trp Lys Arg Pro
                    1055                1060                1065
Val Ala Tyr Leu Ser Lys Lys Leu Asp Thr Val Ala Ser Gly Trp
                    1070                1075                1080
Pro Pro Cys Leu Arg Met Val Ala Ala Ile Ala Ile Leu Val Lys
                    1085                1090                1095
Asp Ala Gly Lys Leu Thr Leu Gly Gln Pro Leu Thr Ile Leu Thr
                    1100                1105                1110
Ser His Pro Val Glu Ala Leu Val Arg Gln Pro Pro Asn Lys Trp
                    1115                1120                1125
```

Leu Ser Asn Ala Arg Met Thr His Tyr Gln Ala Met Leu Leu Asp
    1130                1135                1140

Ala Glu Arg Val His Phe Gly Pro Thr Val Ser Leu Asn Pro Ala
    1145                1150                1155

Thr Leu Leu Pro Leu Pro Ser Gly Lys Pro Pro Arg Leu Ser Pro
    1160                1165                1170

Asp Leu Ala Glu Thr Met Ala Gln Thr Asp Leu Thr Asp Gln Pro
    1175                1180                1185

Leu Pro Asp Ala Asp Leu Thr Trp Tyr Thr Asp Gly Ser Ser Phe
    1190                1195                1200

Ile Arg Asn Gly Glu Arg Lys Ala Gly Ala Ala Val Thr Thr Glu
    1205                1210                1215

Ser Glu Val Ile Trp Ala Ala Ser Leu Pro Pro Gly Thr Ser Ala
    1220                1225                1230

Gln Arg Ala Glu Leu Ile Ala Leu Thr Gln Ala Leu Lys Met Ala
    1235                1240                1245

Lys Gly Lys Lys Leu Thr Val Tyr Thr Asp Ser Arg Tyr Ala Phe
    1250                1255                1260

Ala Thr Ala His Val His Gly Glu Ile Tyr Arg Arg Arg Gly Leu
    1265                1270                1275

Leu Thr Ser Glu Gly Lys Glu Ile Lys Asn Lys Asn Glu Ile Leu
    1280                1285                1290

Ala Leu Leu Glu Ala Leu Phe Leu Pro Lys Arg Leu Ser Ile Ile
    1295                1300                1305

His Cys Pro Gly His Gln Lys Gly Asp Ser Pro Gln Ala Lys Gly
    1310                1315                1320

Asn Arg Leu Ala Asp Asp Thr Ala Lys Lys Ala Ala Thr Glu Thr
    1325                1330                1335

Gln Ser Ser Leu Thr Ile Leu Ser Ser Ser Ala Ser
    1340                1345                1350

<210> SEQ ID NO 8
<211> LENGTH: 1350
<212> TYPE: PRT
<213> ORGANISM: Artificial Sequence
<220> FEATURE:
<223> OTHER INFORMATION: Synthetic construct

<400> SEQUENCE: 8

Glu Phe Thr Leu Gln Leu Glu Glu Tyr Arg Leu Phe Glu Pro Glu
1               5                   10                  15

Ser Thr Gln Lys Gln Glu Met Asp Ile Trp Leu Lys Asn Phe Pro Gln
            20                  25                  30

Ala Trp Ala Glu Thr Gly Gly Met Gly Met Ala His Cys Gln Ala Pro
        35                  40                  45

Val Leu Ile Gln Leu Lys Ala Thr Ala Thr Pro Ile Ser Ile Arg Gln
    50                  55                  60

Tyr Pro Met Pro His Glu Ala Tyr Gln Gly Ile Lys Pro His Ile Arg
65                  70                  75                  80

Arg Met Leu Asp Gln Gly Ile Leu Lys Pro Cys Gln Ser Pro Trp Asn
                85                  90                  95

Thr Pro Leu Leu Pro Val Lys Lys Pro Gly Thr Lys Asp Tyr Arg Pro
            100                 105                 110

Val Gln Asp Leu Arg Glu Val Asn Lys Arg Val Glu Asp Ile His Pro
        115                 120                 125

```
Thr Val Pro Asn Pro Tyr Asn Leu Leu Ser Thr Leu Pro Pro Ser His
    130                 135                 140

Pro Trp Tyr Thr Val Leu Asp Leu Lys Asp Ala Phe Phe Cys Leu Arg
145                 150                 155                 160

Leu His Ser Glu Ser Gln Leu Leu Phe Ala Phe Glu Trp Arg Asp Pro
                165                 170                 175

Glu Ile Gly Leu Ser Gly Gln Leu Thr Trp Thr Arg Leu Pro Gln Gly
            180                 185                 190

Phe Lys Asn Ser Pro Thr Leu Phe Asp Glu Ala Leu His Ser Asp Leu
        195                 200                 205

Ala Asp Phe Arg Val Arg Tyr Pro Ala Leu Val Leu Leu Gln Tyr Val
210                 215                 220

Asp Asp Leu Leu Leu Ala Ala Ala Thr Arg Thr Glu Cys Leu Glu Gly
225                 230                 235                 240

Thr Lys Ala Leu Leu Glu Thr Leu Gly Asn Lys Gly Tyr Arg Ala Ser
                245                 250                 255

Ala Lys Lys Ala Gln Ile Cys Leu Gln Glu Val Thr Tyr Leu Gly Tyr
            260                 265                 270

Ser Leu Lys Asp Gly Gln Arg Trp Leu Thr Lys Ala Arg Lys Glu Ala
        275                 280                 285

Ile Leu Ser Ile Pro Val Pro Lys Asn Pro Arg Gln Val Arg Glu Phe
290                 295                 300

Leu Gly Thr Ala Gly Tyr Cys Arg Leu Trp Ile Pro Gly Phe Ala Glu
305                 310                 315                 320

Leu Ala Ala Pro Leu Tyr Pro Leu Thr Arg Pro Gly Thr Leu Phe Gln
                325                 330                 335

Trp Gly Thr Glu Gln Gln Leu Ala Phe Glu Asn Ile Arg Lys Ala Leu
            340                 345                 350

Leu Ser Ser Pro Ala Leu Gly Leu Pro Asp Ile Thr Lys Pro Phe Glu
        355                 360                 365

Leu Phe Ile Asp Glu Asn Ser Gly Phe Ala Lys Gly Val Leu Val Gln
370                 375                 380

Lys Leu Gly Pro Trp Lys Arg Pro Val Ala Tyr Leu Ser Lys Lys Leu
385                 390                 395                 400

Asp Thr Val Ala Ser Gly Trp Pro Pro Cys Leu Arg Met Val Ala Ala
                405                 410                 415

Ile Ala Ile Leu Val Lys Asp Ala Gly Lys Leu Thr Leu Gly Gln Pro
            420                 425                 430

Leu Thr Ile Leu Thr Ser His Pro Val Glu Ala Leu Val Arg Gln Pro
        435                 440                 445

Pro Asn Lys Trp Leu Ser Asn Ala Arg Met Thr His Tyr Gln Ala Met
450                 455                 460

Leu Leu Asp Ala Glu Arg Val His Phe Gly Pro Thr Val Ser Leu Asn
465                 470                 475                 480

Pro Ala Thr Leu Leu Pro Leu Pro Ser Gly Lys Pro Pro Arg Leu Ser
                485                 490                 495

Pro Asp Leu Ala Glu Thr Met Ala Gln Thr Asp Leu Thr Asp Gln Pro
            500                 505                 510

Leu Pro Asp Ala Asp Leu Thr Trp Tyr Thr Asn Gly Ser Ser Phe Ile
        515                 520                 525

Arg Asn Gly Glu Arg Lys Ala Gly Ala Ala Val Thr Thr Glu Ser Glu
530                 535                 540
```

```
Val Ile Trp Ala Ala Ser Leu Pro Pro Gly Thr Ser Ala Gln Arg Ala
545                 550                 555                 560

Glu Leu Ile Ala Leu Thr Gln Ala Leu Lys Met Ala Lys Gly Lys Lys
                565                 570                 575

Leu Thr Val Tyr Thr Asp Ser Arg Tyr Ala Phe Ala Thr Ala His Val
            580                 585                 590

His Gly Glu Ile Tyr Arg Arg Gly Leu Leu Thr Ser Glu Gly Lys
        595                 600                 605

Glu Ile Lys Asn Lys Asn Glu Ile Leu Ala Leu Leu Glu Ala Leu Phe
    610                 615                 620

Leu Pro Lys Arg Leu Ser Ile Ile His Cys Pro Gly His Gln Lys Gly
625                 630                 635                 640

Asp Ser Pro Gln Ala Lys Gly Asn Arg Leu Ala Asp Asp Thr Ala Lys
                645                 650                 655

Lys Ala Ala Thr Glu Thr Gln Ser Ser Leu Thr Ile Leu Ser Ser Ser
            660                 665                 670

Ala Ser Lys Leu Glu Phe Thr Leu Gln Leu Glu Glu Tyr Arg Leu
        675                 680                 685

Phe Glu Pro Glu Ser Thr Gln Lys Gln Glu Met Asp Ile Trp Leu Lys
690                 695                 700

Asn Phe Pro Gln Ala Trp Ala Glu Thr Gly Gly Met Gly Met Ala His
705                 710                 715                 720

Cys Gln Ala Pro Val Leu Ile Gln Leu Lys Ala Thr Ala Thr Pro Ile
                725                 730                 735

Ser Ile Arg Gln Tyr Pro Met Pro His Glu Ala Tyr Gln Gly Ile Lys
            740                 745                 750

Pro His Ile Arg Arg Met Leu Asp Gln Gly Ile Leu Lys Pro Cys Gln
        755                 760                 765

Ser Pro Trp Asn Thr Pro Leu Leu Pro Val Lys Lys Pro Gly Thr Lys
    770                 775                 780

Asp Tyr Arg Pro Val Gln Asp Leu Arg Glu Val Asn Lys Arg Val Glu
785                 790                 795                 800

Asp Ile His Pro Thr Val Pro Asn Pro Tyr Asn Leu Leu Ser Thr Leu
                805                 810                 815

Pro Pro Ser His Pro Trp Tyr Thr Val Leu Asp Leu Lys Asp Ala Phe
            820                 825                 830

Phe Cys Leu Arg Leu His Ser Glu Ser Gln Leu Leu Phe Ala Phe Glu
        835                 840                 845

Trp Arg Asp Pro Glu Ile Gly Leu Ser Gly Gln Leu Thr Trp Thr Arg
850                 855                 860

Leu Pro Gln Gly Phe Lys Asn Ser Pro Thr Leu Phe Asp Glu Ala Leu
865                 870                 875                 880

His Ser Asp Leu Ala Asp Phe Arg Val Arg Tyr Pro Ala Leu Val Leu
                885                 890                 895

Leu Gln Tyr Val Asp Asp Leu Leu Leu Ala Ala Ala Thr Arg Thr Glu
            900                 905                 910

Cys Leu Glu Gly Thr Lys Ala Leu Leu Glu Thr Leu Gly Asn Lys Gly
        915                 920                 925

Tyr Arg Ala Ser Ala Lys Lys Ala Gln Ile Cys Leu Gln Glu Val Thr
    930                 935                 940

Tyr Leu Gly Tyr Ser Leu Lys Asp Gly Gln Arg Trp Leu Thr Lys Ala
945                 950                 955                 960

Arg Lys Glu Ala Ile Leu Ser Ile Pro Val Pro Lys Asn Pro Arg Gln
```

```
                965                 970                 975
Val Arg Glu Phe Leu Gly Thr Ala Gly Tyr Cys Arg Leu Trp Ile Pro
                980                 985                 990
Gly Phe Ala Glu Leu Ala Ala Pro Leu Tyr Pro Leu Thr Arg Pro Gly
        995                 1000                1005
Thr Leu Phe Gln Trp Gly Thr Glu Gln Gln Leu Ala Phe Glu Asn
    1010                1015                1020
Ile Arg Lys Ala Leu Leu Ser Ser Pro Ala Leu Gly Leu Pro Asp
    1025                1030                1035
Ile Thr Lys Pro Phe Glu Leu Phe Ile Asp Glu Asn Ser Gly Phe
    1040                1045                1050
Ala Lys Gly Val Leu Val Gln Lys Leu Gly Pro Trp Lys Arg Pro
    1055                1060                1065
Val Ala Tyr Leu Ser Lys Lys Leu Asp Thr Val Ala Ser Gly Trp
    1070                1075                1080
Pro Pro Cys Leu Arg Met Val Ala Ala Ile Ala Ile Leu Val Lys
    1085                1090                1095
Asp Ala Gly Lys Leu Thr Leu Gly Gln Pro Leu Thr Ile Leu Thr
    1100                1105                1110
Ser His Pro Val Glu Ala Leu Val Arg Gln Pro Pro Asn Lys Trp
    1115                1120                1125
Leu Ser Asn Ala Arg Met Thr His Tyr Gln Ala Met Leu Leu Asp
    1130                1135                1140
Ala Glu Arg Val His Phe Gly Pro Thr Val Ser Leu Asn Pro Ala
    1145                1150                1155
Thr Leu Leu Pro Leu Pro Ser Gly Lys Pro Pro Arg Leu Ser Pro
    1160                1165                1170
Asp Leu Ala Glu Thr Met Ala Gln Thr Asp Leu Thr Asp Gln Pro
    1175                1180                1185
Leu Pro Asp Ala Asp Leu Thr Trp Tyr Thr Asn Gly Ser Ser Phe
    1190                1195                1200
Ile Arg Asn Gly Glu Arg Lys Ala Gly Ala Ala Val Thr Thr Glu
    1205                1210                1215
Ser Glu Val Ile Trp Ala Ala Ser Leu Pro Pro Gly Thr Ser Ala
    1220                1225                1230
Gln Arg Ala Glu Leu Ile Ala Leu Thr Gln Ala Leu Lys Met Ala
    1235                1240                1245
Lys Gly Lys Lys Leu Thr Val Tyr Thr Asp Ser Arg Tyr Ala Phe
    1250                1255                1260
Ala Thr Ala His Val His Gly Glu Ile Tyr Arg Arg Arg Gly Leu
    1265                1270                1275
Leu Thr Ser Glu Gly Lys Glu Ile Lys Asn Lys Asn Glu Ile Leu
    1280                1285                1290
Ala Leu Leu Glu Ala Leu Phe Leu Pro Lys Arg Leu Ser Ile Ile
    1295                1300                1305
His Cys Pro Gly His Gln Lys Gly Asp Ser Pro Gln Ala Lys Gly
    1310                1315                1320
Asn Arg Leu Ala Asp Asp Thr Ala Lys Lys Ala Ala Thr Glu Thr
    1325                1330                1335
Gln Ser Ser Leu Thr Ile Leu Ser Ser Ser Ala Ser
    1340                1345                1350

<210> SEQ ID NO 9
```

```
<211> LENGTH: 1354
<212> TYPE: PRT
<213> ORGANISM: Artificial Sequence
<220> FEATURE:
<223> OTHER INFORMATION: Synthetic construct

<400> SEQUENCE: 9

Glu Phe Thr Leu Gln Leu Glu Glu Tyr Arg Leu Phe Glu Pro Glu
1               5                   10                  15

Ser Thr Gln Lys Gln Glu Met Asp Ile Trp Leu Lys Asn Phe Pro Gln
            20                  25                  30

Ala Trp Ala Glu Thr Gly Gly Met Gly Met Ala His Cys Gln Ala Pro
        35                  40                  45

Val Leu Ile Gln Leu Lys Ala Thr Ala Thr Pro Ile Ser Ile Arg Gln
    50                  55                  60

Tyr Pro Met Pro His Glu Ala Tyr Gln Gly Ile Lys Pro His Ile Arg
65                  70                  75                  80

Arg Met Leu Asp Gln Gly Ile Leu Lys Pro Cys Gln Ser Pro Trp Asn
                85                  90                  95

Thr Pro Leu Leu Pro Val Lys Lys Pro Gly Thr Lys Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Thr Leu Pro Pro Ser His
    130                 135                 140

Pro Trp Tyr Thr Val Leu Asp Leu Lys Asp Ala Phe Phe Cys Leu Arg
145                 150                 155                 160

Leu His Ser Glu Ser Gln Leu Leu Phe Ala Phe Glu Trp Arg Asp Pro
                165                 170                 175

Glu Ile Gly Leu Ser Gly Gln Leu Thr Trp Thr Arg Leu Pro Gln Gly
            180                 185                 190

Phe Lys Asn Ser Pro Thr Leu Phe Asp Glu Ala Leu His Ser Asp Leu
        195                 200                 205

Ala Asp Phe Arg Val Arg Tyr Pro Ala Leu Val Leu Leu Gln Tyr Val
    210                 215                 220

Asp Asp Leu Leu Leu Ala Ala Ala Thr Arg Thr Glu Cys Leu Glu Gly
225                 230                 235                 240

Thr Lys Ala Leu Leu Glu Thr Leu Gly Asn Lys Gly Tyr Arg Ala Ser
                245                 250                 255

Ala Lys Lys Ala Gln Ile Cys Leu Gln Glu Val Thr Tyr Leu Gly Tyr
            260                 265                 270

Ser Leu Lys Asp Gly Gln Arg Trp Leu Thr Lys Ala Arg Lys Glu Ala
        275                 280                 285

Ile Leu Ser Ile Pro Val Pro Lys Asn Pro Arg Gln Val Arg Glu Phe
    290                 295                 300

Leu Gly Thr Ala Gly Tyr Cys Arg Leu Trp Ile Pro Gly Phe Ala Glu
305                 310                 315                 320

Leu Ala Ala Pro Leu Tyr Pro Leu Thr Arg Pro Gly Thr Leu Phe Gln
                325                 330                 335

Trp Gly Thr Glu Gln Gln Leu Ala Phe Glu Asn Ile Arg Lys Ala Leu
            340                 345                 350

Leu Ser Ser Pro Ala Leu Gly Leu Pro Asp Ile Thr Lys Pro Phe Glu
        355                 360                 365

Leu Phe Ile Asp Glu Asn Ser Gly Phe Ala Lys Gly Val Leu Val Gln
    370                 375                 380
```

```
Lys Leu Gly Pro Trp Lys Arg Pro Val Ala Tyr Leu Ser Lys Lys Leu
385                 390                 395                 400

Asp Thr Val Ala Ser Gly Trp Pro Pro Cys Leu Arg Met Val Ala Ala
            405                 410                 415

Ile Ala Ile Leu Val Lys Asp Ala Gly Lys Leu Thr Leu Gly Gln Pro
        420                 425                 430

Leu Thr Ile Leu Thr Ser His Pro Val Glu Ala Leu Val Arg Gln Pro
        435                 440                 445

Pro Asn Lys Trp Leu Ser Asn Ala Arg Met Thr His Tyr Gln Ala Met
    450                 455                 460

Leu Leu Asp Ala Glu Arg Val His Phe Gly Pro Thr Val Ser Leu Asn
465                 470                 475                 480

Pro Ala Thr Leu Leu Pro Leu Pro Ser Gly Lys Pro Pro Arg Leu Ser
            485                 490                 495

Pro Asp Leu Ala Glu Thr Met Ala Gln Thr Asp Leu Thr Asp Gln Pro
            500                 505                 510

Leu Pro Asp Ala Asp Leu Thr Trp Tyr Thr Asp Gly Ser Ser Phe Ile
        515                 520                 525

Arg Asn Gly Glu Arg Lys Ala Gly Ala Ala Val Thr Thr Glu Ser Glu
        530                 535                 540

Val Ile Trp Ala Ala Ser Leu Pro Pro Gly Thr Ser Ala Gln Arg Ala
545                 550                 555                 560

Glu Leu Ile Ala Leu Thr Gln Ala Leu Lys Met Ala Lys Gly Lys Lys
            565                 570                 575

Leu Thr Val Tyr Thr Asp Ser Arg Tyr Ala Phe Ala Thr Ala His Val
            580                 585                 590

His Gly Glu Ile Tyr Arg Arg Arg Gly Leu Leu Thr Ser Glu Gly Lys
        595                 600                 605

Glu Ile Lys Asn Lys Asn Glu Ile Leu Ala Leu Leu Glu Ala Leu Phe
        610                 615                 620

Leu Pro Lys Arg Leu Ser Ile Ile His Cys Pro Gly His Gln Lys Gly
625                 630                 635                 640

Asp Ser Pro Gln Ala Lys Gly Asn Arg Leu Ala Asp Asp Thr Ala Lys
            645                 650                 655

Lys Ala Ala Thr Glu Thr Gln Ser Ser Leu Thr Ile Leu Ser Ser Ser
            660                 665                 670

Ala Ser Lys Leu Glu Phe Thr Leu Asn Ile Glu Asp Glu His Arg Leu
        675                 680                 685

His Glu Thr Ser Lys Glu Pro Asp Val Ser Leu Gly Ser Thr Trp Leu
        690                 695                 700

Ser Asp Phe Pro Gln Ala Trp Ala Glu Thr Gly Gly Met Gly Leu Ala
705                 710                 715                 720

Val Arg Gln Ala Pro Leu Ile Ile Pro Leu Lys Ala Thr Ser Thr Pro
            725                 730                 735

Val Ser Ile Lys Gln Tyr Pro Met Ser Gln Glu Ala Arg Leu Gly Ile
            740                 745                 750

Lys Pro His Ile Gln Arg Leu Leu Asp Gln Gly Ile Leu Val Pro Cys
        755                 760                 765

Gln Ser Pro Trp Asn Thr Pro Leu Leu Pro Val Lys Lys Pro Gly Thr
        770                 775                 780

Asn Asp Tyr Arg Pro Val Gln Asp Leu Arg Glu Val Asn Lys Arg Val
785                 790                 795                 800
```

```
Glu Asp Ile His Pro Thr Val Pro Asn Pro Tyr Asn Leu Leu Ser Gly
                805                 810                 815
Leu Pro Pro Ser His Gln Trp Tyr Thr Val Leu Asp Leu Lys Asp Ala
            820                 825                 830
Phe Phe Cys Leu Arg Leu His Pro Thr Ser Gln Pro Leu Phe Ala Phe
            835                 840                 845
Glu Trp Arg Asp Pro Glu Met Gly Ile Ser Gly Gln Leu Thr Trp Thr
850                 855                 860
Arg Leu Pro Gln Gly Phe Lys Asn Ser Pro Thr Leu Phe Asp Glu Ala
865                 870                 875                 880
Leu His Arg Asp Leu Ala Asp Phe Arg Ile Gln His Pro Asp Leu Ile
                885                 890                 895
Leu Leu Gln Tyr Val Asp Asp Leu Leu Leu Ala Ala Thr Ser Glu Leu
                900                 905                 910
Asp Cys Gln Gln Gly Thr Arg Ala Leu Leu Gln Thr Leu Gly Asn Leu
            915                 920                 925
Gly Tyr Arg Ala Ser Ala Lys Lys Ala Gln Ile Cys Gln Lys Gln Val
            930                 935                 940
Lys Tyr Leu Gly Tyr Leu Leu Lys Glu Gly Gln Arg Trp Leu Thr Glu
945                 950                 955                 960
Ala Arg Lys Glu Thr Val Met Gly Gln Pro Thr Pro Lys Thr Pro Arg
                965                 970                 975
Gln Leu Arg Glu Phe Leu Gly Thr Ala Gly Phe Cys Arg Leu Trp Ile
            980                 985                 990
Pro Gly Phe Ala Glu Met Ala Ala Pro Leu Tyr Pro Leu Thr Lys Thr
            995                 1000                1005
Gly Thr Leu Phe Asn Trp Gly Pro Asp Gln Gln Lys Ala Tyr Gln
    1010                1015                1020
Glu Ile Lys Gln Ala Leu Leu Thr Ala Pro Ala Leu Gly Leu Pro
    1025                1030                1035
Asp Leu Thr Lys Pro Phe Glu Leu Phe Val Asp Glu Lys Gln Gly
    1040                1045                1050
Tyr Ala Lys Gly Val Leu Thr Gln Lys Leu Gly Pro Trp Arg Arg
    1055                1060                1065
Pro Val Ala Tyr Leu Ser Lys Lys Leu Asp Pro Val Ala Ala Gly
    1070                1075                1080
Trp Pro Pro Cys Leu Arg Met Val Ala Ala Ile Ala Val Leu Thr
    1085                1090                1095
Lys Asp Ala Gly Lys Leu Thr Met Gly Gln Pro Leu Val Ile Leu
    1100                1105                1110
Ala Pro His Ala Val Glu Ala Leu Val Lys Gln Pro Pro Asp Arg
    1115                1120                1125
Trp Leu Ser Asn Ala Arg Met Thr His Tyr Gln Ala Leu Leu Leu
    1130                1135                1140
Asp Thr Asp Arg Val Gln Phe Gly Pro Val Val Ala Leu Asn Pro
    1145                1150                1155
Ala Thr Leu Leu Pro Leu Pro Glu Glu Gly Leu Gln His Asn Cys
    1160                1165                1170
Leu Asp Ile Leu Ala Glu Ala His Gly Thr Arg Pro Asp Leu Thr
    1175                1180                1185
Asp Gln Pro Leu Pro Asp Ala Asp His Thr Trp Tyr Thr Asp Gly
    1190                1195                1200
Ser Ser Leu Leu Gln Glu Gly Gln Arg Lys Ala Gly Ala Ala Val
```

```
                   1205                1210                1215

Thr  Thr  Glu  Thr  Glu  Val  Ile  Trp  Ala  Lys  Ala  Leu  Pro  Ala  Gly
     1220                1225                1230

Thr  Ser  Ala  Gln  Arg  Ala  Glu  Leu  Ile  Ala  Leu  Thr  Gln  Ala  Leu
     1235                1240                1245

Lys  Met  Ala  Glu  Gly  Lys  Lys  Leu  Asn  Val  Tyr  Thr  Asp  Ser  Arg
     1250                1255                1260

Tyr  Ala  Phe  Ala  Thr  Ala  His  Ile  His  Gly  Glu  Ile  Tyr  Arg  Arg
     1265                1270                1275

Arg  Gly  Leu  Leu  Thr  Ser  Glu  Gly  Lys  Glu  Ile  Lys  Asn  Lys  Asp
     1280                1285                1290

Glu  Ile  Leu  Ala  Leu  Leu  Lys  Ala  Leu  Phe  Leu  Pro  Lys  Arg  Leu
     1295                1300                1305

Ser  Ile  Ile  His  Cys  Pro  Gly  His  Gln  Lys  Gly  His  Ser  Ala  Glu
     1310                1315                1320

Ala  Arg  Gly  Asn  Arg  Met  Ala  Asp  Gln  Ala  Ala  Arg  Lys  Ala  Ala
     1325                1330                1335

Ile  Thr  Glu  Thr  Pro  Asp  Thr  Ser  Thr  Leu  Leu  Ser  Ser  Ser  Ala
     1340                1345                1350

Ser
```

<210> SEQ ID NO 10
<211> LENGTH: 1354
<212> TYPE: PRT
<213> ORGANISM: Artificial Sequence
<220> FEATURE:
<223> OTHER INFORMATION: Synthetic construct

<400> SEQUENCE: 10

```
Glu  Phe  Thr  Leu  Gln  Leu  Glu  Glu  Glu  Tyr  Arg  Leu  Phe  Glu  Pro  Glu
1                 5                  10                 15

Ser  Thr  Gln  Lys  Gln  Glu  Met  Asp  Ile  Trp  Leu  Lys  Asn  Phe  Pro  Gln
             20                  25                 30

Ala  Trp  Ala  Glu  Thr  Gly  Gly  Met  Gly  Met  Ala  His  Cys  Gln  Ala  Pro
         35                 40                 45

Val  Leu  Ile  Gln  Leu  Lys  Ala  Thr  Ala  Thr  Pro  Ile  Ser  Ile  Arg  Gln
     50                  55                 60

Tyr  Pro  Met  Pro  His  Glu  Ala  Tyr  Gln  Gly  Ile  Lys  Pro  His  Ile  Arg
65                  70                  75                 80

Arg  Met  Leu  Asp  Gln  Gly  Ile  Leu  Lys  Pro  Cys  Gln  Ser  Pro  Trp  Asn
             85                  90                 95

Thr  Pro  Leu  Leu  Pro  Val  Lys  Lys  Pro  Gly  Thr  Lys  Asp  Tyr  Arg  Pro
         100                105                110

Val  Gln  Asp  Leu  Arg  Glu  Val  Asn  Lys  Arg  Val  Glu  Asp  Ile  His  Pro
     115                 120                125

Thr  Val  Pro  Asn  Pro  Tyr  Asn  Leu  Leu  Ser  Thr  Leu  Pro  Pro  Ser  His
     130                 135                140

Pro  Trp  Tyr  Thr  Val  Leu  Asp  Leu  Lys  Asp  Ala  Phe  Phe  Cys  Leu  Arg
145                 150                 155                160

Leu  His  Ser  Glu  Ser  Gln  Leu  Phe  Ala  Phe  Glu  Trp  Arg  Asp  Pro
             165                 170                175

Glu  Ile  Gly  Leu  Ser  Gly  Gln  Leu  Thr  Trp  Thr  Arg  Leu  Pro  Gln  Gly
         180                 185                190

Phe  Lys  Asn  Ser  Pro  Thr  Leu  Phe  Asp  Glu  Ala  Leu  His  Ser  Asp  Leu
     195                 200                205
```

-continued

```
Ala Asp Phe Arg Val Arg Tyr Pro Ala Leu Val Leu Leu Gln Tyr Val
210                 215                 220
Asp Asp Leu Leu Leu Ala Ala Thr Arg Thr Glu Cys Leu Glu Gly
225                 230                 235                 240
Thr Lys Ala Leu Leu Glu Thr Leu Gly Asn Lys Gly Tyr Arg Ala Ser
            245                 250                 255
Ala Lys Lys Ala Gln Ile Cys Leu Gln Glu Val Thr Tyr Leu Gly Tyr
                260                 265                 270
Ser Leu Lys Asp Gly Gln Arg Trp Leu Thr Lys Ala Arg Lys Glu Ala
        275                 280                 285
Ile Leu Ser Ile Pro Val Pro Lys Asn Pro Arg Gln Val Arg Glu Phe
290                 295                 300
Leu Gly Thr Ala Gly Tyr Cys Arg Leu Trp Ile Pro Gly Phe Ala Glu
305                 310                 315                 320
Leu Ala Ala Pro Leu Tyr Pro Leu Thr Arg Pro Gly Thr Leu Phe Gln
                325                 330                 335
Trp Gly Thr Glu Gln Gln Leu Ala Phe Glu Asn Ile Arg Lys Ala Leu
            340                 345                 350
Leu Ser Ser Pro Ala Leu Gly Leu Pro Asp Ile Thr Lys Pro Phe Glu
        355                 360                 365
Leu Phe Ile Asp Glu Asn Ser Gly Phe Ala Lys Gly Val Leu Val Gln
370                 375                 380
Lys Leu Gly Pro Trp Lys Arg Pro Val Ala Tyr Leu Ser Lys Lys Leu
385                 390                 395                 400
Asp Thr Val Ala Ser Gly Trp Pro Pro Cys Leu Arg Met Val Ala Ala
                405                 410                 415
Ile Ala Ile Leu Val Lys Asp Ala Gly Lys Leu Thr Leu Gly Gln Pro
            420                 425                 430
Leu Thr Ile Leu Thr Ser His Pro Val Glu Ala Leu Val Arg Gln Pro
        435                 440                 445
Pro Asn Lys Trp Leu Ser Asn Ala Arg Met Thr His Tyr Gln Ala Met
450                 455                 460
Leu Leu Asp Ala Glu Arg Val His Phe Gly Pro Thr Val Ser Leu Asn
465                 470                 475                 480
Pro Ala Thr Leu Leu Pro Leu Pro Ser Gly Lys Pro Pro Arg Leu Ser
                485                 490                 495
Pro Asp Leu Ala Glu Thr Met Ala Gln Thr Asp Leu Thr Asp Gln Pro
            500                 505                 510
Leu Pro Asp Ala Asp Leu Thr Trp Tyr Thr Asn Gly Ser Ser Phe Ile
        515                 520                 525
Arg Asn Gly Glu Arg Lys Ala Gly Ala Ala Val Thr Thr Glu Ser Glu
530                 535                 540
Val Ile Trp Ala Ala Ser Leu Pro Pro Gly Thr Ser Ala Gln Arg Ala
545                 550                 555                 560
Glu Leu Ile Ala Leu Thr Gln Ala Leu Lys Met Ala Lys Gly Lys Lys
                565                 570                 575
Leu Thr Val Tyr Thr Asp Ser Arg Tyr Ala Phe Ala Thr Ala His Val
            580                 585                 590
His Gly Glu Ile Tyr Arg Arg Arg Gly Leu Leu Thr Ser Glu Gly Lys
        595                 600                 605
Glu Ile Lys Asn Lys Asn Glu Ile Leu Ala Leu Leu Glu Ala Leu Phe
610                 615                 620
```

```
Leu Pro Lys Arg Leu Ser Ile Ile His Cys Pro Gly His Gln Lys Gly
625                 630                 635                 640

Asp Ser Pro Gln Ala Lys Gly Asn Arg Leu Ala Asp Asp Thr Ala Lys
            645                 650                 655

Lys Ala Ala Thr Glu Thr Gln Ser Ser Leu Thr Ile Leu Ser Ser Ser
            660                 665                 670

Ala Ser Lys Leu Glu Phe Thr Leu Asn Ile Glu Asp Glu His Arg Leu
        675                 680                 685

His Glu Thr Ser Lys Glu Pro Asp Val Ser Leu Gly Ser Thr Trp Leu
    690                 695                 700

Ser Asp Phe Pro Gln Ala Trp Ala Glu Thr Gly Gly Met Gly Leu Ala
705                 710                 715                 720

Val Arg Gln Ala Pro Leu Ile Ile Pro Leu Lys Ala Thr Ser Thr Pro
            725                 730                 735

Val Ser Ile Lys Gln Tyr Pro Met Ser Gln Glu Ala Arg Leu Gly Ile
            740                 745                 750

Lys Pro His Ile Gln Arg Leu Leu Asp Gln Gly Ile Leu Val Pro Cys
        755                 760                 765

Gln Ser Pro Trp Asn Thr Pro Leu Leu Pro Val Lys Lys Pro Gly Thr
770                 775                 780

Asn Asp Tyr Arg Pro Val Gln Asp Leu Arg Glu Val Asn Lys Arg Val
785                 790                 795                 800

Glu Asp Ile His Pro Thr Val Pro Asn Pro Tyr Asn Leu Leu Ser Gly
            805                 810                 815

Leu Pro Pro Ser His Gln Trp Tyr Thr Val Leu Asp Leu Lys Asp Ala
        820                 825                 830

Phe Phe Cys Leu Arg Leu His Pro Thr Ser Gln Pro Leu Phe Ala Phe
        835                 840                 845

Glu Trp Arg Asp Pro Glu Met Gly Ile Ser Gly Gln Leu Thr Trp Thr
850                 855                 860

Arg Leu Pro Gln Gly Phe Lys Asn Ser Pro Thr Leu Phe Asp Glu Ala
865                 870                 875                 880

Leu His Arg Asp Leu Ala Asp Phe Arg Ile Gln His Pro Asp Leu Ile
            885                 890                 895

Leu Leu Gln Tyr Val Asp Asp Leu Leu Leu Ala Ala Thr Ser Glu Leu
            900                 905                 910

Asp Cys Gln Gln Gly Thr Arg Ala Leu Leu Gln Thr Leu Gly Asn Leu
        915                 920                 925

Gly Tyr Arg Ala Ser Ala Lys Lys Ala Gln Ile Cys Gln Lys Gln Val
    930                 935                 940

Lys Tyr Leu Gly Tyr Leu Leu Lys Glu Gly Gln Arg Trp Leu Thr Glu
945                 950                 955                 960

Ala Arg Lys Glu Thr Val Met Gly Gln Pro Thr Pro Lys Thr Pro Arg
            965                 970                 975

Gln Leu Arg Glu Phe Leu Gly Thr Ala Gly Phe Cys Arg Leu Trp Ile
        980                 985                 990

Pro Gly Phe Ala Glu Met Ala Ala Pro Leu Tyr Pro Leu Thr Lys Thr
    995                 1000                1005

Gly Thr Leu Phe Asn Trp Gly Pro Asp Gln Gln Lys Ala Tyr Gln
        1010                1015                1020

Glu Ile Lys Gln Ala Leu Leu Thr Ala Pro Ala Leu Gly Leu Pro
    1025                1030                1035

Asp Leu Thr Lys Pro Phe Glu Leu Phe Val Asp Glu Lys Gln Gly
```

```
                1040                1045                1050

Tyr Ala Lys Gly Val Leu Thr Gln Lys Leu Gly Pro Trp Arg Arg
        1055                1060                1065

Pro Val Ala Tyr Leu Ser Lys Lys Leu Asp Pro Val Ala Ala Gly
    1070                1075                1080

Trp Pro Pro Cys Leu Arg Met Val Ala Ile Ala Val Leu Thr
    1085                1090                1095

Lys Asp Ala Gly Lys Leu Thr Met Gly Gln Pro Leu Val Ile Leu
    1100                1105                1110

Ala Pro His Ala Val Glu Ala Leu Val Lys Gln Pro Pro Asp Arg
    1115                1120                1125

Trp Leu Ser Asn Ala Arg Met Thr His Tyr Gln Ala Leu Leu Leu
    1130                1135                1140

Asp Thr Asp Arg Val Gln Phe Gly Pro Val Val Ala Leu Asn Pro
    1145                1150                1155

Ala Thr Leu Leu Pro Leu Pro Glu Glu Gly Leu Gln His Asn Cys
    1160                1165                1170

Leu Asp Ile Leu Ala Glu Ala His Gly Thr Arg Pro Asp Leu Thr
    1175                1180                1185

Asp Gln Pro Leu Pro Asp Ala Asp His Thr Trp Tyr Thr Asp Gly
    1190                1195                1200

Ser Ser Leu Leu Gln Glu Gly Gln Arg Lys Ala Gly Ala Ala Val
    1205                1210                1215

Thr Thr Glu Thr Glu Val Ile Trp Ala Lys Ala Leu Pro Ala Gly
    1220                1225                1230

Thr Ser Ala Gln Arg Ala Glu Leu Ile Ala Leu Thr Gln Ala Leu
    1235                1240                1245

Lys Met Ala Glu Gly Lys Lys Leu Asn Val Tyr Thr Asp Ser Arg
    1250                1255                1260

Tyr Ala Phe Ala Thr Ala His Ile His Gly Glu Ile Tyr Arg Arg
    1265                1270                1275

Arg Gly Leu Leu Thr Ser Glu Gly Lys Glu Ile Lys Asn Lys Asp
    1280                1285                1290

Glu Ile Leu Ala Leu Leu Lys Ala Leu Phe Leu Pro Lys Arg Leu
    1295                1300                1305

Ser Ile Ile His Cys Pro Gly His Gln Lys Gly His Ser Ala Glu
    1310                1315                1320

Ala Arg Gly Asn Arg Met Ala Asp Gln Ala Ala Arg Lys Ala Ala
    1325                1330                1335

Ile Thr Glu Thr Pro Asp Thr Ser Thr Leu Leu Ser Ser Ser Ala
    1340                1345                1350

Ser

<210> SEQ ID NO 11
<211> LENGTH: 1354
<212> TYPE: PRT
<213> ORGANISM: Artificial Sequence
<220> FEATURE:
<223> OTHER INFORMATION: Synthetic construct

<400> SEQUENCE: 11

Glu Phe Thr Leu Gln Leu Glu Glu Glu Tyr Arg Leu Phe Glu Pro Glu
1               5                   10                  15

Ser Thr Gln Lys Gln Glu Met Asp Ile Trp Leu Lys Asn Phe Pro Gln
            20                  25                  30
```

-continued

Ala Trp Ala Glu Thr Gly Gly Met Gly Met Ala His Cys Gln Ala Pro
         35                  40                  45

Val Leu Ile Gln Leu Lys Ala Thr Ala Thr Pro Ile Ser Ile Arg Gln
         50                  55                  60

Tyr Pro Met Pro His Glu Ala Tyr Gln Gly Ile Lys Pro His Ile Arg
65                  70                  75                  80

Arg Met Leu Asp Gln Gly Ile Leu Lys Pro Cys Gln Ser Pro Trp Asn
             85                  90                  95

Thr Pro Leu Leu Pro Val Lys Lys Pro Gly Thr Lys Asp Tyr Arg Pro
                 100                 105                 110

Val Gln Asp Leu Arg Glu Val Asn Lys Arg Val Glu Asp Ile His Pro
             115                 120                 125

Thr Val Pro Asn Pro Tyr Asn Leu Leu Ser Thr Leu Pro Pro Ser His
         130                 135                 140

Pro Trp Tyr Thr Val Leu Asp Leu Lys Asp Ala Phe Phe Cys Leu Arg
145                 150                 155                 160

Leu His Ser Glu Ser Gln Leu Leu Phe Ala Phe Glu Trp Arg Asp Pro
                 165                 170                 175

Glu Ile Gly Leu Ser Gly Gln Leu Thr Trp Thr Arg Leu Pro Gln Gly
             180                 185                 190

Phe Lys Asn Ser Pro Thr Leu Phe Asp Glu Ala Leu His Ser Asp Leu
         195                 200                 205

Ala Asp Phe Arg Val Arg Tyr Pro Ala Leu Val Leu Leu Gln Tyr Val
         210                 215                 220

Asp Asp Leu Leu Leu Ala Ala Thr Arg Thr Glu Cys Leu Glu Gly
225                 230                 235                 240

Thr Lys Ala Leu Leu Glu Thr Leu Gly Asn Lys Gly Tyr Arg Ala Ser
                 245                 250                 255

Ala Lys Lys Ala Gln Ile Cys Leu Gln Glu Val Thr Tyr Leu Gly Tyr
             260                 265                 270

Ser Leu Lys Asp Gly Gln Arg Trp Leu Thr Lys Ala Arg Lys Glu Ala
         275                 280                 285

Ile Leu Ser Ile Pro Val Pro Lys Asn Pro Arg Gln Val Arg Glu Phe
         290                 295                 300

Leu Gly Thr Ala Gly Tyr Cys Arg Leu Trp Ile Pro Gly Phe Ala Glu
305                 310                 315                 320

Leu Ala Ala Pro Leu Tyr Pro Leu Thr Arg Pro Gly Thr Leu Phe Gln
                 325                 330                 335

Trp Gly Thr Glu Gln Gln Leu Ala Phe Glu Asn Ile Arg Lys Ala Leu
             340                 345                 350

Leu Ser Ser Pro Ala Leu Gly Leu Pro Asp Ile Thr Lys Pro Phe Glu
         355                 360                 365

Leu Phe Ile Asp Glu Asn Ser Gly Phe Ala Lys Gly Val Leu Val Gln
         370                 375                 380

Lys Leu Gly Pro Trp Lys Arg Pro Val Ala Tyr Leu Ser Lys Lys Leu
385                 390                 395                 400

Asp Thr Val Ala Ser Gly Trp Pro Pro Cys Leu Arg Met Val Ala Ala
                 405                 410                 415

Ile Ala Ile Leu Val Lys Asp Ala Gly Lys Leu Thr Leu Gly Gln Pro
             420                 425                 430

Leu Thr Ile Leu Thr Ser His Pro Val Glu Ala Leu Val Arg Gln Pro
         435                 440                 445

-continued

```
Pro Asn Lys Trp Leu Ser Asn Ala Arg Met Thr His Tyr Gln Ala Met
450                 455                 460

Leu Leu Asp Ala Glu Arg Val His Phe Gly Pro Thr Val Ser Leu Asn
465                 470                 475                 480

Pro Ala Thr Leu Leu Pro Leu Pro Ser Gly Lys Pro Pro Arg Leu Ser
                485                 490                 495

Pro Asp Leu Ala Glu Thr Met Ala Gln Thr Asp Leu Thr Asp Gln Pro
                500                 505                 510

Leu Pro Asp Ala Asp Leu Thr Trp Tyr Thr Asn Gly Ser Ser Phe Ile
                515                 520                 525

Arg Asn Gly Glu Arg Lys Ala Gly Ala Ala Val Thr Thr Glu Ser Glu
530                 535                 540

Val Ile Trp Ala Ala Ser Leu Pro Pro Gly Thr Ser Ala Gln Arg Ala
545                 550                 555                 560

Glu Leu Ile Ala Leu Thr Gln Ala Leu Lys Met Ala Lys Gly Lys Lys
                565                 570                 575

Leu Thr Val Tyr Thr Asp Ser Arg Tyr Ala Phe Ala Thr Ala His Val
                580                 585                 590

His Gly Glu Ile Tyr Arg Arg Arg Gly Leu Leu Thr Ser Glu Gly Lys
                595                 600                 605

Glu Ile Lys Asn Lys Asn Glu Ile Leu Ala Leu Leu Glu Ala Leu Phe
610                 615                 620

Leu Pro Lys Arg Leu Ser Ile Ile His Cys Pro Gly His Gln Lys Gly
625                 630                 635                 640

Asp Ser Pro Gln Ala Lys Gly Asn Arg Leu Ala Asp Asp Thr Ala Lys
                645                 650                 655

Lys Ala Ala Thr Glu Thr Gln Ser Ser Leu Thr Ile Leu Ser Ser Ser
                660                 665                 670

Ala Ser Lys Leu Glu Phe Thr Leu Asn Ile Glu Asp Glu His Arg Leu
                675                 680                 685

His Glu Thr Ser Lys Glu Pro Asp Val Ser Leu Gly Ser Thr Trp Leu
                690                 695                 700

Ser Asp Phe Pro Gln Ala Trp Ala Glu Thr Gly Gly Met Gly Leu Ala
705                 710                 715                 720

Val Arg Gln Ala Pro Leu Ile Ile Pro Leu Lys Ala Thr Ser Thr Pro
                725                 730                 735

Val Ser Ile Lys Gln Tyr Pro Met Ser Gln Glu Ala Arg Leu Gly Ile
                740                 745                 750

Lys Pro His Ile Gln Arg Leu Leu Asp Gln Gly Ile Leu Val Pro Cys
                755                 760                 765

Gln Ser Pro Trp Asn Thr Pro Leu Leu Pro Val Lys Lys Pro Gly Thr
770                 775                 780

Asn Asp Tyr Arg Pro Val Gln Asp Leu Arg Glu Val Asn Lys Arg Val
785                 790                 795                 800

Glu Asp Ile His Pro Thr Val Pro Asn Pro Tyr Asn Leu Leu Ser Gly
                805                 810                 815

Leu Pro Pro Ser His Gln Trp Tyr Thr Val Leu Asp Leu Lys Asp Ala
                820                 825                 830

Phe Phe Cys Leu Arg Leu His Pro Thr Ser Gln Pro Leu Phe Ala Phe
                835                 840                 845

Glu Trp Arg Asp Pro Glu Met Gly Ile Ser Gly Gln Leu Thr Trp Thr
850                 855                 860

Arg Leu Pro Gln Gly Phe Lys Asn Ser Pro Thr Leu Phe Asp Glu Ala
```

```
865                 870                 875                 880
Leu His Arg Asp Leu Ala Asp Phe Arg Ile Gln His Pro Asp Leu Ile
                885                 890                 895
Leu Leu Gln Tyr Val Asp Asp Leu Leu Leu Ala Ala Thr Ser Glu Leu
                900                 905                 910
Asp Cys Gln Gln Gly Thr Arg Ala Leu Leu Gln Thr Leu Gly Asn Leu
                915                 920                 925
Gly Tyr Arg Ala Ser Ala Lys Lys Ala Gln Ile Cys Gln Lys Gln Val
            930                 935                 940
Lys Tyr Leu Gly Tyr Leu Leu Lys Glu Gly Gln Arg Trp Leu Thr Glu
945                 950                 955                 960
Ala Arg Lys Glu Thr Val Met Gly Gln Pro Thr Pro Lys Thr Pro Arg
                965                 970                 975
Gln Leu Arg Glu Phe Leu Gly Thr Ala Gly Phe Cys Arg Leu Trp Ile
                980                 985                 990
Pro Gly Phe Ala Glu Met Ala Ala Pro Leu Tyr Pro Leu Thr Lys Thr
                995                 1000                1005
Gly Thr Leu Phe Asn Trp Gly Pro Asp Gln Gln Lys Ala Tyr Gln
        1010                1015                1020
Glu Ile Lys Gln Ala Leu Leu Thr Ala Pro Ala Leu Gly Leu Pro
        1025                1030                1035
Asp Leu Thr Lys Pro Phe Glu Leu Phe Val Asp Glu Lys Gln Gly
        1040                1045                1050
Tyr Ala Lys Gly Val Leu Thr Gln Lys Leu Gly Pro Trp Arg Arg
        1055                1060                1065
Pro Val Ala Tyr Leu Ser Lys Lys Leu Asp Pro Val Ala Ala Gly
        1070                1075                1080
Trp Pro Pro Cys Leu Arg Met Val Ala Ala Ile Ala Val Leu Thr
        1085                1090                1095
Lys Asp Ala Gly Lys Leu Thr Met Gly Gln Pro Leu Val Ile Leu
        1100                1105                1110
Ala Pro His Ala Val Glu Ala Leu Val Lys Gln Pro Pro Asp Arg
        1115                1120                1125
Trp Leu Ser Asn Ala Arg Met Thr His Tyr Gln Ala Leu Leu Leu
        1130                1135                1140
Asp Thr Asp Arg Val Gln Phe Gly Pro Val Val Ala Leu Asn Pro
        1145                1150                1155
Ala Thr Leu Leu Pro Leu Pro Glu Glu Gly Leu Gln His Asn Cys
        1160                1165                1170
Leu Asp Ile Leu Ala Glu Ala His Gly Thr Arg Pro Asp Leu Thr
        1175                1180                1185
Asp Gln Pro Leu Pro Asp Ala Asp His Thr Trp Tyr Thr Asn Gly
        1190                1195                1200
Ser Ser Leu Leu Gln Glu Gly Gln Arg Lys Ala Gly Ala Ala Val
        1205                1210                1215
Thr Thr Glu Thr Glu Val Ile Trp Ala Lys Ala Leu Pro Ala Gly
        1220                1225                1230
Thr Ser Ala Gln Arg Ala Glu Leu Ile Ala Leu Thr Gln Ala Leu
        1235                1240                1245
Lys Met Ala Glu Gly Lys Lys Leu Asn Val Tyr Thr Asp Ser Arg
        1250                1255                1260
Tyr Ala Phe Ala Thr Ala His Ile His Gly Glu Ile Tyr Arg Arg
        1265                1270                1275
```

Arg Gly Leu Leu Thr Ser Glu Gly Lys Glu Ile Lys Asn Lys Asp
        1280                1285                1290

Glu Ile Leu Ala Leu Leu Lys Ala Leu Phe Leu Pro Lys Arg Leu
    1295                1300                1305

Ser Ile Ile His Cys Pro Gly His Gln Lys Gly His Ser Ala Glu
    1310                1315                1320

Ala Arg Gly Asn Arg Met Ala Asp Gln Ala Ala Arg Lys Ala Ala
    1325                1330                1335

Ile Thr Glu Thr Pro Asp Thr Ser Thr Leu Leu Ser Ser Ser Ala
    1340                1345                1350

Ser

<210> SEQ ID NO 12
<211> LENGTH: 1354
<212> TYPE: PRT
<213> ORGANISM: Artificial Sequence
<220> FEATURE:
<223> OTHER INFORMATION: Synthetic construct

<400> SEQUENCE: 12

Glu Phe Thr Leu Asn Ile Glu Asp Glu His Arg Leu His Glu Thr Ser
1               5                   10                  15

Lys Glu Pro Asp Val Ser Leu Gly Ser Thr Trp Leu Ser Asp Phe Pro
            20                  25                  30

Gln Ala Trp Ala Glu Thr Gly Gly Met Gly Leu Ala Val Arg Gln Ala
        35                  40                  45

Pro Leu Ile Ile Pro Leu Lys Ala Thr Ser Thr Pro Val Ser Ile Lys
    50                  55                  60

Gln Tyr Pro Met Ser Gln Glu Ala Arg Leu Gly Ile Lys Pro His Ile
65                  70                  75                  80

Gln Arg Leu Leu Asp Gln Gly Ile Leu Val Pro Cys Gln Ser Pro Trp
                85                  90                  95

Asn Thr Pro Leu Leu Pro Val Lys Lys Pro Gly Thr Asn Asp Tyr Arg
            100                 105                 110

Pro Val Gln Asp Leu Arg Glu Val Asn Lys Arg Val Glu Asp Ile His
        115                 120                 125

Pro Thr Val Pro Asn Pro Tyr Asn Leu Leu Ser Gly Leu Pro Pro Ser
    130                 135                 140

His Gln Trp Tyr Thr Val Leu Asp Leu Lys Asp Ala Phe Phe Cys Leu
145                 150                 155                 160

Arg Leu His Pro Thr Ser Gln Pro Leu Phe Ala Phe Glu Trp Arg Asp
                165                 170                 175

Pro Glu Met Gly Ile Ser Gly Gln Leu Thr Trp Thr Arg Leu Pro Gln
            180                 185                 190

Gly Phe Lys Asn Ser Pro Thr Leu Phe Asp Glu Ala Leu His Arg Asp
        195                 200                 205

Leu Ala Asp Phe Arg Ile Gln His Pro Asp Leu Ile Leu Leu Gln Tyr
    210                 215                 220

Val Asp Asp Leu Leu Leu Ala Ala Thr Ser Glu Leu Asp Cys Gln Gln
225                 230                 235                 240

Gly Thr Arg Ala Leu Leu Gln Thr Leu Gly Asn Leu Gly Tyr Arg Ala
                245                 250                 255

Ser Ala Lys Lys Ala Gln Ile Cys Gln Lys Gln Val Lys Tyr Leu Gly
            260                 265                 270

```
Tyr Leu Leu Lys Glu Gly Gln Arg Trp Leu Thr Glu Ala Arg Lys Glu
                275                 280                 285

Thr Val Met Gly Gln Pro Thr Pro Lys Thr Pro Arg Gln Leu Arg Glu
            290                 295                 300

Phe Leu Gly Thr Ala Gly Phe Cys Arg Leu Trp Ile Pro Gly Phe Ala
305                 310                 315                 320

Glu Met Ala Ala Pro Leu Tyr Pro Leu Thr Lys Thr Gly Thr Leu Phe
                325                 330                 335

Asn Trp Gly Pro Asp Gln Gln Lys Ala Tyr Gln Glu Ile Lys Gln Ala
                340                 345                 350

Leu Leu Thr Ala Pro Ala Leu Gly Leu Pro Asp Leu Thr Lys Pro Phe
                355                 360                 365

Glu Leu Phe Val Asp Glu Lys Gln Gly Tyr Ala Lys Gly Val Leu Thr
            370                 375                 380

Gln Lys Leu Gly Pro Trp Arg Arg Pro Val Ala Tyr Leu Ser Lys Lys
385                 390                 395                 400

Leu Asp Pro Val Ala Ala Gly Trp Pro Pro Cys Leu Arg Met Val Ala
                405                 410                 415

Ala Ile Ala Val Leu Thr Lys Asp Ala Gly Lys Leu Thr Met Gly Gln
                420                 425                 430

Pro Leu Val Ile Leu Ala Pro His Ala Val Glu Ala Leu Val Lys Gln
                435                 440                 445

Pro Pro Asp Arg Trp Leu Ser Asn Ala Arg Met Thr His Tyr Gln Ala
                450                 455                 460

Leu Leu Leu Asp Thr Asp Arg Val Gln Phe Gly Pro Val Val Ala Leu
465                 470                 475                 480

Asn Pro Ala Thr Leu Leu Pro Leu Pro Glu Glu Gly Leu Gln His Asn
                485                 490                 495

Cys Leu Asp Ile Leu Ala Glu Ala His Gly Thr Arg Pro Asp Leu Thr
                500                 505                 510

Asp Gln Pro Leu Pro Asp Ala Asp His Thr Trp Tyr Thr Asp Gly Ser
                515                 520                 525

Ser Leu Leu Gln Glu Gly Gln Arg Lys Ala Gly Ala Ala Val Thr Thr
                530                 535                 540

Glu Thr Glu Val Ile Trp Ala Lys Ala Leu Pro Ala Gly Thr Ser Ala
545                 550                 555                 560

Gln Arg Ala Glu Leu Ile Ala Leu Thr Gln Ala Leu Lys Met Ala Glu
                565                 570                 575

Gly Lys Lys Leu Asn Val Tyr Thr Asp Ser Arg Tyr Ala Phe Ala Thr
                580                 585                 590

Ala His Ile His Gly Glu Ile Tyr Arg Arg Arg Gly Leu Leu Thr Ser
                595                 600                 605

Glu Gly Lys Glu Ile Lys Asn Lys Asp Glu Ile Leu Ala Leu Leu Lys
            610                 615                 620

Ala Leu Phe Leu Pro Lys Arg Leu Ser Ile Ile His Cys Pro Gly His
625                 630                 635                 640

Gln Lys Gly His Ser Ala Glu Ala Arg Gly Asn Arg Met Ala Asp Gln
                645                 650                 655

Ala Ala Arg Lys Ala Ala Ile Thr Glu Thr Pro Asp Thr Ser Thr Leu
                660                 665                 670

Leu Ser Ser Ser Ala Ser Lys Leu Glu Phe Thr Leu Gln Leu Glu Glu
                675                 680                 685

Glu Tyr Arg Leu Phe Glu Pro Glu Ser Thr Gln Lys Gln Glu Met Asp
```

```
                690             695             700
Ile Trp Leu Lys Asn Phe Pro Gln Ala Trp Ala Glu Thr Gly Gly Met
705                 710             715                 720

Gly Met Ala His Cys Gln Ala Pro Val Leu Ile Gln Leu Lys Ala Thr
                725             730                 735

Ala Thr Pro Ile Ser Ile Arg Gln Tyr Pro Met Pro His Glu Ala Tyr
                740             745             750

Gln Gly Ile Lys Pro His Ile Arg Arg Met Leu Asp Gln Gly Ile Leu
            755             760             765

Lys Pro Cys Gln Ser Pro Trp Asn Thr Pro Leu Leu Pro Val Lys Lys
770             775             780

Pro Gly Thr Lys Asp Tyr Arg Pro Val Gln Asp Leu Arg Glu Val Asn
785             790             795             800

Lys Arg Val Glu Asp Ile His Pro Thr Val Pro Asn Pro Tyr Asn Leu
                805             810             815

Leu Ser Thr Leu Pro Pro Ser His Pro Trp Tyr Thr Val Leu Asp Leu
                820             825             830

Lys Asp Ala Phe Phe Cys Leu Arg Leu His Ser Glu Ser Gln Leu Leu
            835             840             845

Phe Ala Phe Glu Trp Arg Asp Pro Glu Ile Gly Leu Ser Gly Gln Leu
            850             855             860

Thr Trp Thr Arg Leu Pro Gln Gly Phe Lys Asn Ser Pro Thr Leu Phe
865             870             875             880

Asp Glu Ala Leu His Ser Asp Leu Ala Asp Phe Arg Val Arg Tyr Pro
                885             890             895

Ala Leu Val Leu Leu Gln Tyr Val Asp Asp Leu Leu Leu Ala Ala Ala
            900             905             910

Thr Arg Thr Glu Cys Leu Glu Gly Thr Lys Ala Leu Leu Glu Thr Leu
            915             920             925

Gly Asn Lys Gly Tyr Arg Ala Ser Ala Lys Lys Ala Gln Ile Cys Leu
930             935             940

Gln Glu Val Thr Tyr Leu Gly Tyr Ser Leu Lys Asp Gly Gln Arg Trp
945             950             955             960

Leu Thr Lys Ala Arg Lys Glu Ala Ile Leu Ser Ile Pro Val Pro Lys
                965             970             975

Asn Pro Arg Gln Val Arg Glu Phe Leu Gly Thr Ala Gly Tyr Cys Arg
            980             985             990

Leu Trp Ile Pro Gly Phe Ala Glu Leu Ala Ala Pro Leu Tyr Pro Leu
            995             1000            1005

Thr Arg Pro Gly Thr Leu Phe Gln Trp Gly Thr Glu Gln Gln Leu
    1010            1015            1020

Ala Phe Glu Asn Ile Arg Lys Ala Leu Leu Ser Ser Pro Ala Leu
    1025            1030            1035

Gly Leu Pro Asp Ile Thr Lys Pro Phe Glu Leu Phe Ile Asp Glu
    1040            1045            1050

Asn Ser Gly Phe Ala Lys Gly Val Leu Val Gln Lys Leu Gly Pro
    1055            1060            1065

Trp Lys Arg Pro Val Ala Tyr Leu Ser Lys Leu Asp Thr Val
    1070            1075            1080

Ala Ser Gly Trp Pro Pro Cys Leu Arg Met Val Ala Ala Ile Ala
    1085            1090            1095

Ile Leu Val Lys Asp Ala Gly Lys Leu Thr Leu Gly Gln Pro Leu
    1100            1105            1110
```

-continued

```
Thr Ile Leu Thr Ser His Pro Val Glu Ala Leu Val Arg Gln Pro
    1115                1120                1125

Pro Asn Lys Trp Leu Ser Asn Ala Arg Met Thr His Tyr Gln Ala
    1130                1135                1140

Met Leu Leu Asp Ala Glu Arg Val His Phe Gly Pro Thr Val Ser
    1145                1150                1155

Leu Asn Pro Ala Thr Leu Leu Pro Leu Pro Ser Gly Lys Pro Pro
    1160                1165                1170

Arg Leu Ser Pro Asp Leu Ala Glu Thr Met Ala Gln Thr Asp Leu
    1175                1180                1185

Thr Asp Gln Pro Leu Pro Asp Ala Asp Leu Thr Trp Tyr Thr Asp
    1190                1195                1200

Gly Ser Ser Phe Ile Arg Asn Gly Glu Arg Lys Ala Gly Ala Ala
    1205                1210                1215

Val Thr Thr Glu Ser Glu Val Ile Trp Ala Ala Ser Leu Pro Pro
    1220                1225                1230

Gly Thr Ser Ala Gln Arg Ala Glu Leu Ile Ala Leu Thr Gln Ala
    1235                1240                1245

Leu Lys Met Ala Lys Gly Lys Lys Leu Thr Val Tyr Thr Asp Ser
    1250                1255                1260

Arg Tyr Ala Phe Ala Thr Ala His Val His Gly Glu Ile Tyr Arg
    1265                1270                1275

Arg Arg Gly Leu Leu Thr Ser Glu Gly Lys Glu Ile Lys Asn Lys
    1280                1285                1290

Asn Glu Ile Leu Ala Leu Leu Glu Ala Leu Phe Leu Pro Lys Arg
    1295                1300                1305

Leu Ser Ile Ile His Cys Pro Gly His Gln Lys Gly Asp Ser Pro
    1310                1315                1320

Gln Ala Lys Gly Asn Arg Leu Ala Asp Asp Thr Ala Lys Lys Ala
    1325                1330                1335

Ala Thr Glu Thr Gln Ser Ser Leu Thr Ile Leu Ser Ser Ser Ala
    1340                1345                1350

Ser
```

<210> SEQ ID NO 13
<211> LENGTH: 1354
<212> TYPE: PRT
<213> ORGANISM: Artificial Sequence
<220> FEATURE:
<223> OTHER INFORMATION: Synthetic construct

<400> SEQUENCE: 13

```
Glu Phe Thr Leu Asn Ile Glu Asp Glu His Arg Leu His Glu Thr Ser
1               5                   10                  15

Lys Glu Pro Asp Val Ser Leu Gly Ser Thr Trp Leu Ser Asp Phe Pro
                20                  25                  30

Gln Ala Trp Ala Glu Thr Gly Gly Met Gly Leu Ala Val Arg Gln Ala
            35                  40                  45

Pro Leu Ile Ile Pro Leu Lys Ala Thr Ser Thr Pro Val Ser Ile Lys
        50                  55                  60

Gln Tyr Pro Met Ser Gln Glu Ala Arg Leu Gly Ile Lys Pro His Ile
65                  70                  75                  80

Gln Arg Leu Leu Asp Gln Gly Ile Leu Val Pro Cys Gln Ser Pro Trp
                85                  90                  95
```

```
Asn Thr Pro Leu Leu Pro Val Lys Lys Pro Gly Thr Asn Asp Tyr Arg
                100                 105                 110

Pro Val Gln Asp Leu Arg Glu Val Asn Lys Arg Val Glu Asp Ile His
            115                 120                 125

Pro Thr Val Pro Asn Pro Tyr Asn Leu Leu Ser Gly Leu Pro Pro Ser
        130                 135                 140

His Gln Trp Tyr Thr Val Leu Asp Leu Lys Asp Ala Phe Phe Cys Leu
145                 150                 155                 160

Arg Leu His Pro Thr Ser Gln Pro Leu Phe Ala Phe Glu Trp Arg Asp
                165                 170                 175

Pro Glu Met Gly Ile Ser Gly Gln Leu Thr Trp Thr Arg Leu Pro Gln
            180                 185                 190

Gly Phe Lys Asn Ser Pro Thr Leu Phe Asp Glu Ala Leu His Arg Asp
        195                 200                 205

Leu Ala Asp Phe Arg Ile Gln His Pro Asp Leu Ile Leu Leu Gln Tyr
    210                 215                 220

Val Asp Asp Leu Leu Leu Ala Ala Thr Ser Glu Leu Asp Cys Gln Gln
225                 230                 235                 240

Gly Thr Arg Ala Leu Leu Gln Thr Leu Gly Asn Leu Gly Tyr Arg Ala
                245                 250                 255

Ser Ala Lys Lys Ala Gln Ile Cys Gln Lys Gln Val Lys Tyr Leu Gly
            260                 265                 270

Tyr Leu Leu Lys Glu Gly Gln Arg Trp Leu Thr Glu Ala Arg Lys Glu
        275                 280                 285

Thr Val Met Gly Gln Pro Thr Pro Lys Thr Pro Arg Gln Leu Arg Glu
    290                 295                 300

Phe Leu Gly Thr Ala Gly Phe Cys Arg Leu Trp Ile Pro Gly Phe Ala
305                 310                 315                 320

Glu Met Ala Ala Pro Leu Tyr Pro Leu Thr Lys Thr Gly Thr Leu Phe
                325                 330                 335

Asn Trp Gly Pro Asp Gln Gln Lys Ala Tyr Gln Glu Ile Lys Gln Ala
            340                 345                 350

Leu Leu Thr Ala Pro Ala Leu Gly Leu Pro Asp Leu Thr Lys Pro Phe
        355                 360                 365

Glu Leu Phe Val Asp Glu Lys Gln Gly Tyr Ala Lys Gly Val Leu Thr
    370                 375                 380

Gln Lys Leu Gly Pro Trp Arg Arg Pro Val Ala Tyr Leu Ser Lys Lys
385                 390                 395                 400

Leu Asp Pro Val Ala Ala Gly Trp Pro Pro Cys Leu Arg Met Val Ala
                405                 410                 415

Ala Ile Ala Val Leu Thr Lys Asp Ala Gly Lys Leu Thr Met Gly Gln
            420                 425                 430

Pro Leu Val Ile Leu Ala Pro His Ala Val Glu Ala Leu Val Lys Gln
        435                 440                 445

Pro Pro Asp Arg Trp Leu Ser Asn Ala Arg Met Thr His Tyr Gln Ala
    450                 455                 460

Leu Leu Leu Asp Thr Asp Arg Val Gln Phe Gly Pro Val Val Ala Leu
465                 470                 475                 480

Asn Pro Ala Thr Leu Leu Pro Leu Pro Glu Glu Gly Leu Gln His Asn
                485                 490                 495

Cys Leu Asp Ile Leu Ala Glu Ala His Gly Thr Arg Pro Asp Leu Thr
            500                 505                 510

Asp Gln Pro Leu Pro Asp Ala Asp His Thr Trp Tyr Thr Asn Gly Ser
```

```
                515                 520                 525
    Ser Leu Leu Gln Glu Gly Gln Arg Lys Ala Gly Ala Ala Val Thr Thr
        530                 535                 540
    Glu Thr Glu Val Ile Trp Ala Lys Ala Leu Pro Ala Gly Thr Ser Ala
    545                 550                 555                 560
    Gln Arg Ala Glu Leu Ile Ala Leu Thr Gln Ala Leu Lys Met Ala Glu
                        565                 570                 575
    Gly Lys Lys Leu Asn Val Tyr Thr Asp Ser Arg Tyr Ala Phe Ala Thr
                580                 585                 590
    Ala His Ile His Gly Glu Ile Tyr Arg Arg Arg Gly Leu Leu Thr Ser
            595                 600                 605
    Glu Gly Lys Glu Ile Lys Asn Lys Asp Glu Ile Leu Ala Leu Leu Lys
        610                 615                 620
    Ala Leu Phe Leu Pro Lys Arg Leu Ser Ile Ile His Cys Pro Gly His
    625                 630                 635                 640
    Gln Lys Gly His Ser Ala Glu Ala Arg Gly Asn Arg Met Ala Asp Gln
                        645                 650                 655
    Ala Ala Arg Lys Ala Ala Ile Thr Glu Thr Pro Asp Thr Ser Thr Leu
                660                 665                 670
    Leu Ser Ser Ser Ala Ser Lys Leu Glu Phe Thr Leu Gln Leu Glu Glu
            675                 680                 685
    Glu Tyr Arg Leu Phe Glu Pro Glu Ser Thr Gln Lys Gln Glu Met Asp
        690                 695                 700
    Ile Trp Leu Lys Asn Phe Pro Gln Ala Trp Ala Glu Thr Gly Gly Met
    705                 710                 715                 720
    Gly Met Ala His Cys Gln Ala Pro Val Leu Ile Gln Leu Lys Ala Thr
                        725                 730                 735
    Ala Thr Pro Ile Ser Ile Arg Gln Tyr Pro Met Pro His Glu Ala Tyr
                740                 745                 750
    Gln Gly Ile Lys Pro His Ile Arg Arg Met Leu Asp Gln Gly Ile Leu
            755                 760                 765
    Lys Pro Cys Gln Ser Pro Trp Asn Thr Pro Leu Leu Pro Val Lys Lys
        770                 775                 780
    Pro Gly Thr Lys Asp Tyr Arg Pro Val Gln Asp Leu Arg Glu Val Asn
    785                 790                 795                 800
    Lys Arg Val Glu Asp Ile His Pro Thr Val Pro Asn Pro Tyr Asn Leu
                        805                 810                 815
    Leu Ser Thr Leu Pro Pro Ser His Pro Trp Tyr Thr Val Leu Asp Leu
                820                 825                 830
    Lys Asp Ala Phe Phe Cys Leu Arg Leu His Ser Glu Ser Gln Leu Leu
            835                 840                 845
    Phe Ala Phe Glu Trp Arg Asp Pro Glu Ile Gly Leu Ser Gly Gln Leu
        850                 855                 860
    Thr Trp Thr Arg Leu Pro Gln Gly Phe Lys Asn Ser Pro Thr Leu Phe
    865                 870                 875                 880
    Asp Glu Ala Leu His Ser Asp Leu Ala Asp Phe Arg Val Arg Tyr Pro
                        885                 890                 895
    Ala Leu Val Leu Leu Gln Tyr Val Asp Asp Leu Leu Leu Ala Ala Ala
                900                 905                 910
    Thr Arg Thr Glu Cys Leu Glu Gly Thr Lys Ala Leu Leu Glu Thr Leu
            915                 920                 925
    Gly Asn Lys Gly Tyr Arg Ala Ser Ala Lys Lys Ala Gln Ile Cys Leu
        930                 935                 940
```

```
Gln Glu Val Thr Tyr Leu Gly Tyr Ser Leu Lys Asp Gly Gln Arg Trp
945                 950                 955                 960

Leu Thr Lys Ala Arg Lys Glu Ala Ile Leu Ser Ile Pro Val Pro Lys
            965                 970                 975

Asn Pro Arg Gln Val Arg Glu Phe Leu Gly Thr Ala Gly Tyr Cys Arg
        980                 985                 990

Leu Trp Ile Pro Gly Phe Ala Glu Leu Ala Ala Pro Leu Tyr Pro Leu
    995                 1000                1005

Thr Arg Pro Gly Thr Leu Phe Gln Trp Gly Thr Glu Gln Gln Leu
1010                1015                1020

Ala Phe Glu Asn Ile Arg Lys Ala Leu Leu Ser Ser Pro Ala Leu
1025                1030                1035

Gly Leu Pro Asp Ile Thr Lys Pro Phe Glu Leu Phe Ile Asp Glu
1040                1045                1050

Asn Ser Gly Phe Ala Lys Gly Val Leu Val Gln Lys Leu Gly Pro
1055                1060                1065

Trp Lys Arg Pro Val Ala Tyr Leu Ser Lys Lys Leu Asp Thr Val
1070                1075                1080

Ala Ser Gly Trp Pro Pro Cys Leu Arg Met Val Ala Ala Ile Ala
1085                1090                1095

Ile Leu Val Lys Asp Ala Gly Lys Leu Thr Leu Gly Gln Pro Leu
1100                1105                1110

Thr Ile Leu Thr Ser His Pro Val Glu Ala Leu Val Arg Gln Pro
1115                1120                1125

Pro Asn Lys Trp Leu Ser Asn Ala Arg Met Thr His Tyr Gln Ala
1130                1135                1140

Met Leu Leu Asp Ala Glu Arg Val His Phe Gly Pro Thr Val Ser
1145                1150                1155

Leu Asn Pro Ala Thr Leu Leu Pro Leu Pro Ser Gly Lys Pro Pro
1160                1165                1170

Arg Leu Ser Pro Asp Leu Ala Glu Thr Met Ala Gln Thr Asp Leu
1175                1180                1185

Thr Asp Gln Pro Leu Pro Asp Ala Asp Leu Thr Trp Tyr Thr Asp
1190                1195                1200

Gly Ser Ser Phe Ile Arg Asn Gly Glu Arg Lys Ala Gly Ala Ala
1205                1210                1215

Val Thr Thr Glu Ser Glu Val Ile Trp Ala Ala Ser Leu Pro Pro
1220                1225                1230

Gly Thr Ser Ala Gln Arg Ala Glu Leu Ile Ala Leu Thr Gln Ala
1235                1240                1245

Leu Lys Met Ala Lys Gly Lys Lys Leu Thr Val Tyr Thr Asp Ser
1250                1255                1260

Arg Tyr Ala Phe Ala Thr His Val His Gly Glu Ile Tyr Arg
1265                1270                1275

Arg Arg Gly Leu Leu Thr Ser Glu Gly Lys Glu Ile Lys Asn Lys
1280                1285                1290

Asn Glu Ile Leu Ala Leu Leu Glu Ala Leu Phe Leu Pro Lys Arg
1295                1300                1305

Leu Ser Ile Ile His Cys Pro Gly His Gln Lys Gly Asp Ser Pro
1310                1315                1320

Gln Ala Lys Gly Asn Arg Leu Ala Asp Asp Thr Ala Lys Lys Ala
1325                1330                1335
```

-continued

Ala Thr Glu Thr Gln Ser Ser Leu Thr Ile Leu Ser Ser Ser Ala
    1340                1345                1350

Ser

<210> SEQ ID NO 14
<211> LENGTH: 1354
<212> TYPE: PRT
<213> ORGANISM: Artificial Sequence
<220> FEATURE:
<223> OTHER INFORMATION: Synthetic construct

<400> SEQUENCE: 14

Glu Phe Thr Leu Asn Ile Glu Asp Glu His Arg Leu His Glu Thr Ser
1               5                   10                  15

Lys Glu Pro Asp Val Ser Leu Gly Ser Thr Trp Leu Ser Asp Phe Pro
            20                  25                  30

Gln Ala Trp Ala Glu Thr Gly Gly Met Gly Leu Ala Val Arg Gln Ala
        35                  40                  45

Pro Leu Ile Ile Pro Leu Lys Ala Thr Ser Thr Pro Val Ser Ile Lys
    50                  55                  60

Gln Tyr Pro Met Ser Gln Glu Ala Arg Leu Gly Ile Lys Pro His Ile
65                  70                  75                  80

Gln Arg Leu Leu Asp Gln Gly Ile Leu Val Pro Cys Gln Ser Pro Trp
                85                  90                  95

Asn Thr Pro Leu Leu Pro Val Lys Lys Pro Gly Thr Asn Asp Tyr Arg
            100                 105                 110

Pro Val Gln Asp Leu Arg Glu Val Asn Lys Arg Val Glu Asp Ile His
        115                 120                 125

Pro Thr Val Pro Asn Pro Tyr Asn Leu Leu Ser Gly Leu Pro Pro Ser
    130                 135                 140

His Gln Trp Tyr Thr Val Leu Asp Leu Lys Asp Ala Phe Phe Cys Leu
145                 150                 155                 160

Arg Leu His Pro Thr Ser Gln Pro Leu Phe Ala Phe Glu Trp Arg Asp
                165                 170                 175

Pro Glu Met Gly Ile Ser Gly Gln Leu Thr Trp Thr Arg Leu Pro Gln
            180                 185                 190

Gly Phe Lys Asn Ser Pro Thr Leu Phe Asp Glu Ala Leu His Arg Asp
        195                 200                 205

Leu Ala Asp Phe Arg Ile Gln His Pro Asp Leu Ile Leu Leu Gln Tyr
    210                 215                 220

Val Asp Asp Leu Leu Leu Ala Ala Thr Ser Glu Leu Asp Cys Gln Gln
225                 230                 235                 240

Gly Thr Arg Ala Leu Leu Gln Thr Leu Gly Asn Leu Gly Tyr Arg Ala
                245                 250                 255

Ser Ala Lys Lys Ala Gln Ile Cys Gln Lys Gln Val Lys Tyr Leu Gly
            260                 265                 270

Tyr Leu Leu Lys Glu Gly Gln Arg Trp Leu Thr Glu Ala Arg Lys Glu
        275                 280                 285

Thr Val Met Gly Gln Pro Thr Pro Lys Thr Pro Arg Gln Leu Arg Glu
    290                 295                 300

Phe Leu Gly Thr Ala Gly Phe Cys Arg Leu Trp Ile Pro Gly Phe Ala
305                 310                 315                 320

Glu Met Ala Ala Pro Leu Tyr Pro Leu Thr Lys Thr Gly Thr Leu Phe
                325                 330                 335

Asn Trp Gly Pro Asp Gln Gln Lys Ala Tyr Gln Glu Ile Lys Gln Ala

```
              340             345             350
Leu Leu Thr Ala Pro Ala Leu Gly Leu Pro Asp Leu Thr Lys Pro Phe
            355                 360                 365

Glu Leu Phe Val Asp Glu Lys Gln Gly Tyr Ala Lys Gly Val Leu Thr
            370                 375                 380

Gln Lys Leu Gly Pro Trp Arg Arg Pro Val Ala Tyr Leu Ser Lys Lys
385                 390                 395                 400

Leu Asp Pro Val Ala Ala Gly Trp Pro Pro Cys Leu Arg Met Val Ala
            405                 410                 415

Ala Ile Ala Val Leu Thr Lys Asp Ala Gly Lys Leu Thr Met Gly Gln
            420                 425                 430

Pro Leu Val Ile Leu Ala Pro His Ala Val Glu Ala Leu Val Lys Gln
            435                 440                 445

Pro Pro Asp Arg Trp Leu Ser Asn Ala Arg Met Thr His Tyr Gln Ala
            450                 455                 460

Leu Leu Leu Asp Thr Asp Arg Val Gln Phe Gly Pro Val Val Ala Leu
465                 470                 475                 480

Asn Pro Ala Thr Leu Leu Pro Leu Pro Glu Glu Gly Leu Gln His Asn
            485                 490                 495

Cys Leu Asp Ile Leu Ala Glu Ala His Gly Thr Arg Pro Asp Leu Thr
            500                 505                 510

Asp Gln Pro Leu Pro Asp Ala Asp His Thr Trp Tyr Thr Asn Gly Ser
            515                 520                 525

Ser Leu Leu Gln Glu Gly Gln Arg Lys Ala Gly Ala Ala Val Thr Thr
            530                 535                 540

Glu Thr Glu Val Ile Trp Ala Lys Ala Leu Pro Ala Gly Thr Ser Ala
545                 550                 555                 560

Gln Arg Ala Glu Leu Ile Ala Leu Thr Gln Ala Leu Lys Met Ala Glu
            565                 570                 575

Gly Lys Lys Leu Asn Val Tyr Thr Asp Ser Arg Tyr Ala Phe Ala Thr
            580                 585                 590

Ala His Ile His Gly Glu Ile Tyr Arg Arg Arg Gly Leu Leu Thr Ser
            595                 600                 605

Glu Gly Lys Glu Ile Lys Asn Lys Asp Glu Ile Leu Ala Leu Leu Lys
            610                 615                 620

Ala Leu Phe Leu Pro Lys Arg Leu Ser Ile Ile His Cys Pro Gly His
625                 630                 635                 640

Gln Lys Gly His Ser Ala Glu Ala Arg Gly Asn Arg Met Ala Asp Gln
            645                 650                 655

Ala Ala Arg Lys Ala Ala Ile Thr Glu Thr Pro Asp Thr Ser Thr Leu
            660                 665                 670

Leu Ser Ser Ser Ala Ser Lys Leu Glu Phe Thr Leu Gln Leu Glu Glu
            675                 680                 685

Glu Tyr Arg Leu Phe Glu Pro Glu Ser Thr Gln Lys Gln Glu Met Asp
            690                 695                 700

Ile Trp Leu Lys Asn Phe Pro Gln Ala Trp Ala Glu Thr Gly Gly Met
705                 710                 715                 720

Gly Met Ala His Cys Gln Ala Pro Val Leu Ile Gln Leu Lys Ala Thr
            725                 730                 735

Ala Thr Pro Ile Ser Ile Arg Gln Tyr Pro Met Pro His Glu Ala Tyr
            740                 745                 750

Gln Gly Ile Lys Pro His Ile Arg Arg Met Leu Asp Gln Gly Ile Leu
            755                 760                 765
```

```
Lys Pro Cys Gln Ser Pro Trp Asn Thr Pro Leu Leu Pro Val Lys Lys
        770                 775                 780

Pro Gly Thr Lys Asp Tyr Arg Pro Val Gln Asp Leu Arg Glu Val Asn
785                 790                 795                 800

Lys Arg Val Glu Asp Ile His Pro Thr Val Pro Asn Pro Tyr Asn Leu
                805                 810                 815

Leu Ser Thr Leu Pro Pro Ser His Pro Trp Tyr Thr Val Leu Asp Leu
                820                 825                 830

Lys Asp Ala Phe Phe Cys Leu Arg Leu His Ser Glu Ser Gln Leu Leu
                835                 840                 845

Phe Ala Phe Glu Trp Arg Asp Pro Glu Ile Gly Leu Ser Gly Gln Leu
                850                 855                 860

Thr Trp Thr Arg Leu Pro Gln Gly Phe Lys Asn Ser Pro Thr Leu Phe
865                 870                 875                 880

Asp Glu Ala Leu His Ser Asp Leu Ala Asp Phe Arg Val Arg Tyr Pro
                885                 890                 895

Ala Leu Val Leu Leu Gln Tyr Val Asp Asp Leu Leu Leu Ala Ala Ala
                900                 905                 910

Thr Arg Thr Glu Cys Leu Glu Gly Thr Lys Ala Leu Leu Glu Thr Leu
                915                 920                 925

Gly Asn Lys Gly Tyr Arg Ala Ser Ala Lys Lys Ala Gln Ile Cys Leu
930                 935                 940

Gln Glu Val Thr Tyr Leu Gly Tyr Ser Leu Lys Asp Gly Gln Arg Trp
945                 950                 955                 960

Leu Thr Lys Ala Arg Lys Glu Ala Ile Leu Ser Ile Pro Val Pro Lys
                965                 970                 975

Asn Pro Arg Gln Val Arg Glu Phe Leu Gly Thr Ala Gly Tyr Cys Arg
                980                 985                 990

Leu Trp Ile Pro Gly Phe Ala Glu Leu Ala Ala Pro Leu Tyr Pro Leu
                995                 1000                1005

Thr Arg Pro Gly Thr Leu Phe Gln Trp Gly Thr Glu Gln Gln Leu
        1010                1015                1020

Ala Phe Glu Asn Ile Arg Lys Ala Leu Leu Ser Ser Pro Ala Leu
        1025                1030                1035

Gly Leu Pro Asp Ile Thr Lys Pro Phe Glu Leu Phe Ile Asp Glu
        1040                1045                1050

Asn Ser Gly Phe Ala Lys Gly Val Leu Val Gln Lys Leu Gly Pro
        1055                1060                1065

Trp Lys Arg Pro Val Ala Tyr Leu Ser Lys Lys Leu Asp Thr Val
        1070                1075                1080

Ala Ser Gly Trp Pro Pro Cys Leu Arg Met Val Ala Ala Ile Ala
        1085                1090                1095

Ile Leu Val Lys Asp Ala Gly Lys Leu Thr Leu Gly Gln Pro Leu
        1100                1105                1110

Thr Ile Leu Thr Ser His Pro Val Glu Ala Leu Val Arg Gln Pro
        1115                1120                1125

Pro Asn Lys Trp Leu Ser Asn Ala Arg Met Thr His Tyr Gln Ala
        1130                1135                1140

Met Leu Leu Asp Ala Glu Arg Val His Phe Gly Pro Thr Val Ser
        1145                1150                1155

Leu Asn Pro Ala Thr Leu Leu Pro Leu Pro Ser Gly Lys Pro Pro
        1160                1165                1170
```

```
Arg Leu Ser Pro Asp Leu Ala Glu Thr Met Ala Gln Thr Asp Leu
    1175                1180                1185

Thr Asp Gln Pro Leu Pro Asp Ala Asp Leu Thr Trp Tyr Thr Asn
    1190                1195                1200

Gly Ser Ser Phe Ile Arg Asn Gly Glu Arg Lys Ala Gly Ala Ala
    1205                1210                1215

Val Thr Thr Glu Ser Glu Val Ile Trp Ala Ala Ser Leu Pro Pro
    1220                1225                1230

Gly Thr Ser Ala Gln Arg Ala Glu Leu Ile Ala Leu Thr Gln Ala
    1235                1240                1245

Leu Lys Met Ala Lys Gly Lys Lys Leu Thr Val Tyr Thr Asp Ser
    1250                1255                1260

Arg Tyr Ala Phe Ala Thr Ala His Val His Gly Glu Ile Tyr Arg
    1265                1270                1275

Arg Arg Gly Leu Leu Thr Ser Glu Gly Lys Glu Ile Lys Asn Lys
    1280                1285                1290

Asn Glu Ile Leu Ala Leu Leu Glu Ala Leu Phe Leu Pro Lys Arg
    1295                1300                1305

Leu Ser Ile Ile His Cys Pro Gly His Gln Lys Gly Asp Ser Pro
    1310                1315                1320

Gln Ala Lys Gly Asn Arg Leu Ala Asp Asp Thr Ala Lys Lys Ala
    1325                1330                1335

Ala Thr Glu Thr Gln Ser Ser Leu Thr Ile Leu Ser Ser Ser Ala
    1340                1345                1350

Ser

<210> SEQ ID NO 15
<211> LENGTH: 1350
<212> TYPE: PRT
<213> ORGANISM: Artificial Sequence
<220> FEATURE:
<223> OTHER INFORMATION: Synthetic construct

<400> SEQUENCE: 15

Glu Phe Thr Leu Gln Leu Glu Glu Tyr Arg Leu Phe Glu Pro Glu
1               5                   10                  15

Ser Thr Gln Lys Gln Glu Met Asp Ile Trp Leu Lys Asn Phe Pro Gln
                20                  25                  30

Ala Trp Ala Glu Thr Gly Gly Met Gly Met Ala His Cys Gln Ala Pro
                35                  40                  45

Val Leu Ile Gln Leu Lys Ala Thr Ala Thr Pro Ile Ser Ile Arg Gln
50                  55                  60

Tyr Pro Met Pro His Glu Ala Tyr Gln Gly Ile Lys Pro His Ile Arg
65                  70                  75                  80

Arg Met Leu Asp Gln Gly Ile Leu Lys Pro Cys Gln Ser Pro Trp Asn
                85                  90                  95

Thr Pro Leu Leu Pro Val Lys Lys Pro Gly Thr Lys Asp Tyr Arg Pro
                100                 105                 110

Val Gln Asp Leu Arg Glu Val Asn Lys Arg Val Glu Asp Ile His Pro
                115                 120                 125

Thr Val Pro Asn Pro Tyr Asn Leu Leu Ser Thr Leu Pro Pro Ser His
                130                 135                 140

Pro Trp Tyr Thr Val Leu Asp Leu Lys Asp Ala Phe Phe Cys Leu Arg
145                 150                 155                 160

Leu His Ser Glu Ser Gln Leu Leu Phe Ala Phe Glu Trp Arg Asp Pro
```

```
            165                 170                 175
Glu Ile Gly Leu Ser Gly Gln Leu Thr Trp Thr Arg Leu Pro Gln Gly
            180                 185                 190
Phe Lys Asn Ser Pro Thr Leu Phe Asp Glu Ala Leu His Ser Asp Leu
            195                 200                 205
Ala Asp Phe Arg Val Arg Tyr Pro Ala Leu Val Leu Leu Gln Tyr Val
210                 215                 220
Asp Asp Leu Leu Leu Ala Ala Thr Arg Thr Glu Cys Leu Glu Gly
225                 230                 235                 240
Thr Lys Ala Leu Leu Glu Thr Leu Gly Asn Lys Gly Tyr Arg Ala Ser
            245                 250                 255
Ala Lys Lys Ala Gln Ile Cys Leu Gln Glu Val Thr Tyr Leu Gly Tyr
            260                 265                 270
Ser Leu Lys Asp Gly Gln Arg Trp Leu Thr Lys Ala Arg Lys Glu Ala
            275                 280                 285
Ile Leu Ser Ile Pro Val Pro Lys Asn Pro Arg Gln Val Arg Glu Phe
            290                 295                 300
Leu Gly Thr Ala Gly Tyr Cys Arg Leu Trp Ile Pro Gly Phe Ala Glu
305                 310                 315                 320
Leu Ala Ala Pro Leu Tyr Pro Leu Thr Arg Pro Gly Thr Leu Phe Gln
            325                 330                 335
Trp Gly Thr Glu Gln Gln Leu Ala Phe Glu Asn Ile Arg Lys Ala Leu
            340                 345                 350
Leu Ser Ser Pro Ala Leu Gly Leu Pro Asp Ile Thr Lys Pro Phe Glu
            355                 360                 365
Leu Phe Ile Asp Glu Asn Ser Gly Phe Ala Lys Gly Val Leu Val Gln
            370                 375                 380
Lys Leu Gly Pro Trp Lys Arg Pro Val Ala Tyr Leu Ser Lys Lys Leu
385                 390                 395                 400
Asp Thr Val Ala Ser Gly Trp Pro Pro Cys Leu Arg Met Val Ala Ala
            405                 410                 415
Ile Ala Ile Leu Val Lys Asp Ala Gly Lys Leu Thr Leu Gly Gln Pro
            420                 425                 430
Leu Thr Ile Leu Thr Ser His Pro Val Glu Ala Leu Val Arg Gln Pro
            435                 440                 445
Pro Asn Lys Trp Leu Ser Asn Ala Arg Met Thr His Tyr Gln Ala Met
            450                 455                 460
Leu Leu Asp Ala Glu Arg Val His Phe Gly Pro Thr Val Ser Leu Asn
465                 470                 475                 480
Pro Ala Thr Leu Leu Pro Leu Pro Ser Gly Lys Pro Arg Leu Ser
            485                 490                 495
Pro Asp Leu Ala Glu Thr Met Ala Gln Thr Asp Leu Thr Asp Gln Pro
            500                 505                 510
Leu Pro Asp Ala Asp Leu Thr Trp Tyr Thr Asp Gly Ser Ser Phe Ile
            515                 520                 525
Arg Asn Gly Glu Arg Lys Ala Gly Ala Ala Val Thr Thr Glu Ser Glu
530                 535                 540
Val Ile Trp Ala Ala Ser Leu Pro Pro Gly Thr Ser Ala Gln Arg Ala
545                 550                 555                 560
Glu Leu Ile Ala Leu Thr Gln Ala Leu Lys Met Ala Lys Gly Lys Lys
            565                 570                 575
Leu Thr Val Tyr Thr Asp Ser Arg Tyr Ala Phe Ala Thr Ala His Val
            580                 585                 590
```

```
His Gly Glu Ile Tyr Arg Arg Gly Leu Leu Thr Ser Glu Gly Lys
            595                 600                 605

Glu Ile Lys Asn Lys Asn Glu Ile Leu Ala Leu Leu Glu Ala Leu Phe
        610                 615                 620

Leu Pro Lys Arg Leu Ser Ile Ile His Cys Pro Gly His Gln Lys Gly
625                 630                 635                 640

Asp Ser Pro Gln Ala Lys Gly Asn Arg Leu Ala Asp Asp Thr Ala Lys
                645                 650                 655

Lys Ala Ala Thr Glu Thr Gln Ser Ser Leu Thr Ile Leu Ser Ser Ser
                660                 665                 670

Ala Ser Lys Leu Glu Phe Thr Leu Gln Leu Glu Glu Tyr Arg Leu
            675                 680                 685

Phe Glu Pro Glu Ser Thr Gln Lys Gln Glu Met Asp Ile Trp Leu Lys
        690                 695                 700

Asn Phe Pro Gln Ala Trp Ala Glu Thr Gly Gly Met Gly Met Ala His
705                 710                 715                 720

Cys Gln Ala Pro Val Leu Ile Gln Leu Lys Ala Thr Ala Thr Pro Ile
                725                 730                 735

Ser Ile Arg Gln Tyr Pro Met Pro His Glu Ala Tyr Gln Gly Ile Lys
            740                 745                 750

Pro His Ile Arg Arg Met Leu Asp Gln Gly Ile Leu Lys Pro Cys Gln
        755                 760                 765

Ser Pro Trp Asn Thr Pro Leu Leu Pro Val Lys Lys Pro Gly Thr Lys
770                 775                 780

Asp Tyr Arg Pro Val Gln Asp Leu Arg Glu Val Asn Lys Arg Val Glu
785                 790                 795                 800

Asp Ile His Pro Thr Val Pro Asn Pro Tyr Asn Leu Leu Ser Thr Leu
                805                 810                 815

Pro Pro Ser His Pro Trp Tyr Thr Val Leu Asp Leu Lys Asp Ala Phe
            820                 825                 830

Phe Cys Leu Arg Leu His Ser Glu Ser Gln Leu Leu Phe Ala Phe Glu
        835                 840                 845

Trp Arg Asp Pro Glu Ile Gly Leu Ser Gly Gln Leu Thr Trp Thr Arg
850                 855                 860

Leu Pro Gln Gly Phe Lys Asn Ser Pro Thr Leu Phe Asp Glu Ala Leu
865                 870                 875                 880

His Ser Asp Leu Ala Asp Phe Arg Val Arg Tyr Pro Ala Leu Val Leu
                885                 890                 895

Leu Gln Tyr Val Asp Asp Leu Leu Ala Ala Thr Arg Thr Glu
            900                 905                 910

Cys Leu Glu Gly Thr Lys Ala Leu Leu Glu Thr Leu Gly Asn Lys Gly
        915                 920                 925

Tyr Arg Ala Ser Ala Lys Lys Ala Gln Ile Cys Leu Gln Glu Val Thr
930                 935                 940

Tyr Leu Gly Tyr Ser Leu Lys Asp Gly Gln Arg Trp Leu Thr Lys Ala
945                 950                 955                 960

Arg Lys Glu Ala Ile Leu Ser Ile Pro Val Pro Lys Asn Pro Arg Gln
                965                 970                 975

Val Arg Glu Phe Leu Gly Thr Ala Gly Tyr Cys Arg Leu Trp Ile Pro
            980                 985                 990

Gly Phe Ala Glu Leu Ala Ala Pro Leu Tyr Pro Leu Thr Arg Pro Gly
        995                 1000                1005
```

Thr Leu Phe Gln Trp Gly Thr Glu Gln Gln Leu Ala Phe Glu Asn
1010                1015                1020

Ile Arg Lys Ala Leu Leu Ser Ser Pro Ala Leu Gly Leu Pro Asp
1025                1030                1035

Ile Thr Lys Pro Phe Glu Leu Phe Ile Asp Glu Asn Ser Gly Phe
1040                1045                1050

Ala Lys Gly Val Leu Val Gln Lys Leu Gly Pro Trp Lys Arg Pro
1055                1060                1065

Val Ala Tyr Leu Ser Lys Lys Leu Asp Thr Val Ala Ser Gly Trp
1070                1075                1080

Pro Pro Cys Leu Arg Met Val Ala Ala Ile Ala Ile Leu Val Lys
1085                1090                1095

Asp Ala Gly Lys Leu Thr Leu Gly Gln Pro Leu Thr Ile Leu Thr
1100                1105                1110

Ser His Pro Val Glu Ala Leu Val Arg Gln Pro Pro Asn Lys Trp
1115                1120                1125

Leu Ser Asn Ala Arg Met Thr His Tyr Gln Ala Met Leu Leu Asp
1130                1135                1140

Ala Glu Arg Val His Phe Gly Pro Thr Val Ser Leu Asn Pro Ala
1145                1150                1155

Thr Leu Leu Pro Leu Pro Ser Gly Lys Pro Pro Arg Leu Ser Pro
1160                1165                1170

Asp Leu Ala Glu Thr Met Ala Gln Thr Asp Leu Thr Asp Gln Pro
1175                1180                1185

Leu Pro Asp Ala Asp Leu Thr Trp Tyr Thr Asn Gly Ser Ser Phe
1190                1195                1200

Ile Arg Asn Gly Glu Arg Lys Ala Gly Ala Ala Val Thr Thr Glu
1205                1210                1215

Ser Glu Val Ile Trp Ala Ala Ser Leu Pro Pro Gly Thr Ser Ala
1220                1225                1230

Gln Arg Ala Glu Leu Ile Ala Leu Thr Gln Ala Leu Lys Met Ala
1235                1240                1245

Lys Gly Lys Lys Leu Thr Val Tyr Thr Asp Ser Arg Tyr Ala Phe
1250                1255                1260

Ala Thr Ala His Val His Gly Glu Ile Tyr Arg Arg Arg Gly Leu
1265                1270                1275

Leu Thr Ser Glu Gly Lys Glu Ile Lys Asn Lys Asn Glu Ile Leu
1280                1285                1290

Ala Leu Leu Glu Ala Leu Phe Leu Pro Lys Arg Leu Ser Ile Ile
1295                1300                1305

His Cys Pro Gly His Gln Lys Gly Asp Ser Pro Gln Ala Lys Gly
1310                1315                1320

Asn Arg Leu Ala Asp Asp Thr Ala Lys Lys Ala Ala Thr Glu Thr
1325                1330                1335

Gln Ser Ser Leu Thr Ile Leu Ser Ser Ser Ala Ser
1340                1345                1350

<210> SEQ ID NO 16
<211> LENGTH: 1354
<212> TYPE: PRT
<213> ORGANISM: Artificial Sequence
<220> FEATURE:
<223> OTHER INFORMATION: Synthetic construct

<400> SEQUENCE: 16

-continued

```
Glu Phe Thr Leu Gln Leu Glu Glu Tyr Arg Leu Phe Glu Pro Glu
1               5                   10                  15

Ser Thr Gln Lys Gln Glu Met Asp Ile Trp Leu Lys Asn Phe Pro Gln
            20                  25                  30

Ala Trp Ala Glu Thr Gly Gly Met Gly Met Ala His Cys Gln Ala Pro
        35                  40                  45

Val Leu Ile Gln Leu Lys Ala Thr Ala Pro Ile Ser Ile Arg Gln
50                  55                  60

Tyr Pro Met Pro His Glu Ala Tyr Gln Gly Ile Lys Pro His Ile Arg
65                  70                  75                  80

Arg Met Leu Asp Gln Gly Ile Leu Lys Pro Cys Gln Ser Pro Trp Asn
                85                  90                  95

Thr Pro Leu Leu Pro Val Lys Lys Pro Gly Thr Lys Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Thr Leu Pro Pro Ser His
    130                 135                 140

Pro Trp Tyr Thr Val Leu Asp Leu Lys Asp Ala Phe Phe Cys Leu Arg
145                 150                 155                 160

Leu His Ser Glu Ser Gln Leu Leu Phe Ala Phe Glu Trp Arg Asp Pro
                165                 170                 175

Glu Ile Gly Leu Ser Gly Gln Leu Thr Trp Thr Arg Leu Pro Gln Gly
                180                 185                 190

Phe Lys Asn Ser Pro Thr Leu Phe Asp Glu Ala Leu His Ser Asp Leu
            195                 200                 205

Ala Asp Phe Arg Val Arg Tyr Pro Ala Leu Val Leu Leu Gln Tyr Val
    210                 215                 220

Asp Asp Leu Leu Leu Ala Ala Thr Arg Thr Glu Cys Leu Glu Gly
225                 230                 235                 240

Thr Lys Ala Leu Leu Glu Thr Leu Gly Asn Lys Gly Tyr Arg Ala Ser
                245                 250                 255

Ala Lys Lys Ala Gln Ile Cys Leu Gln Glu Val Thr Tyr Leu Gly Tyr
            260                 265                 270

Ser Leu Lys Asp Gly Gln Arg Trp Leu Thr Lys Ala Arg Lys Glu Ala
    275                 280                 285

Ile Leu Ser Ile Pro Val Pro Lys Asn Pro Arg Gln Val Arg Glu Phe
    290                 295                 300

Leu Gly Thr Ala Gly Tyr Cys Arg Leu Trp Ile Pro Gly Phe Ala Glu
305                 310                 315                 320

Leu Ala Ala Pro Leu Tyr Pro Leu Thr Arg Pro Gly Thr Leu Phe Gln
                325                 330                 335

Trp Gly Thr Glu Gln Gln Leu Ala Phe Glu Asn Ile Arg Lys Ala Leu
            340                 345                 350

Leu Ser Ser Pro Ala Leu Gly Leu Pro Asp Ile Thr Lys Pro Phe Glu
    355                 360                 365

Leu Phe Ile Asp Glu Asn Ser Gly Phe Ala Lys Gly Val Leu Val Gln
    370                 375                 380

Lys Leu Gly Pro Trp Lys Arg Pro Val Ala Tyr Leu Ser Lys Lys Leu
385                 390                 395                 400

Asp Thr Val Ala Ser Gly Trp Pro Pro Cys Leu Arg Met Val Ala Ala
                405                 410                 415

Ile Ala Ile Leu Val Lys Asp Ala Gly Lys Leu Thr Leu Gly Gln Pro
```

-continued

```
                420                 425                 430
Leu Thr Ile Leu Thr Ser His Pro Val Glu Ala Leu Val Arg Gln Pro
            435                 440                 445
Pro Asn Lys Trp Leu Ser Asn Ala Arg Met Thr His Tyr Gln Ala Met
    450                 455                 460
Leu Leu Asp Ala Glu Arg Val His Phe Gly Pro Thr Val Ser Leu Asn
465                 470                 475                 480
Pro Ala Thr Leu Leu Pro Leu Pro Ser Gly Lys Pro Pro Arg Leu Ser
                485                 490                 495
Pro Asp Leu Ala Glu Thr Met Ala Gln Thr Asp Leu Thr Asp Gln Pro
            500                 505                 510
Leu Pro Asp Ala Asp Leu Thr Trp Tyr Thr Asp Gly Ser Ser Phe Ile
        515                 520                 525
Arg Asn Gly Glu Arg Lys Ala Gly Ala Ala Val Thr Thr Glu Ser Glu
    530                 535                 540
Val Ile Trp Ala Ala Ser Leu Pro Pro Gly Thr Ser Ala Gln Arg Ala
545                 550                 555                 560
Glu Leu Ile Ala Leu Thr Gln Ala Leu Lys Met Ala Lys Gly Lys Lys
                565                 570                 575
Leu Thr Val Tyr Thr Asp Ser Arg Tyr Ala Phe Ala Thr Ala His Val
            580                 585                 590
His Gly Glu Ile Tyr Arg Arg Arg Gly Leu Leu Thr Ser Glu Gly Lys
        595                 600                 605
Glu Ile Lys Asn Lys Asn Glu Ile Leu Ala Leu Leu Glu Ala Leu Phe
    610                 615                 620
Leu Pro Lys Arg Leu Ser Ile Ile His Cys Pro Gly His Gln Lys Gly
625                 630                 635                 640
Asp Ser Pro Gln Ala Lys Gly Asn Arg Leu Ala Asp Asp Thr Ala Lys
                645                 650                 655
Lys Ala Ala Thr Glu Thr Gln Ser Ser Leu Thr Ile Leu Ser Ser Ser
            660                 665                 670
Ala Ser Lys Leu Glu Phe Thr Leu Asn Ile Glu Asp Glu His Arg Leu
        675                 680                 685
His Glu Thr Ser Lys Glu Pro Asp Val Ser Leu Gly Ser Thr Trp Leu
    690                 695                 700
Ser Asp Phe Pro Gln Ala Trp Ala Glu Thr Gly Gly Met Gly Leu Ala
705                 710                 715                 720
Val Arg Gln Ala Pro Leu Ile Ile Pro Leu Lys Ala Thr Ser Thr Pro
                725                 730                 735
Val Ser Ile Lys Gln Tyr Pro Met Ser Gln Glu Ala Arg Leu Gly Ile
            740                 745                 750
Lys Pro His Ile Gln Arg Leu Leu Asp Gln Gly Ile Leu Val Pro Cys
        755                 760                 765
Gln Ser Pro Trp Asn Thr Pro Leu Leu Pro Val Lys Lys Pro Gly Thr
    770                 775                 780
Asn Asp Tyr Arg Pro Val Gln Asp Leu Arg Glu Val Asn Lys Arg Val
785                 790                 795                 800
Glu Asp Ile His Pro Thr Val Pro Asn Pro Tyr Asn Leu Leu Ser Gly
                805                 810                 815
Leu Pro Pro Ser His Gln Trp Tyr Thr Val Leu Asp Leu Lys Asp Ala
            820                 825                 830
Phe Phe Cys Leu Arg Leu His Pro Thr Ser Gln Pro Leu Phe Ala Phe
        835                 840                 845
```

-continued

Glu Trp Arg Asp Pro Glu Met Gly Ile Ser Gly Gln Leu Thr Trp Thr
850                 855                 860

Arg Leu Pro Gln Gly Phe Lys Asn Ser Pro Thr Leu Phe Asp Glu Ala
865                 870                 875                 880

Leu His Arg Asp Leu Ala Asp Phe Arg Ile Gln His Pro Asp Leu Ile
                885                 890                 895

Leu Leu Gln Tyr Val Asp Asp Leu Leu Leu Ala Ala Thr Ser Glu Leu
                900                 905                 910

Asp Cys Gln Gln Gly Thr Arg Ala Leu Leu Gln Thr Leu Gly Asn Leu
                915                 920                 925

Gly Tyr Arg Ala Ser Ala Lys Lys Ala Gln Ile Cys Gln Lys Gln Val
930                 935                 940

Lys Tyr Leu Gly Tyr Leu Leu Lys Glu Gly Gln Arg Trp Leu Thr Glu
945                 950                 955                 960

Ala Arg Lys Glu Thr Val Met Gly Gln Pro Thr Pro Lys Thr Pro Arg
                965                 970                 975

Gln Leu Arg Glu Phe Leu Gly Thr Ala Gly Phe Cys Arg Leu Trp Ile
                980                 985                 990

Pro Gly Phe Ala Glu Met Ala Ala Pro Leu Tyr Pro Leu Thr Lys Thr
                995                 1000                1005

Gly Thr Leu Phe Asn Trp Gly Pro Asp Gln Gln Lys Ala Tyr Gln
    1010                1015                1020

Glu Ile Lys Gln Ala Leu Leu Thr Ala Pro Ala Leu Gly Leu Pro
    1025                1030                1035

Asp Leu Thr Lys Pro Phe Glu Leu Phe Val Asp Glu Lys Gln Gly
    1040                1045                1050

Tyr Ala Lys Gly Val Leu Thr Gln Lys Leu Gly Pro Trp Arg Arg
    1055                1060                1065

Pro Val Ala Tyr Leu Ser Lys Lys Leu Asp Pro Val Ala Ala Gly
    1070                1075                1080

Trp Pro Pro Cys Leu Arg Met Val Ala Ala Ile Ala Val Leu Thr
    1085                1090                1095

Lys Asp Ala Gly Lys Leu Thr Met Gly Gln Pro Leu Val Ile Leu
    1100                1105                1110

Ala Pro His Ala Val Glu Ala Leu Val Lys Gln Pro Pro Asp Arg
    1115                1120                1125

Trp Leu Ser Asn Ala Arg Met Thr His Tyr Gln Ala Leu Leu Leu
    1130                1135                1140

Asp Thr Asp Arg Val Gln Phe Gly Pro Val Val Ala Leu Asn Pro
    1145                1150                1155

Ala Thr Leu Leu Pro Leu Pro Glu Glu Gly Leu Gln His Asn Cys
    1160                1165                1170

Leu Asp Ile Leu Ala Glu Ala His Gly Thr Arg Pro Asp Leu Thr
    1175                1180                1185

Asp Gln Pro Leu Pro Asp Ala Asp His Thr Trp Tyr Thr Asn Gly
    1190                1195                1200

Ser Ser Leu Leu Gln Glu Gly Gln Arg Lys Ala Gly Ala Ala Val
    1205                1210                1215

Thr Thr Glu Thr Glu Val Ile Trp Ala Lys Ala Leu Pro Ala Gly
    1220                1225                1230

Thr Ser Ala Gln Arg Ala Glu Leu Ile Ala Leu Thr Gln Ala Leu
    1235                1240                1245

```
Lys Met Ala Glu Gly Lys Lys Leu Asn Val Tyr Thr Asp Ser Arg
    1250                1255                1260

Tyr Ala Phe Ala Thr Ala His Ile His Gly Glu Ile Tyr Arg Arg
    1265                1270                1275

Arg Gly Leu Leu Thr Ser Glu Gly Lys Glu Ile Lys Asn Lys Asp
    1280                1285                1290

Glu Ile Leu Ala Leu Leu Lys Ala Leu Phe Leu Pro Lys Arg Leu
    1295                1300                1305

Ser Ile Ile His Cys Pro Gly His Gln Lys Gly His Ser Ala Glu
    1310                1315                1320

Ala Arg Gly Asn Arg Met Ala Asp Gln Ala Ala Arg Lys Ala Ala
    1325                1330                1335

Ile Thr Glu Thr Pro Asp Thr Ser Thr Leu Leu Ser Ser Ser Ala
    1340                1345                1350

Ser
```

<210> SEQ ID NO 17
<211> LENGTH: 1354
<212> TYPE: PRT
<213> ORGANISM: Artificial Sequence
<220> FEATURE:
<223> OTHER INFORMATION: Synthetic construct

<400> SEQUENCE: 17

```
Glu Phe Thr Leu Asn Ile Glu Asp Glu His Arg Leu His Glu Thr Ser
1               5                   10                  15

Lys Glu Pro Asp Val Ser Leu Gly Ser Thr Trp Leu Ser Asp Phe Pro
            20                  25                  30

Gln Ala Trp Ala Glu Thr Gly Gly Met Gly Leu Ala Val Arg Gln Ala
        35                  40                  45

Pro Leu Ile Ile Pro Leu Lys Ala Thr Ser Thr Pro Val Ser Ile Lys
    50                  55                  60

Gln Tyr Pro Met Ser Gln Glu Ala Arg Leu Gly Ile Lys Pro His Ile
65                  70                  75                  80

Gln Arg Leu Leu Asp Gln Gly Ile Leu Val Pro Cys Gln Ser Pro Trp
                85                  90                  95

Asn Thr Pro Leu Leu Pro Val Lys Lys Pro Gly Thr Asn Asp Tyr Arg
            100                 105                 110

Pro Val Gln Asp Leu Arg Glu Val Asn Lys Arg Val Glu Asp Ile His
        115                 120                 125

Pro Thr Val Pro Asn Pro Tyr Asn Leu Leu Ser Gly Leu Pro Pro Ser
    130                 135                 140

His Gln Trp Tyr Thr Val Leu Asp Leu Lys Asp Ala Phe Phe Cys Leu
145                 150                 155                 160

Arg Leu His Pro Thr Ser Gln Pro Leu Phe Ala Phe Glu Trp Arg Asp
                165                 170                 175

Pro Glu Met Gly Ile Ser Gly Gln Leu Thr Trp Thr Arg Leu Pro Gln
            180                 185                 190

Gly Phe Lys Asn Ser Pro Thr Leu Phe Asp Glu Ala Leu His Arg Asp
        195                 200                 205

Leu Ala Asp Phe Arg Ile Gln His Pro Asp Leu Ile Leu Leu Gln Tyr
    210                 215                 220

Val Asp Asp Leu Leu Leu Ala Ala Thr Ser Glu Leu Asp Cys Gln Gln
225                 230                 235                 240

Gly Thr Arg Ala Leu Leu Gln Thr Leu Gly Asn Leu Gly Tyr Arg Ala
```

-continued

```
                245                 250                 255
Ser Ala Lys Lys Ala Gln Ile Cys Gln Lys Gln Val Lys Tyr Leu Gly
            260                 265                 270

Tyr Leu Leu Lys Glu Gly Gln Arg Trp Leu Thr Glu Ala Arg Lys Glu
            275                 280                 285

Thr Val Met Gly Gln Pro Thr Pro Lys Thr Pro Arg Gln Leu Arg Glu
            290                 295                 300

Phe Leu Gly Thr Ala Gly Phe Cys Arg Leu Trp Ile Pro Gly Phe Ala
305                 310                 315                 320

Glu Met Ala Ala Pro Leu Tyr Pro Leu Thr Lys Thr Gly Thr Leu Phe
                325                 330                 335

Asn Trp Gly Pro Asp Gln Gln Lys Ala Tyr Gln Glu Ile Lys Gln Ala
            340                 345                 350

Leu Leu Thr Ala Pro Ala Leu Gly Leu Pro Asp Leu Thr Lys Pro Phe
            355                 360                 365

Glu Leu Phe Val Asp Glu Lys Gln Gly Tyr Ala Lys Gly Val Leu Thr
            370                 375                 380

Gln Lys Leu Gly Pro Trp Arg Arg Pro Val Ala Tyr Leu Ser Lys Lys
385                 390                 395                 400

Leu Asp Pro Val Ala Ala Gly Trp Pro Pro Cys Leu Arg Met Val Ala
                405                 410                 415

Ala Ile Ala Val Leu Thr Lys Asp Ala Gly Lys Leu Thr Met Gly Gln
            420                 425                 430

Pro Leu Val Ile Leu Ala Pro His Ala Val Glu Ala Leu Val Lys Gln
            435                 440                 445

Pro Pro Asp Arg Trp Leu Ser Asn Ala Arg Met Thr His Tyr Gln Ala
            450                 455                 460

Leu Leu Leu Asp Thr Asp Arg Val Gln Phe Gly Pro Val Val Ala Leu
465                 470                 475                 480

Asn Pro Ala Thr Leu Leu Pro Leu Pro Glu Glu Gly Leu Gln His Asn
                485                 490                 495

Cys Leu Asp Ile Leu Ala Glu Ala His Gly Thr Arg Pro Asp Leu Thr
            500                 505                 510

Asp Gln Pro Leu Pro Asp Ala Asp His Thr Trp Tyr Thr Asp Gly Ser
            515                 520                 525

Ser Leu Leu Gln Glu Gly Gln Arg Lys Ala Gly Ala Ala Val Thr Thr
            530                 535                 540

Glu Thr Glu Val Ile Trp Ala Lys Ala Leu Pro Ala Gly Thr Ser Ala
545                 550                 555                 560

Gln Arg Ala Glu Leu Ile Ala Leu Thr Gln Ala Leu Lys Met Ala Glu
                565                 570                 575

Gly Lys Lys Leu Asn Val Tyr Thr Asp Ser Arg Tyr Ala Phe Ala Thr
            580                 585                 590

Ala His Ile His Gly Glu Ile Tyr Arg Arg Arg Gly Leu Leu Thr Ser
            595                 600                 605

Glu Gly Lys Glu Ile Lys Asn Lys Asp Glu Ile Leu Ala Leu Leu Lys
            610                 615                 620

Ala Leu Phe Leu Pro Lys Arg Leu Ser Ile Ile His Cys Pro Gly His
625                 630                 635                 640

Gln Lys Gly His Ser Ala Glu Ala Arg Gly Asn Arg Met Ala Asp Gln
                645                 650                 655

Ala Ala Arg Lys Ala Ala Ile Thr Glu Thr Pro Asp Thr Ser Thr Leu
            660                 665                 670
```

```
Leu Ser Ser Ser Ala Ser Lys Leu Glu Phe Thr Leu Gln Leu Glu Glu
        675                 680                 685

Glu Tyr Arg Leu Phe Glu Pro Glu Ser Thr Gln Lys Gln Glu Met Asp
        690                 695                 700

Ile Trp Leu Lys Asn Phe Pro Gln Ala Trp Ala Glu Thr Gly Gly Met
705                 710                 715                 720

Gly Met Ala His Cys Gln Ala Pro Val Leu Ile Gln Leu Lys Ala Thr
                725                 730                 735

Ala Thr Pro Ile Ser Ile Arg Gln Tyr Pro Met Pro His Glu Ala Tyr
            740                 745                 750

Gln Gly Ile Lys Pro His Ile Arg Arg Met Leu Asp Gln Gly Ile Leu
        755                 760                 765

Lys Pro Cys Gln Ser Pro Trp Asn Thr Pro Leu Leu Pro Val Lys Lys
770                 775                 780

Pro Gly Thr Lys Asp Tyr Arg Pro Val Gln Asp Leu Arg Glu Val Asn
785                 790                 795                 800

Lys Arg Val Glu Asp Ile His Pro Thr Val Pro Asn Pro Tyr Asn Leu
                805                 810                 815

Leu Ser Thr Leu Pro Pro Ser His Pro Trp Tyr Thr Val Leu Asp Leu
            820                 825                 830

Lys Asp Ala Phe Phe Cys Leu Arg Leu His Ser Glu Ser Gln Leu Leu
        835                 840                 845

Phe Ala Phe Glu Trp Arg Asp Pro Glu Ile Gly Leu Ser Gly Gln Leu
850                 855                 860

Thr Trp Thr Arg Leu Pro Gln Gly Phe Lys Asn Ser Pro Thr Leu Phe
865                 870                 875                 880

Asp Glu Ala Leu His Ser Asp Leu Ala Asp Phe Arg Val Arg Tyr Pro
                885                 890                 895

Ala Leu Val Leu Leu Gln Tyr Val Asp Asp Leu Leu Leu Ala Ala Ala
            900                 905                 910

Thr Arg Thr Glu Cys Leu Glu Gly Thr Lys Ala Leu Leu Glu Thr Leu
        915                 920                 925

Gly Asn Lys Gly Tyr Arg Ala Ser Ala Lys Lys Ala Gln Ile Cys Leu
930                 935                 940

Gln Glu Val Thr Tyr Leu Gly Tyr Ser Leu Lys Asp Gly Gln Arg Trp
945                 950                 955                 960

Leu Thr Lys Ala Arg Lys Glu Ala Ile Leu Ser Ile Pro Val Pro Lys
                965                 970                 975

Asn Pro Arg Gln Val Arg Glu Phe Leu Gly Thr Ala Gly Tyr Cys Arg
            980                 985                 990

Leu Trp Ile Pro Gly Phe Ala Glu Leu Ala Ala Pro Leu Tyr Pro Leu
        995                 1000                1005

Thr Arg Pro Gly Thr Leu Phe Gln Trp Gly Thr Glu Gln Gln Leu
        1010                1015                1020

Ala Phe Glu Asn Ile Arg Lys Ala Leu Leu Ser Ser Pro Ala Leu
        1025                1030                1035

Gly Leu Pro Asp Ile Thr Lys Pro Phe Glu Leu Phe Ile Asp Glu
        1040                1045                1050

Asn Ser Gly Phe Ala Lys Gly Val Leu Val Gln Lys Leu Gly Pro
        1055                1060                1065

Trp Lys Arg Pro Val Ala Tyr Leu Ser Lys Lys Leu Asp Thr Val
        1070                1075                1080
```

Ala Ser Gly Trp Pro Pro Cys Leu Arg Met Val Ala Ala Ile Ala
1085                1090                1095

Ile Leu Val Lys Asp Ala Gly Lys Leu Thr Leu Gly Gln Pro Leu
1100                1105                1110

Thr Ile Leu Thr Ser His Pro Val Glu Ala Leu Val Arg Gln Pro
1115                1120                1125

Pro Asn Lys Trp Leu Ser Asn Ala Arg Met Thr His Tyr Gln Ala
1130                1135                1140

Met Leu Leu Asp Ala Glu Arg Val His Phe Gly Pro Thr Val Ser
1145                1150                1155

Leu Asn Pro Ala Thr Leu Leu Pro Leu Pro Ser Gly Lys Pro Pro
1160                1165                1170

Arg Leu Ser Pro Asp Leu Ala Glu Thr Met Ala Gln Thr Asp Leu
1175                1180                1185

Thr Asp Gln Pro Leu Pro Asp Ala Asp Leu Thr Trp Tyr Thr Asn
1190                1195                1200

Gly Ser Ser Phe Ile Arg Asn Gly Glu Arg Lys Ala Gly Ala Ala
1205                1210                1215

Val Thr Thr Glu Ser Glu Val Ile Trp Ala Ala Ser Leu Pro Pro
1220                1225                1230

Gly Thr Ser Ala Gln Arg Ala Glu Leu Ile Ala Leu Thr Gln Ala
1235                1240                1245

Leu Lys Met Ala Lys Gly Lys Lys Leu Thr Val Tyr Thr Asp Ser
1250                1255                1260

Arg Tyr Ala Phe Ala Thr Ala His Val His Gly Glu Ile Tyr Arg
1265                1270                1275

Arg Arg Gly Leu Leu Thr Ser Glu Gly Lys Glu Ile Lys Asn Lys
1280                1285                1290

Asn Glu Ile Leu Ala Leu Leu Glu Ala Leu Phe Leu Pro Lys Arg
1295                1300                1305

Leu Ser Ile Ile His Cys Pro Gly His Gln Lys Gly Asp Ser Pro
1310                1315                1320

Gln Ala Lys Gly Asn Arg Leu Ala Asp Asp Thr Ala Lys Lys Ala
1325                1330                1335

Ala Thr Glu Thr Gln Ser Ser Leu Thr Ile Leu Ser Ser Ser Ala
1340                1345                1350

Ser

<210> SEQ ID NO 18
<211> LENGTH: 1358
<212> TYPE: PRT
<213> ORGANISM: Artificial Sequence
<220> FEATURE:
<223> OTHER INFORMATION: Synthetic construct

<400> SEQUENCE: 18

Glu Phe Thr Leu Asn Ile Glu Asp Glu His Arg Leu His Glu Thr Ser
1               5                   10                  15

Lys Glu Pro Asp Val Ser Leu Gly Ser Thr Trp Leu Ser Asp Phe Pro
            20                  25                  30

Gln Ala Trp Ala Glu Thr Gly Gly Met Gly Leu Ala Val Arg Gln Ala
        35                  40                  45

Pro Leu Ile Ile Pro Leu Lys Ala Thr Ser Thr Pro Val Ser Ile Lys
    50                  55                  60

Gln Tyr Pro Met Ser Gln Glu Ala Arg Leu Gly Ile Lys Pro His Ile

```
                65                  70                  75                  80
        Gln Arg Leu Leu Asp Gln Gly Ile Leu Val Pro Cys Gln Ser Pro Trp
                         85                  90                  95
        Asn Thr Pro Leu Leu Pro Val Lys Lys Pro Gly Thr Asn Asp Tyr Arg
                        100                 105                 110
        Pro Val Gln Asp Leu Arg Glu Val Asn Lys Arg Val Glu Asp Ile His
                        115                 120                 125
        Pro Thr Val Pro Asn Pro Tyr Asn Leu Leu Ser Gly Leu Pro Pro Ser
                130                 135                 140
        His Gln Trp Tyr Thr Val Leu Asp Leu Lys Asp Ala Phe Phe Cys Leu
        145                 150                 155                 160
        Arg Leu His Pro Thr Ser Gln Pro Leu Phe Ala Phe Glu Trp Arg Asp
                        165                 170                 175
        Pro Glu Met Gly Ile Ser Gly Gln Leu Thr Trp Thr Arg Leu Pro Gln
                        180                 185                 190
        Gly Phe Lys Asn Ser Pro Thr Leu Phe Asp Glu Ala Leu His Arg Asp
                        195                 200                 205
        Leu Ala Asp Phe Arg Ile Gln His Pro Asp Leu Ile Leu Leu Gln Tyr
                210                 215                 220
        Val Asp Asp Leu Leu Leu Ala Ala Thr Ser Glu Leu Asp Cys Gln Gln
        225                 230                 235                 240
        Gly Thr Arg Ala Leu Leu Gln Thr Leu Gly Asn Leu Gly Tyr Arg Ala
                        245                 250                 255
        Ser Ala Lys Lys Ala Gln Ile Cys Gln Lys Gln Val Lys Tyr Leu Gly
                        260                 265                 270
        Tyr Leu Leu Lys Glu Gly Gln Arg Trp Leu Thr Glu Ala Arg Lys Glu
                        275                 280                 285
        Thr Val Met Gly Gln Pro Thr Pro Lys Thr Pro Arg Gln Leu Arg Glu
                290                 295                 300
        Phe Leu Gly Thr Ala Gly Phe Cys Arg Leu Trp Ile Pro Gly Phe Ala
        305                 310                 315                 320
        Glu Met Ala Ala Pro Leu Tyr Pro Leu Thr Lys Thr Gly Thr Leu Phe
                        325                 330                 335
        Asn Trp Gly Pro Asp Gln Gln Lys Ala Tyr Gln Glu Ile Lys Gln Ala
                        340                 345                 350
        Leu Leu Thr Ala Pro Ala Leu Gly Leu Pro Asp Leu Thr Lys Pro Phe
                        355                 360                 365
        Glu Leu Phe Val Asp Glu Lys Gln Gly Tyr Ala Lys Gly Val Leu Thr
                370                 375                 380
        Gln Lys Leu Gly Pro Trp Arg Arg Pro Val Ala Tyr Leu Ser Lys Lys
        385                 390                 395                 400
        Leu Asp Pro Val Ala Ala Gly Trp Pro Pro Cys Leu Arg Met Val Ala
                        405                 410                 415
        Ala Ile Ala Val Leu Thr Lys Asp Ala Gly Lys Leu Thr Met Gly Gln
                        420                 425                 430
        Pro Leu Val Ile Leu Ala Pro His Ala Val Glu Ala Leu Val Lys Gln
                        435                 440                 445
        Pro Pro Asp Arg Trp Leu Ser Asn Ala Arg Met Thr His Tyr Gln Ala
                        450                 455                 460
        Leu Leu Leu Asp Thr Asp Arg Val Gln Phe Gly Pro Val Val Ala Leu
        465                 470                 475                 480
        Asn Pro Ala Thr Leu Leu Pro Leu Pro Glu Glu Gly Leu Gln His Asn
                        485                 490                 495
```

-continued

```
Cys Leu Asp Ile Leu Ala Glu Ala His Gly Thr Arg Pro Asp Leu Thr
            500                 505                 510

Asp Gln Pro Leu Pro Asp Ala Asp His Thr Trp Tyr Thr Asp Gly Ser
        515                 520                 525

Ser Leu Leu Gln Glu Gly Gln Arg Lys Ala Gly Ala Ala Val Thr Thr
    530                 535                 540

Glu Thr Glu Val Ile Trp Ala Lys Ala Leu Pro Ala Gly Thr Ser Ala
545                 550                 555                 560

Gln Arg Ala Glu Leu Ile Ala Leu Thr Gln Ala Leu Lys Met Ala Glu
                565                 570                 575

Gly Lys Lys Leu Asn Val Tyr Thr Asp Ser Arg Tyr Ala Phe Ala Thr
            580                 585                 590

Ala His Ile His Gly Glu Ile Tyr Arg Arg Gly Leu Leu Thr Ser
        595                 600                 605

Glu Gly Lys Glu Ile Lys Asn Lys Asp Glu Ile Leu Ala Leu Leu Lys
    610                 615                 620

Ala Leu Phe Leu Pro Lys Arg Leu Ser Ile Ile His Cys Pro Gly His
625                 630                 635                 640

Gln Lys Gly His Ser Ala Glu Ala Arg Gly Asn Arg Met Ala Asp Gln
                645                 650                 655

Ala Ala Arg Lys Ala Ala Ile Thr Glu Thr Pro Asp Thr Ser Thr Leu
            660                 665                 670

Leu Ser Ser Ser Ala Ser Lys Leu Glu Phe Thr Leu Asn Ile Glu Asp
        675                 680                 685

Glu His Arg Leu His Glu Thr Ser Lys Glu Pro Asp Val Ser Leu Gly
    690                 695                 700

Ser Thr Trp Leu Ser Asp Phe Pro Gln Ala Trp Ala Glu Thr Gly Gly
705                 710                 715                 720

Met Gly Leu Ala Val Arg Gln Ala Pro Leu Ile Ile Pro Leu Lys Ala
                725                 730                 735

Thr Ser Thr Pro Val Ser Ile Lys Gln Tyr Pro Met Ser Gln Glu Ala
            740                 745                 750

Arg Leu Gly Ile Lys Pro His Ile Gln Arg Leu Leu Asp Gln Gly Ile
        755                 760                 765

Leu Val Pro Cys Gln Ser Pro Trp Asn Thr Pro Leu Leu Pro Val Lys
    770                 775                 780

Lys Pro Gly Thr Asn Asp Tyr Arg Pro Val Gln Asp Leu Arg Glu Val
785                 790                 795                 800

Asn Lys Arg Val Glu Asp Ile His Pro Thr Val Pro Asn Pro Tyr Asn
                805                 810                 815

Leu Leu Ser Gly Leu Pro Pro Ser His Gln Trp Tyr Thr Val Leu Asp
            820                 825                 830

Leu Lys Asp Ala Phe Phe Cys Leu Arg Leu His Pro Thr Ser Gln Pro
        835                 840                 845

Leu Phe Ala Phe Glu Trp Arg Asp Pro Glu Met Gly Ile Ser Gly Gln
    850                 855                 860

Leu Thr Trp Thr Arg Leu Pro Gln Gly Phe Lys Asn Ser Pro Thr Leu
865                 870                 875                 880

Phe Asp Glu Ala Leu His Arg Asp Leu Ala Asp Phe Arg Ile Gln His
                885                 890                 895

Pro Asp Leu Ile Leu Leu Gln Tyr Val Asp Asp Leu Leu Leu Ala Ala
            900                 905                 910
```

```
Thr Ser Glu Leu Asp Cys Gln Gln Gly Thr Arg Ala Leu Leu Gln Thr
            915                 920                 925

Leu Gly Asn Leu Gly Tyr Arg Ala Ser Ala Lys Lys Ala Gln Ile Cys
            930                 935                 940

Gln Lys Gln Val Lys Tyr Leu Gly Tyr Leu Leu Lys Glu Gly Gln Arg
945                 950                 955                 960

Trp Leu Thr Glu Ala Arg Lys Glu Thr Val Met Gly Gln Pro Thr Pro
            965                 970                 975

Lys Thr Pro Arg Gln Leu Arg Glu Phe Leu Gly Thr Ala Gly Phe Cys
            980                 985                 990

Arg Leu Trp Ile Pro Gly Phe Ala  Glu Met Ala Ala Pro  Leu Tyr Pro
            995                1000                1005

Leu Thr  Lys Thr Gly Thr Leu  Phe Asn Trp Gly Pro  Asp Gln Gln
       1010                1015                1020

Lys Ala  Tyr Gln Glu Ile Lys  Gln Ala Leu Leu Thr  Ala Pro Ala
       1025                1030                1035

Leu Gly  Leu Pro Asp Leu Thr  Lys Pro Phe Glu Leu  Phe Val Asp
       1040                1045                1050

Glu Lys  Gln Gly Tyr Ala Lys  Gly Val Leu Thr Gln  Lys Leu Gly
1055                1060                1065

Pro Trp  Arg Arg Pro Val Ala  Tyr Leu Ser Lys Lys  Leu Asp Pro
       1070                1075                1080

Val Ala  Ala Gly Trp Pro Pro  Cys Leu Arg Met Val  Ala Ala Ile
       1085                1090                1095

Ala Val  Leu Thr Lys Asp Ala  Gly Lys Leu Thr Met  Gly Gln Pro
       1100                1105                1110

Leu Val  Ile Leu Ala Pro His  Ala Val Glu Ala Leu  Val Lys Gln
       1115                1120                1125

Pro Pro  Asp Arg Trp Leu Ser  Asn Ala Arg Met Thr  His Tyr Gln
       1130                1135                1140

Ala Leu  Leu Leu Asp Thr Asp  Arg Val Gln Phe Gly  Pro Val Val
       1145                1150                1155

Ala Leu  Asn Pro Ala Thr Leu  Leu Pro Leu Pro Glu  Glu Gly Leu
       1160                1165                1170

Gln His  Asn Cys Leu Asp Ile  Leu Ala Glu Ala His  Gly Thr Arg
       1175                1180                1185

Pro Asp  Leu Thr Asp Gln Pro  Leu Pro Asp Ala Asp  His Thr Trp
       1190                1195                1200

Tyr Thr  Asn Gly Ser Ser Leu  Leu Gln Glu Gly Gln  Arg Lys Ala
       1205                1210                1215

Gly Ala  Ala Val Thr Thr Glu  Thr Glu Val Ile Trp  Ala Lys Ala
       1220                1225                1230

Leu Pro  Ala Gly Thr Ser Ala  Gln Arg Ala Glu Leu  Ile Ala Leu
       1235                1240                1245

Thr Gln  Ala Leu Lys Met Ala  Glu Gly Lys Lys Leu  Asn Val Tyr
       1250                1255                1260

Thr Asp  Ser Arg Tyr Ala Phe  Ala Thr Ala His Ile  His Gly Glu
       1265                1270                1275

Ile Tyr  Arg Arg Arg Gly Leu  Leu Thr Ser Glu Gly  Lys Glu Ile
       1280                1285                1290

Lys Asn  Lys Asp Glu Ile Leu  Ala Leu Leu Lys Ala  Leu Phe Leu
       1295                1300                1305

Pro Lys  Arg Leu Ser Ile Ile  His Cys Pro Gly His  Gln Lys Gly
```

```
                1310                1315                1320

His Ser Ala Glu Ala Arg Gly Asn Arg Met Ala Asp Gln Ala Ala
    1325                1330                1335

Arg Lys Ala Ala Ile Thr Glu Thr Pro Asp Thr Ser Thr Leu Leu
    1340                1345                1350

Ser Ser Ser Ala Ser
    1355
```